(12) United States Patent
Yang et al.

(10) Patent No.: US 10,415,033 B2
(45) Date of Patent: Sep. 17, 2019

(54) PHAGE-DISPLAYED SINGLE-CHAIN VARIABLE FRAGMENT LIBRARIES AND USES THEREOF

(71) Applicant: Academia Sinica, Taipei (TW)

(72) Inventors: An-Suei Yang, Emeryville, CA (US); Jhih-Wei Jian, Taipei (TW); Hong-Sen Chen, Taipei (TW); Yi-Kai Chiu, Taipei (TW); Hung-Pin Peng, Taipei (TW); Chao-Ping Tung, Taipei (TW); Chung-Ming Yu, Taipei (TW); Wei-Ying Kuo, Taipei (TW); Hung-Ju Hsu, Taipei (TW)

(73) Assignee: Academia Sinica, Taipei (TW)

( * ) Notice: Subject to any disclaimer, the term of this patent is extended or adjusted under 35 U.S.C. 154(b) by 0 days.

(21) Appl. No.: 16/202,106

(22) Filed: Nov. 28, 2018

(65) Prior Publication Data

US 2019/0085323 A1    Mar. 21, 2019

Related U.S. Application Data

(63) Continuation-in-part of application No. 15/547,523, filed on Jul. 31, 2017.

(51) Int. Cl.
| | | |
|---|---|---|
| *C12N 15/10* | (2006.01) | |
| *C40B 40/02* | (2006.01) | |
| *C07K 16/00* | (2006.01) | |
| *C07K 16/32* | (2006.01) | |
| *C07K 16/30* | (2006.01) | |
| *C07K 16/22* | (2006.01) | |
| *C07K 16/28* | (2006.01) | |

(52) U.S. Cl.
CPC ........ *C12N 15/1037* (2013.01); *C07K 16/005* (2013.01); *C07K 16/22* (2013.01); *C07K 16/2827* (2013.01); *C07K 16/30* (2013.01); *C07K 16/32* (2013.01); *C40B 40/02* (2013.01); *C07K 2317/33* (2013.01); *C07K 2317/622* (2013.01); *C07K 2317/92* (2013.01)

(58) Field of Classification Search
None
See application file for complete search history.

(56) References Cited

PUBLICATIONS

Cobaugh, Christian Wessel. "Single scaffold antibody libraries created with high rates of mutagenesis or diversity focused for peptide recognition." Thesis (2007) (Year: 2007).*

\* cited by examiner

*Primary Examiner* — Tracy Vivlemore
*Assistant Examiner* — Sahana S Kaup

(57) ABSTRACT

Disclosed herein is a phage-displayed single-chain variable fragment (scFv) library, which comprises a plurality of phage-displayed scFvs characterized in having a specific CS combination and a specific sequence in each CDR. The present scFv library is useful in efficiently producing different antibodies with binding affinity to different antigens. Accordingly, the present disclosure provides a potential means to generate different antigen-specific antibodies promptly in accordance with the need in experimental researches and/or clinical applications.

20 Claims, 9 Drawing Sheets

Specification includes a Sequence Listing.

SEQUENCE LISTING

<160> NUMBER OF SEQ ID NOS: 210

<210> SEQ ID NO 1
<211> LENGTH: 72
<212> TYPE: DNA
<213> ORGANISM: Artificial Sequence
<220> FEATURE:
<223> OTHER INFORMATION: synthesized-CDR-L1

<400> SEQUENCE: 1
gatcgcgtga ccattacctg ccgtgcgagc caggatgtta gcacggcggt cgcatggtat    60
cagcagaaac ca                                                        72

<210> SEQ ID NO 2
<211> LENGTH: 66
<212> TYPE: DNA
<213> ORGANISM: Artificial Sequence
<220> FEATURE:
<223> OTHER INFORMATION: synthesized-CDR-L2

<400> SEQUENCE: 2
aaagcgccga acttctgat atactctgcg tccttcctgt atagcggcgt gccgtcgcgt     60
ttttcg                                                               66

<210> SEQ ID NO 3
<211> LENGTH: 75
<212> TYPE: DNA
<213> ORGANISM: Artificial Sequence
<220> FEATURE:
<223> OTHER INFORMATION: synthesized-CDR-L3

<400> SEQUENCE: 3
ccggaggatt ttgcgaccta ctactgtcaa cagcattata ccacaccgcc gaccttcggt    60
caaggcacca aagtg                                                     75

<210> SEQ ID NO 4
<211> LENGTH: 81
<212> TYPE: DNA
<213> ORGANISM: Artificial Sequence
<220> FEATURE:
<223> OTHER INFORMATION: synthesized-CDR-H1

<400> SEQUENCE: 4
ggcagccttc gtctgagctg tgcggcgagc gggttcacca ttagcgatta ctggattcat    60
tgggtgcgtc aagctcccgg c                                              81

<210> SEQ ID NO 5
<211> LENGTH: 78
<212> TYPE: DNA
<213> ORGANISM: Artificial Sequence
<220> FEATURE:
<223> OTHER INFORMATION: synthesized-CDR-H2

<400> SEQUENCE: 5
aaggggctgg agtgggtcgc gggcattacg cccgctggcg gttacacata ttatgccgac    60
agcgtgaaag gtcgcttt                                                  78

<210> SEQ ID NO 6
<211> LENGTH: 93
<212> TYPE: DNA
<213> ORGANISM: Artificial Sequence
<220> FEATURE:
<223> OTHER INFORMATION: synthesized-CDR-H3

```
<400> SEQUENCE: 6
cgtgcggaag acacagcggt gtattattgc gcgcgtttcg tgttttttct gccgtatgcg      60
atggattatt gggggcaggg caccctttgtt acc                                  93

<210> SEQ ID NO 7
<211> LENGTH: 90
<212> TYPE: DNA
<213> ORGANISM: Artificial Sequence
<220> FEATURE:
<223> OTHER INFORMATION: synthesized-Primer-9AL101
<220> FEATURE:
<221> NAME/KEY: variation
<222> LOCATION: 43,52,58,70
<223> OTHER INFORMATION: /note="n is A, T, C or G"

<400> SEQUENCE: 7
gatcgcgtga ccattacctg caaaagtaac cagaacctgc tgnwytctgg cnaycaaggg      60
accthyctgn wytggtatca gcagaaacca                                       90

<210> SEQ ID NO 8
<211> LENGTH: 51
<212> TYPE: DNA
<213> ORGANISM: Artificial Sequence
<220> FEATURE:
<223> OTHER INFORMATION: synthesized-9AL101
<220> FEATURE:
<221> NAME/KEY: variation
<222> LOCATION: 22,31,37,49
<223> OTHER INFORMATION: /note="n is A, T, C or G"

<400> SEQUENCE: 8
aaaagtaacc agaacctgct gnwytctggc naycaangga ccthyctgnw y               51

<210> SEQ ID NO 9
<211> LENGTH: 87
<212> TYPE: DNA
<213> ORGANISM: Artificial Sequence
<220> FEATURE:
<223> OTHER INFORMATION: synthesized-Primer-9AL102
<220> FEATURE:
<221> NAME/KEY: variation
<222> LOCATION: 43,49,55,67
<223> OTHER INFORMATION: /note="n is A, T, C or G"

<400> SEQUENCE: 9
gatcgcgtga ccattacctg caaaagtaac cagaacctgc tgnwytctna yggcnggacc      60
thyctgnwyt ggtatcagca gaaacca                                          87

<210> SEQ ID NO 10
<211> LENGTH: 48
<212> TYPE: DNA
<213> ORGANISM: Artificial Sequence
<220> FEATURE:
<223> OTHER INFORMATION: synthesized-9AL102
<220> FEATURE:
<221> NAME/KEY: variation
<222> LOCATION: 22,28,34,46
<223> OTHER INFORMATION: /note="n is A, T, C or G"

<400> SEQUENCE: 10
aaaagtaacc agaacctgct gnwytctnay ggcnggacct hyctgnwy                   48

<210> SEQ ID NO 11
<211> LENGTH: 66
<212> TYPE: DNA
```

```
<213> ORGANISM: Artificial Sequence
<220> FEATURE:
<223> OTHER INFORMATION: synthesized-Primer-9AL201
<220> FEATURE:
<221> NAME/KEY: variation
<222> LOCATION: 25,34
<223> OTHER INFORMATION: /note="n is A, T, C or G"

<400> SEQUENCE: 11
aaagcgccga aacttctgat athynggryr tctnggctgt atagcggcgt gccgtcgcgt    60
ttttcg                                                                66

<210> SEQ ID NO 12
<211> LENGTH: 24
<212> TYPE: DNA
<213> ORGANISM: Artificial Sequence
<220> FEATURE:
<223> OTHER INFORMATION: synthesized-9AL201
<220> FEATURE:
<221> NAME/KEY: variation
<222> LOCATION: 4,13
<223> OTHER INFORMATION: /note="n is A, T, C or G"

<400> SEQUENCE: 12
thynggryrt ctnggctgta tagc                                            24

<210> SEQ ID NO 13
<211> LENGTH: 66
<212> TYPE: DNA
<213> ORGANISM: Artificial Sequence
<220> FEATURE:
<223> OTHER INFORMATION: synthesized-Primer-9AL202
<220> FEATURE:
<221> NAME/KEY: variation
<222> LOCATION: 25,34
<223> OTHER INFORMATION: /note="n is A, T, C or G"

<400> SEQUENCE: 13
aaagcgccga aacttctgat athynggryr tctnwyctgt atagcggcgt gccgtcgcgt    60
ttttcg                                                                66

<210> SEQ ID NO 14
<211> LENGTH: 24
<212> TYPE: DNA
<213> ORGANISM: Artificial Sequence
<220> FEATURE:
<223> OTHER INFORMATION: synthesized-9AL202
<220> FEATURE:
<221> NAME/KEY: variation
<222> LOCATION: 4,13
<223> OTHER INFORMATION: /note="n is A, T, C or G"

<400> SEQUENCE: 14
thynggryrt ctnwyctgta tagc                                            24

<210> SEQ ID NO 15
<211> LENGTH: 66
<212> TYPE: DNA
<213> ORGANISM: Artificial Sequence
<220> FEATURE:
<223> OTHER INFORMATION: synthesized-Primer-9AL203
<220> FEATURE:
<221> NAME/KEY: variation
<222> LOCATION: 34
<223> OTHER INFORMATION: /note="n is A, T, C or G"

<400> SEQUENCE: 15
aaagcgccga aacttctgat athybwyryr tctnggctgt atagcggcgt gccgtcgcgt    60
```

```
tttccg                                                                   66

<210> SEQ ID NO 16
<211> LENGTH: 24
<212> TYPE: DNA
<213> ORGANISM: Artificial Sequence
<220> FEATURE:
<223> OTHER INFORMATION: synthesized-9AL203
<220> FEATURE:
<221> NAME/KEY: variation
<222> LOCATION: 13
<223> OTHER INFORMATION: /note="n is A, T, C or G"

<400> SEQUENCE: 16
thybwyryrt ctnggctgta tagc                                               24

<210> SEQ ID NO 17
<211> LENGTH: 66
<212> TYPE: DNA
<213> ORGANISM: Artificial Sequence
<220> FEATURE:
<223> OTHER INFORMATION: synthesized-Primer-9AL204
<220> FEATURE:
<221> NAME/KEY: variation
<222> LOCATION: 34
<223> OTHER INFORMATION: /note="n is A, T, C or G"

<400> SEQUENCE: 17
aaagcgccga aacttctgat athybwyryr tctnwyctgt atagcggcgt gccgtcgcgt        60
ttttcg                                                                   66

<210> SEQ ID NO 18
<211> LENGTH: 24
<212> TYPE: DNA
<213> ORGANISM: Artificial Sequence
<220> FEATURE:
<223> OTHER INFORMATION: synthesized-9AL204
<220> FEATURE:
<221> NAME/KEY: variation
<222> LOCATION: 13
<223> OTHER INFORMATION: /note="n is A, T, C or G"

<400> SEQUENCE: 18
thybwyryrt ctnwyctgta tagc                                               24

<210> SEQ ID NO 19
<211> LENGTH: 75
<212> TYPE: DNA
<213> ORGANISM: Artificial Sequence
<220> FEATURE:
<223> OTHER INFORMATION: synthesized-Primer-9AL301

<400> SEQUENCE: 19
ccggaggatt ttgcgaccta ctactgtthy cagrsywhyv rybwycccckg gaccttcggt       60 caaggcacca aagtg                                                         75

<210> SEQ ID NO 20
<211> LENGTH: 27
<212> TYPE: DNA
<213> ORGANISM: Artificial Sequence
<220> FEATURE:
<223> OTHER INFORMATION: synthesized-9AL301

<400> SEQUENCE: 20
thycagrsyw hyvrybwycc ckggacc                                            27
```

<210> SEQ ID NO 21
<211> LENGTH: 75
<212> TYPE: DNA
<213> ORGANISM: Artificial Sequence
<220> FEATURE:
<223> OTHER INFORMATION: synthesized-Primer-9AL302

<400> SEQUENCE: 21
ccggaggatt ttgcgaccta ctactgtthy cagrsywhyv rybwycccth yaccttcggt    60
caaggcacca aagtg                                                    75

<210> SEQ ID NO 22
<211> LENGTH: 27
<212> TYPE: DNA
<213> ORGANISM: Artificial Sequence
<220> FEATURE:
<223> OTHER INFORMATION: synthesized-9AL302

<400> SEQUENCE: 22
thycagrsyw hyvrybwycc cthyacc                                       27

<210> SEQ ID NO 23
<211> LENGTH: 81
<212> TYPE: DNA
<213> ORGANISM: Artificial Sequence
<220> FEATURE:
<223> OTHER INFORMATION: synthesized-Primer-9AH101

<400> SEQUENCE: 23
ggcagccttc gtctgagctg taaggcgtct ggctatacct tcrsyrsyth ythyatgbwy    60
tgggtgcgtc aagctcccgg c                                             81

<210> SEQ ID NO 24
<211> LENGTH: 39
<212> TYPE: DNA
<213> ORGANISM: Artificial Sequence
<220> FEATURE:
<223> OTHER INFORMATION: synthesized-9AH101

<400> SEQUENCE: 24
aaggcgtctg gctatacctt crsyrsythy thyatgbwy                           39

<210> SEQ ID NO 25
<211> LENGTH: 81
<212> TYPE: DNA
<213> ORGANISM: Artificial Sequence
<220> FEATURE:
<223> OTHER INFORMATION: synthesized-Primer-9AH102

<400> SEQUENCE: 25
ggcagccttc gtctgagctg taaggcgtct ggctatacct tcrsyrsyth ykggatgbwy    60
tgggtgcgtc aagctcccgg c                                             81

<210> SEQ ID NO 26
<211> LENGTH: 39
<212> TYPE: DNA
<213> ORGANISM: Artificial Sequence
<220> FEATURE:
<223> OTHER INFORMATION: synthesized-9AH102

<400> SEQUENCE: 26
aaggcgtctg gctatacctt crsyrsythy kggatgbwy                           39

<210> SEQ ID NO 27
<211> LENGTH: 81
<212> TYPE: DNA
<213> ORGANISM: Artificial Sequence
<220> FEATURE:
<223> OTHER INFORMATION: synthesized-Primer-9AH103

<400> SEQUENCE: 27
ggcagccttc gtctgagctg taaggcgtct ggctatacct tcrsyrsykg gthyatgbwy    60
tgggtgcgtc aagctcccgg c                                             81

<210> SEQ ID NO 28
<211> LENGTH: 39
<212> TYPE: DNA
<213> ORGANISM: Artificial Sequence
<220> FEATURE:
<223> OTHER INFORMATION: synthesized-9AH103

<400> SEQUENCE: 28
aaggcgtctg gctataacctt crsyrsykgg thyatgbwy                           39

<210> SEQ ID NO 29
<211> LENGTH: 81
<212> TYPE: DNA
<213> ORGANISM: Artificial Sequence
<220> FEATURE:
<223> OTHER INFORMATION: synthesized-Primer-9AH104

<400> SEQUENCE: 29
ggcagccttc gtctgagctg taaggcgtct ggctatacct tcrsyrsykg gkggatgbwy    60
tgggtgcgtc aagctcccgg c                                             81

<210> SEQ ID NO 30
<211> LENGTH: 39
<212> TYPE: DNA
<213> ORGANISM: Artificial Sequence
<220> FEATURE:
<223> OTHER INFORMATION: synthesized-9AH104

<400> SEQUENCE: 30
aaggcgtctg gctataacctt crsyrsykgg kggatgbwy                           39

<210> SEQ ID NO 31
<211> LENGTH: 81
<212> TYPE: DNA
<213> ORGANISM: Artificial Sequence
<220> FEATURE:
<223> OTHER INFORMATION: synthesized-Primer-9AH105

<400> SEQUENCE: 31
ggcagccttc gtctgagctg taaggcgtct ggctatacct tcrsysryth ythyatgbwy    60
tgggtgcgtc aagctcccgg c                                             81

<210> SEQ ID NO 32
<211> LENGTH: 39
<212> TYPE: DNA
<213> ORGANISM: Artificial Sequence
<220> FEATURE:
<223> OTHER INFORMATION: synthesized-9AH105

<400> SEQUENCE: 32
aaggcgtctg gctataacctt crsysrythy thyatgbwy                           39

<210> SEQ ID NO 33

```
<211> LENGTH: 81
<212> TYPE: DNA
<213> ORGANISM: Artificial Sequence
<220> FEATURE:
<223> OTHER INFORMATION: synthesized-Primer-9AH106

<400> SEQUENCE: 33
ggcagccttc gtctgagctg taaggcgtct ggctatacct tcrsysryth ykggatgbwy    60
tgggtgcgtc aagctcccgg c                                              81

<210> SEQ ID NO 34
<211> LENGTH: 39
<212> TYPE: DNA
<213> ORGANISM: Artificial Sequence
<220> FEATURE:
<223> OTHER INFORMATION: synthesized-9AH106

<400> SEQUENCE: 34
aaggcgtctg gctatacctt crsysrythy kggatgbwy                           39

<210> SEQ ID NO 35
<211> LENGTH: 81
<212> TYPE: DNA
<213> ORGANISM: Artificial Sequence
<220> FEATURE:
<223> OTHER INFORMATION: synthesized-Primer-9AH107

<400> SEQUENCE: 35
ggcagccttc gtctgagctg taaggcgtct ggctatacct tcrsysrykg gthyatgbwy    60
tgggtgcgtc aagctcccgg c                                              81

<210> SEQ ID NO 36
<211> LENGTH: 39
<212> TYPE: DNA
<213> ORGANISM: Artificial Sequence
<220> FEATURE:
<223> OTHER INFORMATION: synthesized-9AH107

<400> SEQUENCE: 36
aaggcgtctg gctatacctt crsysrykgg thyatgbwy                           39

<210> SEQ ID NO 37
<211> LENGTH: 81
<212> TYPE: DNA
<213> ORGANISM: Artificial Sequence
<220> FEATURE:
<223> OTHER INFORMATION: synthesized-Primer-9AH108

<400> SEQUENCE: 37
ggcagccttc gtctgagctg taaggcgtct ggctatacct tcrsysrykg gkggatgbwy    60
tgggtgcgtc aagctcccgg c                                              81

<210> SEQ ID NO 38
<211> LENGTH: 39
<212> TYPE: DNA
<213> ORGANISM: Artificial Sequence
<220> FEATURE:
<223> OTHER INFORMATION: synthesized-9AH108

<400> SEQUENCE: 38
aaggcgtctg gctatacctt crsysrykgg kggatgbwy                           39

<210> SEQ ID NO 39
<211> LENGTH: 78
```

<212> TYPE: DNA
<213> ORGANISM: Artificial Sequence
<220> FEATURE:
<223> OTHER INFORMATION: synthesized-Primer-9AH201
<220> FEATURE:
<221> NAME/KEY: variation
<222> LOCATION: 34,43
<223> OTHER INFORMATION: /note="n is A, T, C or G"

<400> SEQUENCE: 39
aaggggctgg agtgggtcgc gthyatcdmy ccanaybwyg gcnwyacabw ytatgccgac    60
agcgtgaaag gtcgcttt                                                  78

<210> SEQ ID NO 40
<211> LENGTH: 30
<212> TYPE: DNA
<213> ORGANISM: Artificial Sequence
<220> FEATURE:
<223> OTHER INFORMATION: synthesized-9AH201
<220> FEATURE:
<221> NAME/KEY: variation
<222> LOCATION: 13,22
<223> OTHER INFORMATION: /note="n is A, T, C or G"

<400> SEQUENCE: 40
thyatcdmyc canaybwygg cnwyacabwy                                     30

<210> SEQ ID NO 41
<211> LENGTH: 78
<212> TYPE: DNA
<213> ORGANISM: Artificial Sequence
<220> FEATURE:
<223> OTHER INFORMATION: synthesized-Primer-9AH202
<220> FEATURE:
<221> NAME/KEY: variation
<222> LOCATION: 34,43
<223> OTHER INFORMATION: /note="n is A, T, C or G"

<400> SEQUENCE: 41
aaggggctgg agtgggtcgc gsryatcdmy ccanaybwyg gcnwyacabw ytatgccgac    60
agcgtgaaag gtcgcttt                                                  78

<210> SEQ ID NO 42
<211> LENGTH: 30
<212> TYPE: DNA
<213> ORGANISM: Artificial Sequence
<220> FEATURE:
<223> OTHER INFORMATION: synthesized-9AH202
<220> FEATURE:
<221> NAME/KEY: variation
<222> LOCATION: 13,22
<223> OTHER INFORMATION: /note="n is A, T, C or G"

<400> SEQUENCE: 42
sryatcdmyc canaybwygg cnwyacabwy                                     30

<210> SEQ ID NO 43
<211> LENGTH: 72
<212> TYPE: DNA
<213> ORGANISM: Artificial Sequence
<220> FEATURE:
<223> OTHER INFORMATION: synthesized-Primer-9AH3601
<220> FEATURE:
<221> NAME/KEY: variation
<222> LOCATION: 34,43
<223> OTHER INFORMATION: /note="n is A, T, C or G"

<400> SEQUENCE: 43

```
cgtgcggaag acacagcggt gtattattgc gcgnggkggt hynaytattg ggggcagggc    60
acccttgtta cc                                                       72
```

<210> SEQ ID NO 44
<211> LENGTH: 72
<212> TYPE: DNA
<213> ORGANISM: Artificial Sequence
<220> FEATURE:
<223> OTHER INFORMATION: synthesized-Primer-9AH3602
<220> FEATURE:
<221> NAME/KEY: variation
<222> LOCATION: 34,43
<223> OTHER INFORMATION: /note="n is A, T, C or G"

<400> SEQUENCE: 44

```
cgtgcggaag acacagcggt gtattattgc gcgnggthyk ggnaytattg ggggcagggc    60
acccttgtta cc                                                       72
```

<210> SEQ ID NO 45
<211> LENGTH: 12
<212> TYPE: DNA
<213> ORGANISM: Artificial Sequence
<220> FEATURE:
<223> OTHER INFORMATION: synthesized-9AH3601
<220> FEATURE:
<221> NAME/KEY: variation
<222> LOCATION: 1,10
<223> OTHER INFORMATION: /note="n is A, T, C or G"

<400> SEQUENCE: 45

```
nggkggthyn ay                                                       12
```

<210> SEQ ID NO 46
<211> LENGTH: 12
<212> TYPE: DNA
<213> ORGANISM: Artificial Sequence
<220> FEATURE:
<223> OTHER INFORMATION: synthesized-9AH3602
<220> FEATURE:
<221> NAME/KEY: variation
<222> LOCATION: 1,10
<223> OTHER INFORMATION: /note="n is A, T, C or G"

<400> SEQUENCE: 46

```
nggthykggn ay                                                       12
```

<210> SEQ ID NO 47
<211> LENGTH: 75
<212> TYPE: DNA
<213> ORGANISM: Artificial Sequence
<220> FEATURE:
<223> OTHER INFORMATION: synthesized-Primer-9AH3701
<220> FEATURE:
<221> NAME/KEY: variation
<222> LOCATION: 34,46
<223> OTHER INFORMATION: /note="n is A, T, C or G"

<400> SEQUENCE: 47

```
cgtgcggaag acacagcggt gtattattgc gcgnggkggt hythynayta ttgggggcag    60
ggcacccttg ttacc                                                    75
```

<210> SEQ ID NO 48
<211> LENGTH: 75
<212> TYPE: DNA
<213> ORGANISM: Artificial Sequence
<220> FEATURE:
<223> OTHER INFORMATION: synthesized-Primer-9AH3702

```
<220> FEATURE:
<221> NAME/KEY: variation
<222> LOCATION: 34,46
<223> OTHER INFORMATION: /note="n is A, T, C or G"

<400> SEQUENCE: 48
cgtgcggaag acacagcggt gtattattgc gcgnggthyk ggthynayta ttgggggcag    60
ggcacccttg ttacc                                                    75

<210> SEQ ID NO 49
<211> LENGTH: 75
<212> TYPE: DNA
<213> ORGANISM: Artificial Sequence
<220> FEATURE:
<223> OTHER INFORMATION: synthesized-Primer-9AH3703
<220> FEATURE:
<221> NAME/KEY: variation
<222> LOCATION: 34,46
<223> OTHER INFORMATION: /note="n is A, T, C or G"

<400> SEQUENCE: 49
cgtgcggaag acacagcggt gtattattgc gcgnggthyt hykggnayta ttgggggcag    60
ggcacccttg ttacc                                                    75

<210> SEQ ID NO 50
<211> LENGTH: 75
<212> TYPE: DNA
<213> ORGANISM: Artificial Sequence
<220> FEATURE:
<223> OTHER INFORMATION: synthesized-Primer-9AH3704
<220> FEATURE:
<221> NAME/KEY: variation
<222> LOCATION: 40,43,45
<223> OTHER INFORMATION: /note="n is A, T, C or G"

<400> SEQUENCE: 50
cgtgcggaag acacagcggt gtattattgc gcgcgtgggn wyntngatta ttgggggcag    60
ggcacccttg ttacc                                                    75

<210> SEQ ID NO 51
<211> LENGTH: 75
<212> TYPE: DNA
<213> ORGANISM: Artificial Sequence
<220> FEATURE:
<223> OTHER INFORMATION: synthesized-Primer-9AH3705
<220> FEATURE:
<221> NAME/KEY: variation
<222> LOCATION: 43,45
<223> OTHER INFORMATION: /note="n is A, T, C or G"

<400> SEQUENCE: 51
cgtgcggaag acacagcggt gtattattgc gcgcgtgggk ggntngatta ttgggggcag    60
ggcacccttg ttacc                                                    75

<210> SEQ ID NO 52
<211> LENGTH: 15
<212> TYPE: DNA
<213> ORGANISM: Artificial Sequence
<220> FEATURE:
<223> OTHER INFORMATION: synthesized-9AH3701
<220> FEATURE:
<221> NAME/KEY: variation
<222> LOCATION: 1,13
<223> OTHER INFORMATION: /note="n is A, T, C or G"

<400> SEQUENCE: 52
```
nggkggthyt hynay                                            15

<210> SEQ ID NO 53
<211> LENGTH: 15
<212> TYPE: DNA
<213> ORGANISM: Artificial Sequence
<220> FEATURE:
<223> OTHER INFORMATION: synthesized-9AH3702
<220> FEATURE:
<221> NAME/KEY: variation
<222> LOCATION: 1,13
<223> OTHER INFORMATION: /note="n is A, T, C or G"

<400> SEQUENCE: 53
nggthykggt hynay                                            15

<210> SEQ ID NO 54
<211> LENGTH: 15
<212> TYPE: DNA
<213> ORGANISM: Artificial Sequence
<220> FEATURE:
<223> OTHER INFORMATION: synthesized-9AH3703
<220> FEATURE:
<221> NAME/KEY: variation
<222> LOCATION: 1,13
<223> OTHER INFORMATION: /note="n is A, T, C or G"

<400> SEQUENCE: 54
nggthythyk ggnay                                            15

<210> SEQ ID NO 55
<211> LENGTH: 12
<212> TYPE: DNA
<213> ORGANISM: Artificial Sequence
<220> FEATURE:
<223> OTHER INFORMATION: synthesized-9AH3704
<220> FEATURE:
<221> NAME/KEY: variation
<222> LOCATION: 4,7,9
<223> OTHER INFORMATION: /note="n is A, T, C or G"

<400> SEQUENCE: 55
gggnwyntng at                                               12

<210> SEQ ID NO 56
<211> LENGTH: 12
<212> TYPE: DNA
<213> ORGANISM: Artificial Sequence
<220> FEATURE:
<223> OTHER INFORMATION: synthesized-9AH3705
<220> FEATURE:
<221> NAME/KEY: variation
<222> LOCATION: 7,9
<223> OTHER INFORMATION: /note="n is A, T, C or G"

<400> SEQUENCE: 56
gggkggntng at                                               12

<210> SEQ ID NO 57
<211> LENGTH: 78
<212> TYPE: DNA
<213> ORGANISM: Artificial Sequence
<220> FEATURE:
<223> OTHER INFORMATION: synthesized-Primer-9AH3801
<220> FEATURE:
<221> NAME/KEY: variation
<222> LOCATION: 40,43,46,48
<223> OTHER INFORMATION: /note="n is A, T, C or G"

<400> SEQUENCE: 57
cgtgcggaag acacagcggt gtattattgc gcgcgtgggn wynwyntnga ttattggggg    60
cagggcaccc ttgttacc                                                 78

<210> SEQ ID NO 58
<211> LENGTH: 78
<212> TYPE: DNA
<213> ORGANISM: Artificial Sequence
<220> FEATURE:
<223> OTHER INFORMATION: synthesized-Primer-9AH3802
<220> FEATURE:
<221> NAME/KEY: variation
<222> LOCATION: 40,46,48
<223> OTHER INFORMATION: /note="n is A, T, C or G"

<400> SEQUENCE: 58
cgtgcggaag acacagcggt gtattattgc gcgcgtgggn wykggntnga ttattggggg    60
cagggcaccc ttgttacc                                                 78

<210> SEQ ID NO 59
<211> LENGTH: 78
<212> TYPE: DNA
<213> ORGANISM: Artificial Sequence
<220> FEATURE:
<223> OTHER INFORMATION: synthesized-Primer-9AH3803
<220> FEATURE:
<221> NAME/KEY: variation
<222> LOCATION: 43,46,48
<223> OTHER INFORMATION: /note="n is A, T, C or G"

<400> SEQUENCE: 59
cgtgcggaag acacagcggt gtattattgc gcgcgtgggk ggnwyntnga ttattggggg    60
cagggcaccc ttgttacc                                                 78

<210> SEQ ID NO 60
<211> LENGTH: 12
<212> TYPE: DNA
<213> ORGANISM: Artificial Sequence
<220> FEATURE:
<223> OTHER INFORMATION: synthesized-9AH3801
<220> FEATURE:
<221> NAME/KEY: variation
<222> LOCATION: 4,7,10,12
<223> OTHER INFORMATION: /note="n is A, T, C or G"

<400> SEQUENCE: 60
gggnwynwyn tn                                                       12

<210> SEQ ID NO 61
<211> LENGTH: 12
<212> TYPE: DNA
<213> ORGANISM: Artificial Sequence
<220> FEATURE:
<223> OTHER INFORMATION: synthesized-9AH3802
<220> FEATURE:
<221> NAME/KEY: variation
<222> LOCATION: 4,10,12
<223> OTHER INFORMATION: /note="n is A, T, C or G"

<400> SEQUENCE: 61
gggnwykggn tn                                                       12

<210> SEQ ID NO 62
<211> LENGTH: 12
<212> TYPE: DNA
<213> ORGANISM: Artificial Sequence
<220> FEATURE:

<223> OTHER INFORMATION: synthesized-9AH3803
<220> FEATURE:
<221> NAME/KEY: variation
<222> LOCATION: 7,10,12
<223> OTHER INFORMATION: /note="n is A, T, C or G"

<400> SEQUENCE: 62
gggkggnwyn tn                                                      12

<210> SEQ ID NO 63
<211> LENGTH: 81
<212> TYPE: DNA
<213> ORGANISM: Artificial Sequence
<220> FEATURE:
<223> OTHER INFORMATION: synthesized-Primer-9AH3901
<220> FEATURE:
<221> NAME/KEY: variation
<222> LOCATION: 40,43,46,49,51
<223> OTHER INFORMATION: /note="n is A, T, C or G"

<400> SEQUENCE: 63
cgtgcggaag acacagcggt gtattattgc gcgcgtgggn wynwynwynt ngattattgg      60
gggcagggca cccttgttac c                                               81

<210> SEQ ID NO 64
<211> LENGTH: 81
<212> TYPE: DNA
<213> ORGANISM: Artificial Sequence
<220> FEATURE:
<223> OTHER INFORMATION: synthesized-Primer-9AH3902
<220> FEATURE:
<221> NAME/KEY: variation
<222> LOCATION: 40,43,49,51
<223> OTHER INFORMATION: /note="n is A, T, C or G"

<400> SEQUENCE: 64
cgtgcggaag acacagcggt gtattattgc gcgcgtgggn wynwykggnt ngattattgg      60
gggcagggca cccttgttac c                                               81

<210> SEQ ID NO 65
<211> LENGTH: 81
<212> TYPE: DNA
<213> ORGANISM: Artificial Sequence
<220> FEATURE:
<223> OTHER INFORMATION: synthesized-Primer-9AH3903
<220> FEATURE:
<221> NAME/KEY: variation
<222> LOCATION: 40,46,49,51
<223> OTHER INFORMATION: /note="n is A, T, C or G"

<400> SEQUENCE: 65
cgtgcggaag acacagcggt gtattattgc gcgcgtgggn wykggnwynt ngattattgg      60
gggcagggca cccttgttac c                                               81

<210> SEQ ID NO 66
<211> LENGTH: 81
<212> TYPE: DNA
<213> ORGANISM: Artificial Sequence
<220> FEATURE:
<223> OTHER INFORMATION: synthesized-Primer-9AH3904
<220> FEATURE:
<221> NAME/KEY: variation
<222> LOCATION: 43,46,49,51
<223> OTHER INFORMATION: /note="n is A, T, C or G"

<400> SEQUENCE: 66
cgtgcggaag acacagcggt gtattattgc gcgcgtgggk ggnwynwynt ngattattgg      60
gggcagggca cccttgttac c                                              81

<210> SEQ ID NO 67
<211> LENGTH: 15
<212> TYPE: DNA
<213> ORGANISM: Artificial Sequence
<220> FEATURE:
<223> OTHER INFORMATION: synthesized-9AH3901
<220> FEATURE:
<221> NAME/KEY: variation
<222> LOCATION: 4,7,10,13,15
<223> OTHER INFORMATION: /note="n is A, T, C or G"

<400> SEQUENCE: 67
gggnwynwyn wyntn                                                     15

<210> SEQ ID NO 68
<211> LENGTH: 15
<212> TYPE: DNA
<213> ORGANISM: Artificial Sequence
<220> FEATURE:
<223> OTHER INFORMATION: synthesized-9AH3902
<220> FEATURE:
<221> NAME/KEY: variation
<222> LOCATION: 4,7,13,15
<223> OTHER INFORMATION: /note="n is A, T, C or G"

<400> SEQUENCE: 68
gggnwynwyk ggntn                                                     15

<210> SEQ ID NO 69
<211> LENGTH: 15
<212> TYPE: DNA
<213> ORGANISM: Artificial Sequence
<220> FEATURE:
<223> OTHER INFORMATION: synthesized-9AH3903
<220> FEATURE:
<221> NAME/KEY: variation
<222> LOCATION: 4,10,13,15
<223> OTHER INFORMATION: /note="n is A, T, C or G"

<400> SEQUENCE: 69
gggnwykggn wyntn                                                     15

<210> SEQ ID NO 70
<211> LENGTH: 15
<212> TYPE: DNA
<213> ORGANISM: Artificial Sequence
<220> FEATURE:
<223> OTHER INFORMATION: synthesized-9AH3904
<220> FEATURE:
<221> NAME/KEY: variation
<222> LOCATION: 7,10,13,15
<223> OTHER INFORMATION: /note="n is A, T, C or G"

<400> SEQUENCE: 70
gggkggnwyn wyntn                                                     15

<210> SEQ ID NO 71
<211> LENGTH: 84
<212> TYPE: DNA
<213> ORGANISM: Artificial Sequence
<220> FEATURE:
<223> OTHER INFORMATION: synthesized-Primer-9AH31001
<220> FEATURE:
<221> NAME/KEY: variation
<222> LOCATION: 40,43,46,49,52,54
<223> OTHER INFORMATION: /note="n is A, T, C or G"

<400> SEQUENCE: 71
cgtgcggaag acacagcggt gtattattgc gcgcgtgggn wynwynwynw yntngattat    60 tggggggcagg gcacccttgt tacc                                          84

<210> SEQ ID NO 72
<211> LENGTH: 84
<212> TYPE: DNA
<213> ORGANISM: Artificial Sequence
<220> FEATURE:
<223> OTHER INFORMATION: synthesized-Primer-9AH31002
<220> FEATURE:
<221> NAME/KEY: variation
<222> LOCATION: 40,43,46,52,54
<223> OTHER INFORMATION: /note="n is A, T, C or G"

<400> SEQUENCE: 72
cgtgcggaag acacagcggt gtattattgc gcgcgtgggn wynwynwykg gntngattat    60 tggggggcagg gcacccttgt tacc                                          84

<210> SEQ ID NO 73
<211> LENGTH: 84
<212> TYPE: DNA
<213> ORGANISM: Artificial Sequence
<220> FEATURE:
<223> OTHER INFORMATION: synthesized-Primer-9AH31003
<220> FEATURE:
<221> NAME/KEY: V_region
<222> LOCATION: 40,43,49,52,54
<223> OTHER INFORMATION: /note="n is A, T, C or G"

<400> SEQUENCE: 73
cgtgcggaag acacagcggt gtattattgc gcgcgtgggn wynwykggnw yntngattat    60 tggggggcagg gcacccttgt tacc                                          84

<210> SEQ ID NO 74
<211> LENGTH: 84
<212> TYPE: DNA
<213> ORGANISM: Artificial Sequence
<220> FEATURE:
<223> OTHER INFORMATION: synthesized-Primer-9AH31004
<220> FEATURE:
<221> NAME/KEY: variation
<222> LOCATION: 40,46,49,52,54
<223> OTHER INFORMATION: /note="n is A, T, C or G"

<400> SEQUENCE: 74
cgtgcggaag acacagcggt gtattattgc gcgcgtgggn wykggnwynw yntngattat    60 tggggggcagg gcacccttgt tacc                                          84

<210> SEQ ID NO 75
<211> LENGTH: 84
<212> TYPE: DNA
<213> ORGANISM: Artificial Sequence
<220> FEATURE:
<223> OTHER INFORMATION: synthesized-Primer-9AH31005
<220> FEATURE:
<221> NAME/KEY: variation
<222> LOCATION: 43,46,49,52,54
<223> OTHER INFORMATION: /note="n is A, T, C or G"

<400> SEQUENCE: 75
cgtgcggaag acacagcggt gtattattgc gcgcgtgggk ggnwynwynw yntngattat    60 tggggggcagg gcacccttgt tacc                                          84

```
<210> SEQ ID NO 76
<211> LENGTH: 18
<212> TYPE: DNA
<213> ORGANISM: Artificial Sequence
<220> FEATURE:
<223> OTHER INFORMATION: synthesized-9AH31001
<220> FEATURE:
<221> NAME/KEY: variation
<222> LOCATION: 4,7,10,13,16,18
<223> OTHER INFORMATION: /note="n is A, T, C or G"

<400> SEQUENCE: 76
gggnwynwyn wynwyntn                                               18

<210> SEQ ID NO 77
<211> LENGTH: 18
<212> TYPE: DNA
<213> ORGANISM: Artificial Sequence
<220> FEATURE:
<223> OTHER INFORMATION: synthesized-9AH31002
<220> FEATURE:
<221> NAME/KEY: variation
<222> LOCATION: 4,7,10,16,18
<223> OTHER INFORMATION: /note="n is A, T, C or G"

<400> SEQUENCE: 77
gggnwynwyn wykggntn                                               18

<210> SEQ ID NO 78
<211> LENGTH: 18
<212> TYPE: DNA
<213> ORGANISM: Artificial Sequence
<220> FEATURE:
<223> OTHER INFORMATION: synthesized-9AH31003
<220> FEATURE:
<221> NAME/KEY: variation
<222> LOCATION: 4,7,13,16,18
<223> OTHER INFORMATION: /note="n is A, T, C or G"

<400> SEQUENCE: 78
gggnwynwyk ggnwyntn                                               18

<210> SEQ ID NO 79
<211> LENGTH: 18
<212> TYPE: DNA
<213> ORGANISM: Artificial Sequence
<220> FEATURE:
<223> OTHER INFORMATION: synthesized-9AH31004
<220> FEATURE:
<221> NAME/KEY: variation
<222> LOCATION: 4,10,13,16,18
<223> OTHER INFORMATION: /note="n is A, T, C or G"

<400> SEQUENCE: 79
gggnwykggn wynwyntn                                               18

<210> SEQ ID NO 80
<211> LENGTH: 18
<212> TYPE: DNA
<213> ORGANISM: Artificial Sequence
<220> FEATURE:
<223> OTHER INFORMATION: synthesized-9AH31005
<220> FEATURE:
<221> NAME/KEY: variation
<222> LOCATION: 7,10,13,16,18
<223> OTHER INFORMATION: /note="n is A, T, C or G"

<400> SEQUENCE: 80
gggkggnwyn wynwynt

<210> SEQ ID NO 81
<211> LENGTH: 87
<212> TYPE: DNA
<213> ORGANISM: Artificial Sequence
<220> FEATURE:
<223> OTHER INFORMATION: synthesized-Primer-9AH31101
<220> FEATURE:
<221> NAME/KEY: variation
<222> LOCATION: 55,57
<223> OTHER INFORMATION: /note="n is A, T, C or G"

<400> SEQUENCE: 81
cgtgcggaag acacagcggt gtattattgc gcgcgtgggb wybwybwykg gkggntngat      60
tattgggggc agggcaccct tgttacc                                         87

<210> SEQ ID NO 82
<211> LENGTH: 87
<212> TYPE: DNA
<213> ORGANISM: Artificial Sequence
<220> FEATURE:
<223> OTHER INFORMATION: synthesized-Primer-9AH31102
<220> FEATURE:
<221> NAME/KEY: variation
<222> LOCATION: 55,57
<223> OTHER INFORMATION: /note="n is A, T, C or G"

<400> SEQUENCE: 82
cgtgcggaag acacagcggt gtattattgc gcgcgtgggb wybwykggbw ykggntngat      60
tattgggggc agggcaccct tgttacc                                         87

<210> SEQ ID NO 83
<211> LENGTH: 87
<212> TYPE: DNA
<213> ORGANISM: Artificial Sequence
<220> FEATURE:
<223> OTHER INFORMATION: synthesized-Primer-9AH31103
<220> FEATURE:
<221> NAME/KEY: variation
<222> LOCATION: 55,57
<223> OTHER INFORMATION: /note="n is A, T, C or G"

<400> SEQUENCE: 83
cgtgcggaag acacagcggt gtattattgc gcgcgtgggb wykggbwybw ykggntngat      60
tattgggggc agggcaccct tgttacc                                         87

<210> SEQ ID NO 84
<211> LENGTH: 87
<212> TYPE: DNA
<213> ORGANISM: Artificial Sequence
<220> FEATURE:
<223> OTHER INFORMATION: synthesized-Primer-9AH31104
<220> FEATURE:
<221> NAME/KEY: variation
<222> LOCATION: 55,57
<223> OTHER INFORMATION: /note="n is A, T, C or G"

<400> SEQUENCE: 84
cgtgcggaag acacagcggt gtattattgc gcgcgtgggk ggbwybwybw ykggntngat      60
tattgggggc agggcaccct tgttacc                                         87

<210> SEQ ID NO 85
<211> LENGTH: 87
<212> TYPE: DNA
<213> ORGANISM: Artificial Sequence
<220> FEATURE:
<223> OTHER INFORMATION: synthesized-Primer-9AH31105

```
<220> FEATURE:
<221> NAME/KEY: variation
<222> LOCATION: 55,57
<223> OTHER INFORMATION: /note="n is A, T, C or G"

<400> SEQUENCE: 85
cgtgcggaag acacagcggt gtattattgc gcgcgtgggb wybwykggkg gbwyntngat      60 tattggggc agggcaccct tgttacc                                           87

<210> SEQ ID NO 86
<211> LENGTH: 87
<212> TYPE: DNA
<213> ORGANISM: Artificial Sequence
<220> FEATURE:
<223> OTHER INFORMATION: synthesized-Primer-9AH31106
<220> FEATURE:
<221> NAME/KEY: variation
<222> LOCATION: 55,57
<223> OTHER INFORMATION: /note="n is A, T, C or G"

<400> SEQUENCE: 86
cgtgcggaag acacagcggt gtattattgc gcgcgtgggb wykggbwykg gbwyntngat      60 tattggggc agggcaccct tgttacc                                           87

<210> SEQ ID NO 87
<211> LENGTH: 87
<212> TYPE: DNA
<213> ORGANISM: Artificial Sequence
<220> FEATURE:
<223> OTHER INFORMATION: synthesized-Primer-9AH31107
<220> FEATURE:
<221> NAME/KEY: variation
<222> LOCATION: 55,57
<223> OTHER INFORMATION: /note="n is A, T, C or G"

<400> SEQUENCE: 87
cgtgcggaag acacagcggt gtattattgc gcgcgtgggk ggbwybwykg gbwyntngat      60 tattggggc agggcaccct tgttacc                                           87

<210> SEQ ID NO 88
<211> LENGTH: 87
<212> TYPE: DNA
<213> ORGANISM: Artificial Sequence
<220> FEATURE:
<223> OTHER INFORMATION: synthesized-Primer-9AH31108
<220> FEATURE:
<221> NAME/KEY: variation
<222> LOCATION: 55,57
<223> OTHER INFORMATION: /note="n is A, T, C or G"

<400> SEQUENCE: 88
cgtgcggaag acacagcggt gtattattgc gcgcgtgggb wykggkggbw ybwyntngat      60 tattggggc agggcaccct tgttacc                                           87

<210> SEQ ID NO 89
<211> LENGTH: 87
<212> TYPE: DNA
<213> ORGANISM: Artificial Sequence
<220> FEATURE:
<223> OTHER INFORMATION: synthesized-Primer-9AH31109
<220> FEATURE:
<221> NAME/KEY: variation
<222> LOCATION: 55,57
<223> OTHER INFORMATION: /note="n is A, T, C or G"

<400> SEQUENCE: 89
```
cgtgcggaag acacagcggt gtattattgc gcgcgtgggk ggbwykggbw ybwyntngat    60
tattgggggc agggcaccct tgttacc                                       87

<210> SEQ ID NO 90
<211> LENGTH: 87
<212> TYPE: DNA
<213> ORGANISM: Artificial Sequence
<220> FEATURE:
<223> OTHER INFORMATION: synthesized-Primer-9AH31110
<220> FEATURE:
<221> NAME/KEY: variation
<222> LOCATION: 55,57
<223> OTHER INFORMATION: /note="n is A, T, C or G"

<400> SEQUENCE: 90
cgtgcggaag acacagcggt gtattattgc gcgcgtgggk ggkggbwybw ybwyntngat    60
tattgggggc agggcaccct tgttacc                                       87

<210> SEQ ID NO 91
<211> LENGTH: 21
<212> TYPE: DNA
<213> ORGANISM: Artificial Sequence
<220> FEATURE:
<223> OTHER INFORMATION: synthesized-9AH31101
<220> FEATURE:
<221> NAME/KEY: variation
<222> LOCATION: 19,21
<223> OTHER INFORMATION: /note="n is A, T, C or G"

<400> SEQUENCE: 91
gggbwybwyb wykggkggnt n                                             21

<210> SEQ ID NO 92
<211> LENGTH: 21
<212> TYPE: DNA
<213> ORGANISM: Artificial Sequence
<220> FEATURE:
<223> OTHER INFORMATION: synthesized-9AH31102
<220> FEATURE:
<221> NAME/KEY: variation
<222> LOCATION: 19,21
<223> OTHER INFORMATION: /note="n is A, T, C or G"

<400> SEQUENCE: 92
gggbwybwyk ggbwykggnt n                                             21

<210> SEQ ID NO 93
<211> LENGTH: 21
<212> TYPE: DNA
<213> ORGANISM: Artificial Sequence
<220> FEATURE:
<223> OTHER INFORMATION: synthesized-9AH31103
<220> FEATURE:
<221> NAME/KEY: variation
<222> LOCATION: 19,21
<223> OTHER INFORMATION: /note="n is A, T, C or G"

<400> SEQUENCE: 93
gggbwykggb wybwykggnt n                                             21

<210> SEQ ID NO 94
<211> LENGTH: 21
<212> TYPE: DNA
<213> ORGANISM: Artificial Sequence
<220> FEATURE:
<223> OTHER INFORMATION: synthesized-9AH31104
<220> FEATURE:
<221> NAME/KEY: variation
<222> LOCATION: 19,21
<223> OTHER INFORMATION: /note="n is A, T, C or G"

<400> SEQUENCE: 94
gggkggbwyb wybwykggnt n                                              21

<210> SEQ ID NO 95
<211> LENGTH: 21
<212> TYPE: DNA
<213> ORGANISM: Artificial Sequence
<220> FEATURE:
<223> OTHER INFORMATION: synthesized-9AH31105
<220> FEATURE:
<221> NAME/KEY: variation
<222> LOCATION: 19,21
<223> OTHER INFORMATION: /note="n is A, T, C or G"

<400> SEQUENCE: 95
gggbwybwyk ggkggbwynt n                                              21

<210> SEQ ID NO 96
<211> LENGTH: 21
<212> TYPE: DNA
<213> ORGANISM: Artificial Sequence
<220> FEATURE:
<223> OTHER INFORMATION: synthesized-9AH31106
<220> FEATURE:
<221> NAME/KEY: variation
<222> LOCATION: 19,21
<223> OTHER INFORMATION: /note="n is A, T, C or G"

<400> SEQUENCE: 96
gggbwykggb wykggbwynt n                                              21

<210> SEQ ID NO 97
<211> LENGTH: 21
<212> TYPE: DNA
<213> ORGANISM: Artificial Sequence
<220> FEATURE:
<223> OTHER INFORMATION: synthesized-9AH31107
<220> FEATURE:
<221> NAME/KEY: variation
<222> LOCATION: 19,21
<223> OTHER INFORMATION: /note="n is A, T, C or G"

<400> SEQUENCE: 97
gggkggbwyb wykggbwynt n                                              21

<210> SEQ ID NO 98
<211> LENGTH: 21
<212> TYPE: DNA
<213> ORGANISM: Artificial Sequence
<220> FEATURE:
<223> OTHER INFORMATION: synthesized-9AH31108
<220> FEATURE:
<221> NAME/KEY: variation
<222> LOCATION: 19,21
<223> OTHER INFORMATION: /note="n is A, T, C or G"

<400> SEQUENCE: 98
gggbwykggk ggbwybwynt n                                              21

<210> SEQ ID NO 99
<211> LENGTH: 21
<212> TYPE: DNA
<213> ORGANISM: Artificial Sequence
<220> FEATURE:
<223> OTHER INFORMATION: synthesized-9AH31109
<220> FEATURE:

```
<221> NAME/KEY: variation
<222> LOCATION: 19,21
<223> OTHER INFORMATION: /note="n is A, T, C or G"

<400> SEQUENCE: 99
gggkggbwyk ggbwybwynt n                                            21

<210> SEQ ID NO 100
<211> LENGTH: 21
<212> TYPE: DNA
<213> ORGANISM: Artificial Sequence
<220> FEATURE:
<223> OTHER INFORMATION: synthesized-9AH31110
<220> FEATURE:
<221> NAME/KEY: variation
<222> LOCATION: 19,21
<223> OTHER INFORMATION: /note="n is A, T, C or G"

<400> SEQUENCE: 100
gggkggkggb wybwybwynt n                                            21

<210> SEQ ID NO 101
<211> LENGTH: 90
<212> TYPE: DNA
<213> ORGANISM: Artificial Sequence
<220> FEATURE:
<223> OTHER INFORMATION: synthesized-Primer-9AH31201

<400> SEQUENCE: 101
cgtgcggaag acacagcggt gtattattgc gcgcgtgggb wybwybwybw ykggkggatg    60
gattattggg ggcagggcac ccttgttacc                                    90

<210> SEQ ID NO 102
<211> LENGTH: 90
<212> TYPE: DNA
<213> ORGANISM: Artificial Sequence
<220> FEATURE:
<223> OTHER INFORMATION: synthesized-Primer-9AH31202

<400> SEQUENCE: 102
cgtgcggaag acacagcggt gtattattgc gcgcgtgggb wybwybwykg gbwykggatg    60
gattattggg ggcagggcac ccttgttacc                                    90

<210> SEQ ID NO 103
<211> LENGTH: 90
<212> TYPE: DNA
<213> ORGANISM: Artificial Sequence
<220> FEATURE:
<223> OTHER INFORMATION: synthesized-Primer-9AH31203

<400> SEQUENCE: 103
cgtgcggaag acacagcggt gtattattgc gcgcgtgggb wybwykggbw ybwykggatg    60
gattattggg ggcagggcac ccttgttacc                                    90

<210> SEQ ID NO 104
<211> LENGTH: 90
<212> TYPE: DNA
<213> ORGANISM: Artificial Sequence
<220> FEATURE:
<223> OTHER INFORMATION: synthesized-Primer-9AH31204

<400> SEQUENCE: 104
cgtgcggaag acacagcggt gtattattgc gcgcgtgggb wykggbwybw ybwykggatg    60
gattattggg ggcagggcac ccttgttacc                                    90
```

<210> SEQ ID NO 105
<211> LENGTH: 90
<212> TYPE: DNA
<213> ORGANISM: Artificial Sequence
<220> FEATURE:
<223> OTHER INFORMATION: synthesized-Primer-9AH31205

<400> SEQUENCE: 105
cgtgcggaag acacagcggt gtattattgc gcgcgtgggk ggbwybwybw ybwykggatg    60
gattattggg ggcagggcac ccttgttacc    90

<210> SEQ ID NO 106
<211> LENGTH: 90
<212> TYPE: DNA
<213> ORGANISM: Artificial Sequence
<220> FEATURE:
<223> OTHER INFORMATION: synthesized-Primer-9AH31206

<400> SEQUENCE: 106
cgtgcggaag acacagcggt gtattattgc gcgcgtgggb wybwybwykg gkggbwyatg    60
gattattggg ggcagggcac ccttgttacc    90

<210> SEQ ID NO 107
<211> LENGTH: 90
<212> TYPE: DNA
<213> ORGANISM: Artificial Sequence
<220> FEATURE:
<223> OTHER INFORMATION: synthesized-Primer-9AH31207

<400> SEQUENCE: 107
cgtgcggaag acacagcggt gtattattgc gcgcgtgggb wybwykggbw ykggbwyatg    60
gattattggg ggcagggcac ccttgttacc    90

<210> SEQ ID NO 108
<211> LENGTH: 90
<212> TYPE: DNA
<213> ORGANISM: Artificial Sequence
<220> FEATURE:
<223> OTHER INFORMATION: synthesized-Primer-9AH31208

<400> SEQUENCE: 108
cgtgcggaag acacagcggt gtattattgc gcgcgtgggb wykggbwybw ykggbwyatg    60
gattattggg ggcagggcac ccttgttacc    90

<210> SEQ ID NO 109
<211> LENGTH: 90
<212> TYPE: DNA
<213> ORGANISM: Artificial Sequence
<220> FEATURE:
<223> OTHER INFORMATION: synthesized-Primer-9AH31209

<400> SEQUENCE: 109
cgtgcggaag acacagcggt gtattattgc gcgcgtgggk ggbwybwybw ykggbwyatg    60
gattattggg ggcagggcac ccttgttacc    90

<210> SEQ ID NO 110
<211> LENGTH: 90
<212> TYPE: DNA
<213> ORGANISM: Artificial Sequence
<220> FEATURE:
<223> OTHER INFORMATION: synthesized-Primer-9AH31210

```
<400> SEQUENCE: 110
cgtgcggaag acacagcggt gtattattgc gcgcgtgggb wybwykggkg gbwybwyatg    60
gattattggg ggcagggcac ccttgttacc                                    90

<210> SEQ ID NO 111
<211> LENGTH: 90
<212> TYPE: DNA
<213> ORGANISM: Artificial Sequence
<220> FEATURE:
<223> OTHER INFORMATION: synthesized-Primer-9AH31211

<400> SEQUENCE: 111
cgtgcggaag acacagcggt gtattattgc gcgcgtgggb wykggbwykg gbwybwyatg    60
gattattggg ggcagggcac ccttgttacc                                    90

<210> SEQ ID NO 112
<211> LENGTH: 90
<212> TYPE: DNA
<213> ORGANISM: Artificial Sequence
<220> FEATURE:
<223> OTHER INFORMATION: synthesized-Primer-9AH31212

<400> SEQUENCE: 112
cgtgcggaag acacagcggt gtattattgc gcgcgtgggk ggbwybwykg gbwybwyatg    60
gattattggg ggcagggcac ccttgttacc                                    90

<210> SEQ ID NO 113
<211> LENGTH: 90
<212> TYPE: DNA
<213> ORGANISM: Artificial Sequence
<220> FEATURE:
<223> OTHER INFORMATION: synthesized-Primer-9AH31213

<400> SEQUENCE: 113
cgtgcggaag acacagcggt gtattattgc gcgcgtgggb wykggkggbw ybwybwyatg    60
gattattggg ggcagggcac ccttgttacc                                    90

<210> SEQ ID NO 114
<211> LENGTH: 90
<212> TYPE: DNA
<213> ORGANISM: Artificial Sequence
<220> FEATURE:
<223> OTHER INFORMATION: synthesized-Primer-9AH31214

<400> SEQUENCE: 114
cgtgcggaag acacagcggt gtattattgc gcgcgtgggk ggbwykggbw ybwybwyatg    60
gattattggg ggcagggcac ccttgttacc                                    90

<210> SEQ ID NO 115
<211> LENGTH: 90
<212> TYPE: DNA
<213> ORGANISM: Artificial Sequence
<220> FEATURE:
<223> OTHER INFORMATION: synthesized-Primer-9AH31215

<400> SEQUENCE: 115
cgtgcggaag acacagcggt gtattattgc gcgcgtgggk ggkggbwybw ybwybwyatg    60
gattattggg ggcagggcac ccttgttacc                                    90

<210> SEQ ID NO 116
<211> LENGTH: 21
```

<212> TYPE: DNA
<213> ORGANISM: Artificial Sequence
<220> FEATURE:
<223> OTHER INFORMATION: synthesized-9AH31201

<400> SEQUENCE: 116
gggbwybwyb wybwykggkg g					21

<210> SEQ ID NO 117
<211> LENGTH: 21
<212> TYPE: DNA
<213> ORGANISM: Artificial Sequence
<220> FEATURE:
<223> OTHER INFORMATION: synthesized-9AH31202

<400> SEQUENCE: 117
gggbwybwyb wykggbwykg g					21

<210> SEQ ID NO 118
<211> LENGTH: 21
<212> TYPE: DNA
<213> ORGANISM: Artificial Sequence
<220> FEATURE:
<223> OTHER INFORMATION: synthesized-9AH31203

<400> SEQUENCE: 118
gggbwybwyk ggbwybwykg g					21

<210> SEQ ID NO 119
<211> LENGTH: 21
<212> TYPE: DNA
<213> ORGANISM: Artificial Sequence
<220> FEATURE:
<223> OTHER INFORMATION: synthesized-9AH31204

<400> SEQUENCE: 119
gggbwykggb wybwybwykg g					21

<210> SEQ ID NO 120
<211> LENGTH: 21
<212> TYPE: DNA
<213> ORGANISM: Artificial Sequence
<220> FEATURE:
<223> OTHER INFORMATION: synthesized-9AH31205

<400> SEQUENCE: 120
gggkggbwyb wybwybwykg g					21

<210> SEQ ID NO 121
<211> LENGTH: 21
<212> TYPE: DNA
<213> ORGANISM: Artificial Sequence
<220> FEATURE:
<223> OTHER INFORMATION: synthesized-9AH31206

<400> SEQUENCE: 121
gggbwybwyb wykggkggbw y					21

<210> SEQ ID NO 122
<211> LENGTH: 21
<212> TYPE: DNA
<213> ORGANISM: Artificial Sequence
<220> FEATURE:
<223> OTHER INFORMATION: synthesized-9AH31207

<400> SEQUENCE: 122
gggbwybwyk ggbwykggbw y                                              21

<210> SEQ ID NO 123
<211> LENGTH: 21
<212> TYPE: DNA
<213> ORGANISM: Artificial Sequence
<220> FEATURE:
<223> OTHER INFORMATION: synthesized-9AH31208

<400> SEQUENCE: 123
gggbwykggb wybwykggbw y                                              21

<210> SEQ ID NO 124
<211> LENGTH: 21
<212> TYPE: DNA
<213> ORGANISM: Artificial Sequence
<220> FEATURE:
<223> OTHER INFORMATION: synthesized-9AH31209

<400> SEQUENCE: 124
gggkggbwyb wybwykggbw y                                              21

<210> SEQ ID NO 125
<211> LENGTH: 21
<212> TYPE: DNA
<213> ORGANISM: Artificial Sequence
<220> FEATURE:
<223> OTHER INFORMATION: synthesized-9AH31210

<400> SEQUENCE: 125
gggbwybwyk ggkggbwybw y                                              21

<210> SEQ ID NO 126
<211> LENGTH: 21
<212> TYPE: DNA
<213> ORGANISM: Artificial Sequence
<220> FEATURE:
<223> OTHER INFORMATION: synthesized-9AH31211

<400> SEQUENCE: 126
gggbwykggb wykggbwybw y                                              21

<210> SEQ ID NO 127
<211> LENGTH: 21
<212> TYPE: DNA
<213> ORGANISM: Artificial Sequence
<220> FEATURE:
<223> OTHER INFORMATION: synthesized-9AH31212

<400> SEQUENCE: 127
gggkggbwyb wykggbwybw y                                              21

<210> SEQ ID NO 128
<211> LENGTH: 21
<212> TYPE: DNA
<213> ORGANISM: Artificial Sequence
<220> FEATURE:
<223> OTHER INFORMATION: synthesized-9AH31213

<400> SEQUENCE: 128
gggbwykggk ggbwybwybw y                                              21

<210> SEQ ID NO 129
<211> LENGTH: 21
<212> TYPE: DNA
<213> ORGANISM: Artificial Sequence -continued

```
<220> FEATURE:
<223> OTHER INFORMATION: synthesized-9AH31214

<400> SEQUENCE: 129
gggkggbwyk ggbwybwybw y                                        21

<210> SEQ ID NO 130
<211> LENGTH: 21
<212> TYPE: DNA
<213> ORGANISM: Artificial Sequence
<220> FEATURE:
<223> OTHER INFORMATION: synthesized-9AH31215

<400> SEQUENCE: 130
gggkggkggb wybwybwybw y                                        21

<210> SEQ ID NO 131
<211> LENGTH: 93
<212> TYPE: DNA
<213> ORGANISM: Artificial Sequence
<220> FEATURE:
<223> OTHER INFORMATION: synthesized-Primer-9AH31301

<400> SEQUENCE: 131
cgtgcggaag acacagcggt gtattattgc gcgcgtgggb wybwybwybw ybwykggkgg      60
atggattatt gggggcaggg cacccttgtt acc                                  93

<210> SEQ ID NO 132
<211> LENGTH: 93
<212> TYPE: DNA
<213> ORGANISM: Artificial Sequence
<220> FEATURE:
<223> OTHER INFORMATION: synthesized-Primer-9AH31302

<400> SEQUENCE: 132
cgtgcggaag acacagcggt gtattattgc gcgcgtgggb wybwybwybw ykggbwykgg      60
atggattatt gggggcaggg cacccttgtt acc                                  93

<210> SEQ ID NO 133
<211> LENGTH: 93
<212> TYPE: DNA
<213> ORGANISM: Artificial Sequence
<220> FEATURE:
<223> OTHER INFORMATION: synthesized-Primer-9AH31303

<400> SEQUENCE: 133
cgtgcggaag acacagcggt gtattattgc gcgcgtgggb wybwybwykg gbwybwykgg      60
atggattatt gggggcaggg cacccttgtt acc                                  93

<210> SEQ ID NO 134
<211> LENGTH: 93
<212> TYPE: DNA
<213> ORGANISM: Artificial Sequence
<220> FEATURE:
<223> OTHER INFORMATION: synthesized-Primer-9AH31304

<400> SEQUENCE: 134
cgtgcggaag acacagcggt gtattattgc gcgcgtgggb wybwykggbw ybwybwykgg      60
atggattatt gggggcaggg cacccttgtt acc                                  93

<210> SEQ ID NO 135
<211> LENGTH: 93
<212> TYPE: DNA
```

<213> ORGANISM: Artificial Sequence
<220> FEATURE:
<223> OTHER INFORMATION: synthesized-Primer-9AH31305

<400> SEQUENCE: 135
cgtgcggaag acacagcggt gtattattgc gcgcgtgggb wykggbwybw ybwybwykgg    60
atggattatt gggggcaggg caccctgtt acc                                 93

<210> SEQ ID NO 136
<211> LENGTH: 93
<212> TYPE: DNA
<213> ORGANISM: Artificial Sequence
<220> FEATURE:
<223> OTHER INFORMATION: synthesized-Primer-9AH31306

<400> SEQUENCE: 136
cgtgcggaag acacagcggt gtattattgc gcgcgtgggk ggbwybwybw ybwybwykgg    60
atggattatt gggggcaggg caccctgtt acc                                 93

<210> SEQ ID NO 137
<211> LENGTH: 93
<212> TYPE: DNA
<213> ORGANISM: Artificial Sequence
<220> FEATURE:
<223> OTHER INFORMATION: synthesized-Primer-9AH31307

<400> SEQUENCE: 137
cgtgcggaag acacagcggt gtattattgc gcgcgtgggb wybwybwybw ykggkggbwy    60
atggattatt gggggcaggg caccctgtt acc                                 93

<210> SEQ ID NO 138
<211> LENGTH: 93
<212> TYPE: DNA
<213> ORGANISM: Artificial Sequence
<220> FEATURE:
<223> OTHER INFORMATION: synthesized-Primer-9AH31308

<400> SEQUENCE: 138
cgtgcggaag acacagcggt gtattattgc gcgcgtgggb wybwybwykg gbwykggbwy    60
atggattatt gggggcaggg caccctgtt acc                                 93

<210> SEQ ID NO 139
<211> LENGTH: 93
<212> TYPE: DNA
<213> ORGANISM: Artificial Sequence
<220> FEATURE:
<223> OTHER INFORMATION: synthesized-Primer-9AH31309

<400> SEQUENCE: 139
cgtgcggaag acacagcggt gtattattgc gcgcgtgggb wybwykggbw ybwykggbwy    60
atggattatt gggggcaggg caccctgtt acc                                 93

<210> SEQ ID NO 140
<211> LENGTH: 93
<212> TYPE: DNA
<213> ORGANISM: Artificial Sequence
<220> FEATURE:
<223> OTHER INFORMATION: synthesized-Primer-9AH31310

<400> SEQUENCE: 140
cgtgcggaag acacagcggt gtattattgc gcgcgtgggb wykggbwybw ybwykggbwy    60
atggattatt gggggcaggg caccctgtt acc                                 93

<210> SEQ ID NO 141
<211> LENGTH: 93
<212> TYPE: DNA
<213> ORGANISM: Artificial Sequence
<220> FEATURE:
<223> OTHER INFORMATION: synthesized-Primer-9AH31311

<400> SEQUENCE: 141
cgtgcggaag acacagcggt gtattattgc gcgcgtgggk ggbwybwybw ybwykggbwy      60
atggattatt gggggcaggg caccettgtt acc                                  93

<210> SEQ ID NO 142
<211> LENGTH: 93
<212> TYPE: DNA
<213> ORGANISM: Artificial Sequence
<220> FEATURE:
<223> OTHER INFORMATION: synthesized-Primer-9AH31312

<400> SEQUENCE: 142
cgtgcggaag acacagcggt gtattattgc gcgcgtgggb wybwbwykg gkggbwybwy       60 atggattatt gggggcaggg caccettgtt acc                                  93

<210> SEQ ID NO 143
<211> LENGTH: 93
<212> TYPE: DNA
<213> ORGANISM: Artificial Sequence
<220> FEATURE:
<223> OTHER INFORMATION: synthesized-Primer-9AH31313

<400> SEQUENCE: 143
cgtgcggaag acacagcggt gtattattgc gcgcgtgggb wybwykggbw ykggbwybwy      60
atggattatt gggggcaggg caccettgtt acc                                  93

<210> SEQ ID NO 144
<211> LENGTH: 93
<212> TYPE: DNA
<213> ORGANISM: Artificial Sequence
<220> FEATURE:
<223> OTHER INFORMATION: synthesized-Primer-9AH31314

<400> SEQUENCE: 144
cgtgcggaag acacagcggt gtattattgc gcgcgtgggb wykggbwybw ykggbwybwy      60
atggattatt gggggcaggg caccettgtt acc                                  93

<210> SEQ ID NO 145
<211> LENGTH: 93
<212> TYPE: DNA
<213> ORGANISM: Artificial Sequence
<220> FEATURE:
<223> OTHER INFORMATION: synthesized-Primer-9AH31315

<400> SEQUENCE: 145
cgtgcggaag acacagcggt gtattattgc gcgcgtgggk ggbwybwybw ykggbwybwy      60
atggattatt gggggcaggg caccettgtt acc                                  93

<210> SEQ ID NO 146
<211> LENGTH: 93
<212> TYPE: DNA
<213> ORGANISM: Artificial Sequence
<220> FEATURE:
<223> OTHER INFORMATION: synthesized-Primer-9AH31316

<400> SEQUENCE: 146
cgtgcggaag acacagcggt gtattattgc gcgcgtgggb wybwykggkg gbwybwybwy    60
atggattatt gggggcaggg cacccttgtt acc    93

<210> SEQ ID NO 147
<211> LENGTH: 93
<212> TYPE: DNA
<213> ORGANISM: Artificial Sequence
<220> FEATURE:
<223> OTHER INFORMATION: synthesized-Primer-9AH31317

<400> SEQUENCE: 147
cgtgcggaag acacagcggt gtattattgc gcgcgtgggb wykggbwykg gbwybwybwy    60
atggattatt gggggcaggg cacccttgtt acc    93

<210> SEQ ID NO 148
<211> LENGTH: 93
<212> TYPE: DNA
<213> ORGANISM: Artificial Sequence
<220> FEATURE:
<223> OTHER INFORMATION: synthesized-Primer-9AH31318

<400> SEQUENCE: 148
cgtgcggaag acacagcggt gtattattgc gcgcgtgggk ggbwybwykg gbwybwybwy    60
atggattatt gggggcaggg cacccttgtt acc    93

<210> SEQ ID NO 149
<211> LENGTH: 93
<212> TYPE: DNA
<213> ORGANISM: Artificial Sequence
<220> FEATURE:
<223> OTHER INFORMATION: synthesized-Primer-9AH31319

<400> SEQUENCE: 149
cgtgcggaag acacagcggt gtattattgc gcgcgtgggb wykggkggbw ybwybwybwy    60
atggattatt gggggcaggg cacccttgtt acc    93

<210> SEQ ID NO 150
<211> LENGTH: 93
<212> TYPE: DNA
<213> ORGANISM: Artificial Sequence
<220> FEATURE:
<223> OTHER INFORMATION: synthesized-Primer-9AH31320

<400> SEQUENCE: 150
cgtgcggaag acacagcggt gtattattgc gcgcgtgggk ggbwykggbw ybwybwybwy    60
atggattatt gggggcaggg cacccttgtt acc    93

<210> SEQ ID NO 151
<211> LENGTH: 93
<212> TYPE: DNA
<213> ORGANISM: Artificial Sequence
<220> FEATURE:
<223> OTHER INFORMATION: synthesized-Primer-9AH31321

<400> SEQUENCE: 151
cgtgcggaag acacagcggt gtattattgc gcgcgtgggk ggkggbwybw ybwybwybwy    60
atggattatt gggggcaggg cacccttgtt acc    93

<210> SEQ ID NO 152
<211> LENGTH: 24

<212> TYPE: DNA
<213> ORGANISM: Artificial Sequence
<220> FEATURE:
<223> OTHER INFORMATION: synthesized-9AH31301

<400> SEQUENCE: 152
gggbwybwyb wybwybwykg gkgg                                      24

<210> SEQ ID NO 153
<211> LENGTH: 24
<212> TYPE: DNA
<213> ORGANISM: Artificial Sequence
<220> FEATURE:
<223> OTHER INFORMATION: synthesized-9AH31302

<400> SEQUENCE: 153
gggbwybwyb wybwykggbw ykgg                                      24

<210> SEQ ID NO 154
<211> LENGTH: 24
<212> TYPE: DNA
<213> ORGANISM: Artificial Sequence
<220> FEATURE:
<223> OTHER INFORMATION: synthesized-9AH31303

<400> SEQUENCE: 154
gggbwybwyb wykggbwybw ykgg                                      24

<210> SEQ ID NO 155
<211> LENGTH: 24
<212> TYPE: DNA
<213> ORGANISM: Artificial Sequence
<220> FEATURE:
<223> OTHER INFORMATION: synthesized-9AH31304

<400> SEQUENCE: 155
gggbwybwyk ggbwybwybw ykgg                                      24

<210> SEQ ID NO 156
<211> LENGTH: 24
<212> TYPE: DNA
<213> ORGANISM: Artificial Sequence
<220> FEATURE:
<223> OTHER INFORMATION: synthesized-9AH31305

<400> SEQUENCE: 156
gggbwykggb wybwybwybw ykgg                                      24

<210> SEQ ID NO 157
<211> LENGTH: 24
<212> TYPE: DNA
<213> ORGANISM: Artificial Sequence
<220> FEATURE:
<223> OTHER INFORMATION: synthesized-9AH31306

<400> SEQUENCE: 157
gggkggbwyb wybwybwybw ykgg                                      24

<210> SEQ ID NO 158
<211> LENGTH: 24
<212> TYPE: DNA
<213> ORGANISM: Artificial Sequence
<220> FEATURE:
<223> OTHER INFORMATION: synthesized-9AH31307

<400> SEQUENCE: 158
gggbwybwyb wybwykggkg gbwy					24

<210> SEQ ID NO 159
<211> LENGTH: 24
<212> TYPE: DNA
<213> ORGANISM: Artificial Sequence
<220> FEATURE:
<223> OTHER INFORMATION: synthesized-9AH31308

<400> SEQUENCE: 159
gggbwybwyb wykggbwykg gbwy					24

<210> SEQ ID NO 160
<211> LENGTH: 24
<212> TYPE: DNA
<213> ORGANISM: Artificial Sequence
<220> FEATURE:
<223> OTHER INFORMATION: synthesized-9AH31309

<400> SEQUENCE: 160
gggbwybwyk ggbwybwykg gbwy					24

<210> SEQ ID NO 161
<211> LENGTH: 24
<212> TYPE: DNA
<213> ORGANISM: Artificial Sequence
<220> FEATURE:
<223> OTHER INFORMATION: synthesized-9AH31310

<400> SEQUENCE: 161
gggbwykggb wybwybwykg gbwy					24

<210> SEQ ID NO 162
<211> LENGTH: 24
<212> TYPE: DNA
<213> ORGANISM: Artificial Sequence
<220> FEATURE:
<223> OTHER INFORMATION: synthesized-9AH31311

<400> SEQUENCE: 162
gggkggbwyb wybwybwykg gbwy					24

<210> SEQ ID NO 163
<211> LENGTH: 24
<212> TYPE: DNA
<213> ORGANISM: Artificial Sequence
<220> FEATURE:
<223> OTHER INFORMATION: synthesized-9AH31312

<400> SEQUENCE: 163
gggbwybwyb wykggkggbw ybwy					24

<210> SEQ ID NO 164
<211> LENGTH: 24
<212> TYPE: DNA
<213> ORGANISM: Artificial Sequence
<220> FEATURE:
<223> OTHER INFORMATION: synthesized-9AH31313

<400> SEQUENCE: 164
gggbwybwyk ggbwykggbw ybwy					24

<210> SEQ ID NO 165
<211> LENGTH: 24
<212> TYPE: DNA
<213> ORGANISM: Artificial Sequence
<220> FEATURE:
<223> OTHER INFORMATION: synthesized-9AH31314

<400> SEQUENCE: 165
gggbwykggb wybwykggbw ybwy           24

<210> SEQ ID NO 166
<211> LENGTH: 24
<212> TYPE: DNA
<213> ORGANISM: Artificial Sequence
<220> FEATURE:
<223> OTHER INFORMATION: synthesized-9AH31315

<400> SEQUENCE: 166
gggkggbwyb wybwykggbw ybwy           24

<210> SEQ ID NO 167
<211> LENGTH: 24
<212> TYPE: DNA
<213> ORGANISM: Artificial Sequence
<220> FEATURE:
<223> OTHER INFORMATION: synthesized-9AH31316

<400> SEQUENCE: 167
gggbwybwyk ggkggbwybw ybwy           24

<210> SEQ ID NO 168
<211> LENGTH: 24
<212> TYPE: DNA
<213> ORGANISM: Artificial Sequence
<220> FEATURE:
<223> OTHER INFORMATION: synthesized-9AH31317

<400> SEQUENCE: 168
gggbwykggb wykggbwybw ybwy           24

<210> SEQ ID NO 169
<211> LENGTH: 24
<212> TYPE: DNA
<213> ORGANISM: Artificial Sequence
<220> FEATURE:
<223> OTHER INFORMATION: synthesized-9AH31318

<400> SEQUENCE: 169
gggkggbwyb wykggbwybw ybwy           24

<210> SEQ ID NO 170
<211> LENGTH: 24
<212> TYPE: DNA
<213> ORGANISM: Artificial Sequence
<220> FEATURE:
<223> OTHER INFORMATION: synthesized-9AH31319

<400> SEQUENCE: 170
gggbwykggk ggbwybwybw ybwy           24

<210> SEQ ID NO 171
<211> LENGTH: 24
<212> TYPE: DNA
<213> ORGANISM: Artificial Sequence
<220> FEATURE:
<223> OTHER INFORMATION: synthesized-9AH31320

<400> SEQUENCE: 171
gggkggbwyk ggbwybwybw ybwy           24

<210> SEQ ID NO 172
<211> LENGTH: 24
<212> TYPE: DNA
<213> ORGANISM: Artificial Sequence
<220> FEATURE:
<223> OTHER INFORMATION: synthesized-9AH31321

<400> SEQUENCE: 172
gggkggkggb wybwybwybw ybwy                                          24

<210> SEQ ID NO 173
<211> LENGTH: 114
<212> TYPE: PRT
<213> ORGANISM: Artificial Sequence
<220> FEATURE:
<223> OTHER INFORMATION: synthesized-30CHS-12_LC

<400> SEQUENCE: 173

Asp Ile Gln Met Thr Gln Ser Pro Ser Ser Leu Ser Ala Ser Val Gly
1               5                   10                  15

Asp Arg Val Thr Ile Thr Cys Lys Ser Asn Gln Asn Leu Leu Asp Ser
            20                  25                  30

Gly Asn Gln Gly Thr Phe Leu Asn Trp Tyr Gln Lys Pro Gly Lys
        35                  40                  45

Ala Pro Lys Leu Leu Ile Phe Gly Thr Ser His Leu Tyr Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Ser Gln
                85                  90                  95

Ser Thr Asp Leu Pro Phe Thr Phe Gly Gln Gly Thr Lys Val Glu Ile
            100                 105                 110

Lys Arg

<210> SEQ ID NO 174
<211> LENGTH: 120
<212> TYPE: PRT
<213> ORGANISM: Artificial Sequence
<220> FEATURE:
<223> OTHER INFORMATION: synthesized-30CHS-12_HC

<400> SEQUENCE: 174

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Ser Asp Tyr
            20                  25                  30

Trp Ile His Trp Val Arg Gln Ala Pro Gly Lys Gly Leu Glu Trp Val
        35                  40                  45

Ala Gly Ile Asn Pro Tyr Tyr Gly Val Thr Val Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Gly Val Leu Asp Tyr Trp Gly Gln Gly Thr Leu Val Thr
            100                 105                 110

Val Ser Ser Ala Ser Ala Ala Ala
            115                 120

<210> SEQ ID NO 175
<211> LENGTH: 114
<212> TYPE: PRT
<213> ORGANISM: Artificial Sequence
<220> FEATURE:
<223> OTHER INFORMATION: synthesized-30CHS-13_LC

<400> SEQUENCE: 175

```
Asp Ile Gln Met Thr Gln Ser Pro Ser Leu Ser Ala Ser Val Gly
1               5                   10                  15

Asp Arg Val Thr Ile Thr Cys Lys Ser Asn Gln Asn Leu Leu Asp Ser
            20                  25                  30

Gly Asn Gln Arg Thr Tyr Leu Asn Trp Tyr Gln Gln Lys Pro Gly Lys
        35                  40                  45

Ala Pro Lys Leu Leu Ile Tyr His Thr Ser Arg Leu Tyr Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Ser Gln
                85                  90                  95

Thr Phe Arg His Pro Gly Thr Phe Gly Gln Gly Thr Lys Val Glu Ile
            100                 105                 110

Lys Arg
```

<210> SEQ ID NO 176
<211> LENGTH: 120
<212> TYPE: PRT
<213> ORGANISM: Artificial Sequence
<220> FEATURE:
<223> OTHER INFORMATION: synthesized-30CHS-13_HC

<400> SEQUENCE: 176

```
Glu Val Gln Leu Val Glu Ser Gly Gly Gly Leu Val Gln Pro Gly Gly
1               5                   10                  15

Ser Leu Arg Leu Ser Cys Lys Ala Ser Gly Tyr Thr Phe Gly His Tyr
            20                  25                  30

Ser Met Phe Trp Val Arg Gln Ala Pro Gly Lys Gly Leu Glu Trp Val
        35                  40                  45

Ala Ser Ile Tyr Pro His Tyr Gly His Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly His Trp Leu Asp Tyr Trp Gly Gln Gly Thr Leu Val Thr
            100                 105                 110

Val Ser Ser Ala Ser Ala Ala Ala
        115                 120
```

<210> SEQ ID NO 177
<211> LENGTH: 114
<212> TYPE: PRT
<213> ORGANISM: Artificial Sequence
<220> FEATURE:
<223> OTHER INFORMATION: synthesized-30CHS-41_LC

<400> SEQUENCE: 177

```
Asp Ile Gln Met Thr Gln Ser Pro Ser Leu Ser Ala Ser Val Gly
1               5                   10                  15
```

```
Asp Arg Val Thr Ile Thr Cys Lys Ser Asn Gln Asn Leu Leu Asp Ser
            20                  25                  30

Gly His Gln Arg Thr Tyr Leu Asn Trp Tyr Gln Gln Lys Pro Gly Lys
        35                  40                  45

Ala Pro Lys Leu Leu Ile Tyr His Thr Ser Leu Leu Tyr Ser Gly Val
 50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Ser Gln
            85                  90                  95

Thr Phe Arg His Pro Gly Thr Phe Gly Gln Gly Thr Lys Val Glu Ile
            100                 105                 110

Lys Arg

<210> SEQ ID NO 178
<211> LENGTH: 120
<212> TYPE: PRT
<213> ORGANISM: Artificial Sequence
<220> FEATURE:
<223> OTHER INFORMATION: synthesized-30CHS-41_HC

<400> SEQUENCE: 178

Glu Val Gln Leu Val Glu Ser Gly Gly Leu Val Gln Pro Gly Gly
1               5                   10                  15

Ser Leu Arg Leu Ser Cys Lys Ala Ser Gly Tyr Thr Phe Thr His Trp
            20                  25                  30

Gly Met His Trp Val Arg Gln Ala Pro Gly Lys Gly Leu Glu Trp Val
        35                  40                  45

Ala Arg Ile Asn Pro Tyr Tyr Gly Leu Thr His Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
            85                  90                  95

Ala Arg Gly His Trp Leu Asp Tyr Trp Gly Gln Gly Thr Leu Val Thr
            100                 105                 110

Val Ser Ser Ala Ser Ala Ala Ala
        115                 120

<210> SEQ ID NO 179
<211> LENGTH: 113
<212> TYPE: PRT
<213> ORGANISM: Artificial Sequence
<220> FEATURE:
<223> OTHER INFORMATION: synthesized-35CPT-9_LC

<400> SEQUENCE: 179

Asp Ile Gln Met Thr Gln Ser Pro Ser Ser Leu Ser Ala Ser Val Gly
1               5                   10                  15

Gly Arg Val Thr Ile Thr Cys Lys Ser Asn Gln Asn Leu Leu Asp Ser
            20                  25                  30

Tyr Gly Arg Thr Tyr Leu Tyr Trp Tyr Gln Gln Lys Pro Gly Lys Ala
        35                  40                  45

Pro Lys Leu Leu Ile Ser Gly Thr Ser Gly Leu Tyr Ser Gly Val Pro
 50                  55                  60

Ser Arg Phe Ser Gly Ser Gly Ser Gly Thr Asp Phe Thr Leu Thr Ile
 65                  70                  75                  80
```

```
Ser Ser Leu Gln Pro Glu Asp Phe Ala Thr Tyr Tyr Cys Phe Gln Gly
                85                  90                  95

Tyr Asp Tyr Pro Phe Thr Phe Gly Gln Gly Thr Lys Val Glu Ile Lys
            100                 105                 110

Arg

<210> SEQ ID NO 180
<211> LENGTH: 125
<212> TYPE: PRT
<213> ORGANISM: Artificial Sequence
<220> FEATURE:
<223> OTHER INFORMATION: synthesized-35CPT-9_HC

<400> SEQUENCE: 180

Glu Val Gln Leu Val Glu Ser Gly Gly Gly Leu Val Gln Pro Gly Gly
1               5                   10                  15

Ser Leu Arg Leu Ser Cys Lys Ala Ser Gly Tyr Thr Phe Gly Asp Tyr
            20                  25                  30

Gly Met His Trp Val Arg Gln Ala Pro Gly Lys Gly Leu Glu Trp Val
        35                  40                  45

Ala His Ile Ala Pro Asn Asp Gly Ile Thr His Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Tyr Gly Trp Tyr Asp His Val Met Asp Tyr Trp Gly Gln
            100                 105                 110

Gly Thr Leu Val Thr Val Ser Ser Ala Ser Ala Ala Ala
        115                 120                 125

<210> SEQ ID NO 181
<211> LENGTH: 113
<212> TYPE: PRT
<213> ORGANISM: Artificial Sequence
<220> FEATURE:
<223> OTHER INFORMATION: synthesized-35WYK-9_LC

<400> SEQUENCE: 181

Asp Ile Gln Met Thr Gln Ser Pro Ser Ser Leu Ser Ala Ser Val Gly
1               5                   10                  15

Asp Arg Val Thr Ile Thr Cys Lys Ser Asn Gln Asn Leu Leu Leu Ser
            20                  25                  30

Asn Gly Arg Thr Phe Leu His Trp Tyr Gln Gln Lys Pro Gly Lys Ala
        35                  40                  45

Pro Lys Leu Leu Ile Phe Asp Val Ser Asn Leu Tyr Ser Gly Ala Pro
    50                  55                  60

Ser Arg Phe Ser Gly Ser Gly Ser Gly Thr Asp Phe Thr Leu Thr Ile
65                  70                  75                  80

Ser Ser Leu Gln Pro Asp Asp Phe Ala Thr Tyr Tyr Cys Ser Gln Thr
                85                  90                  95

Ser Arg Phe Pro Trp Thr Phe Gly Gln Gly Thr Lys Val Glu Ile Lys
            100                 105                 110

Arg

<210> SEQ ID NO 182
<211> LENGTH: 119
```

```
<212> TYPE: PRT
<213> ORGANISM: Artificial Sequence
<220> FEATURE:
<223> OTHER INFORMATION: synthesized-35WYK-9_HC

<400> SEQUENCE: 182

Glu Val Gln Leu Val Glu Ser Gly Gly Gly Leu Val Gln Pro Gly Gly
1               5                   10                  15

Ser Leu Arg Leu Ser Cys Lys Ala Ser Gly Tyr Thr Phe Ser His Trp
            20                  25                  30

Gly Met His Trp Val Arg Gln Ala Pro Gly Lys Gly Leu Glu Trp Val
        35                  40                  45

Ala Gly Ile Tyr Pro Tyr Phe Gly Asn Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Leu Leu Asp Tyr Trp Gly Gln Gly Thr Leu Val Thr Val
            100                 105                 110

Ser Ser Ala Ser Ala Ala Ala
        115

<210> SEQ ID NO 183
<211> LENGTH: 113
<212> TYPE: PRT
<213> ORGANISM: Artificial Sequence
<220> FEATURE:
<223> OTHER INFORMATION: synthesized-35WYK-16_LC

<400> SEQUENCE: 183

Asp Ile Gln Met Thr Gln Ser Pro Ser Ser Leu Ser Ala Ser Val Gly
1               5                   10                  15

Asp Arg Val Thr Ile Thr Cys Lys Ser Asn Gln Asn Leu Leu Leu Ser
            20                  25                  30

Asn Gly Arg Thr Phe Leu Tyr Trp Tyr Gln Gln Lys Pro Gly Lys Ala
        35                  40                  45

Pro Lys Leu Leu Ile Tyr Asp Val Ser Asp Leu Tyr Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Gln Gln Gly
                85                  90                  95

Asn Asn Phe Pro Tyr Thr Phe Gly Gln Gly Thr Lys Val Glu Ile Lys
            100                 105                 110

Arg

<210> SEQ ID NO 184
<211> LENGTH: 119
<212> TYPE: PRT
<213> ORGANISM: Artificial Sequence
<220> FEATURE:
<223> OTHER INFORMATION: synthesized-35WYK-16_HC

<400> SEQUENCE: 184

Glu Val Gln Leu Val Glu Ser Gly Gly Gly Leu Val Gln Pro Gly Gly
1               5                   10                  15

Ser Leu Arg Leu Ser Cys Lys Ala Ser Gly Tyr Thr Phe Gly Thr Ser
            20                  25                  30
```

```
Trp Met His Trp Val Arg Gln Ala Pro Gly Lys Gly Leu Glu Trp Val
        35                  40                  45

Ala Gly Ile Thr Pro Tyr Tyr Gly Leu Thr Phe Tyr Ala Asp Ser Val
 50                  55                  60

Lys Gly Arg Phe Thr Ile Ser Asp Thr Ser Lys Asn Thr Ala Tyr
 65                  70                  75                  80

Leu Gln Met Asn Ser Leu Arg Ala Glu Asp Thr Ala Val Tyr Tyr Cys
                85                  90                  95

Ala Arg Gly Asn Leu Asp Tyr Trp Gly Gln Gly Thr Leu Val Thr Val
            100                 105                 110

Ser Ser Ala Ser Ala Ala Ala
        115
```

<210> SEQ ID NO 185
<211> LENGTH: 113
<212> TYPE: PRT
<213> ORGANISM: Artificial Sequence
<220> FEATURE:
<223> OTHER INFORMATION: synthesized-29TYL_1_LC

<400> SEQUENCE: 185

```
Asp Ile Gln Met Thr Gln Ser Pro Ser Ser Leu Ser Ala Ser Val Gly
 1               5                  10                  15

Asp Arg Val Thr Ile Thr Cys Lys Ser Asn Gln Asn Leu Leu Leu Ser
                20                  25                  30

Asn Gly Trp Thr Phe Leu Asn Trp Tyr Gln Gln Lys Pro Gly Lys Ala
            35                  40                  45

Pro Lys Leu Leu Ile Ser Arg Ile Ser Asp Leu Tyr Ser Gly Val Pro
 50                  55                  60

Ser Arg Phe Ser Gly Ser Gly Ser Gly Thr Asp Phe Thr Leu Thr Ile
 65                  70                  75                  80

Ser Ser Leu Gln Pro Glu Asp Phe Ala Thr Tyr Tyr Cys Phe Gln Ala
                85                  90                  95

Ser Asp Phe Pro Tyr Thr Phe Gly Gln Gly Thr Lys Val Glu Ile Lys
            100                 105                 110

Arg
```

<210> SEQ ID NO 186
<211> LENGTH: 119
<212> TYPE: PRT
<213> ORGANISM: Artificial Sequence
<220> FEATURE:
<223> OTHER INFORMATION: synthesized-29TYL_1_HC

<400> SEQUENCE: 186

```
Glu Val Gln Leu Val Glu Ser Gly Gly Gly Leu Val Gln Pro Gly Gly
 1               5                  10                  15

Ser Leu Arg Leu Ser Cys Lys Ala Ser Gly Tyr Thr Phe Ser Thr Gly
                20                  25                  30

Ser Met His Trp Val Arg Gln Ala Pro Gly Lys Gly Leu Glu Trp Val
            35                  40                  45

Ala His Ile Asn Pro His Phe Gly Leu Thr Leu Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                85                  90                  95
```

Ala Gly Ser Gly Phe Asp Tyr Trp Gly Gln Gly Thr Leu Val Thr Val
            100                 105                 110

Ser Ser Ala Ser Ala Ala Ala
        115

<210> SEQ ID NO 187
<211> LENGTH: 113
<212> TYPE: PRT
<213> ORGANISM: Artificial Sequence
<220> FEATURE:
<223> OTHER INFORMATION: synthesized-29TYL_10_LC

<400> SEQUENCE: 187

Asp Ile Gln Met Thr Gln Ser Pro Ser Ser Leu Ser Ala Ser Val Gly
1               5                   10                  15

Asp Arg Val Thr Ile Thr Cys Lys Ser Asn Gln Asn Leu Leu Leu Ser
            20                  25                  30

Asn Gly Arg Thr Phe Leu Tyr Trp Tyr Gln Gln Lys Pro Gly Lys Ala
        35                  40                  45

Pro Lys Leu Leu Ile Tyr Gly Thr Ser Tyr Leu Tyr Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Phe Gln Ala
                85                  90                  95

Asn His Leu Pro Trp Thr Phe Gly Gln Gly Thr Lys Val Glu Ile Lys
            100                 105                 110

Arg

<210> SEQ ID NO 188
<211> LENGTH: 119
<212> TYPE: PRT
<213> ORGANISM: Artificial Sequence
<220> FEATURE:
<223> OTHER INFORMATION: synthesized-29TYL_10_HC

<400> SEQUENCE: 188

Glu Val Gln Leu Val Glu Ser Gly Gly Gly Leu Val Gln Pro Gly Gly
1               5                   10                  15

Ser Leu Arg Leu Ser Cys Lys Ala Ser Gly Tyr Thr Phe Thr Asp Gly
            20                  25                  30

Ser Met His Trp Val Arg Gln Ala Pro Gly Lys Gly Leu Glu Trp Val
        35                  40                  45

Ala Tyr Ile Asn Pro Tyr Phe Gly Asp Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Trp Ile Asp Tyr Trp Gly Gln Gly Thr Leu Val Thr Val
            100                 105                 110

Ser Ser Ala Ser Ala Ala Ala
        115

<210> SEQ ID NO 189
<211> LENGTH: 114
<212> TYPE: PRT
<213> ORGANISM: Artificial Sequence

```
<220> FEATURE:
<223> OTHER INFORMATION: synthesized-31YCM_3_LC

<400> SEQUENCE: 189

Asp Ile Gln Met Thr Gln Ser Pro Ser Ser Leu Ser Ala Ser Val Gly
1               5                   10                  15

Asp Arg Val Thr Ile Thr Cys Lys Ser Asn Gln Asn Leu Leu Ile Ser
            20                  25                  30

Gly Asn Gln Trp Thr Phe Leu Asn Trp Tyr Gln Gln Lys Pro Gly Lys
        35                  40                  45

Ala Pro Lys Leu Leu Ile Tyr Asp Val Ser Arg Leu Tyr Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Tyr Gln
                85                  90                  95

Gly Ser Asp Phe Pro Gly Thr Phe Gly Gln Gly Thr Lys Val Glu Ile
            100                 105                 110

Lys Arg

<210> SEQ ID NO 190
<211> LENGTH: 121
<212> TYPE: PRT
<213> ORGANISM: Artificial Sequence
<220> FEATURE:
<223> OTHER INFORMATION: synthesized-31YCM_3_HC

<400> SEQUENCE: 190

Glu Val Gln Leu Val Glu Ser Gly Gly Gly Leu Val Gln Pro Gly Gly
1               5                   10                  15

Ser Leu Arg Leu Ser Cys Lys Ala Ser Gly Tyr Thr Phe Ala Arg Ser
            20                  25                  30

Gly Met His Trp Val Arg Gln Ala Pro Gly Lys Gly Leu Glu Trp Val
        35                  40                  45

Ala Gly Ile Ser Pro Asn Tyr Gly Leu Thr His Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Phe Gly Val Leu Asp Tyr Trp Gly Gln Gly Thr Leu Val
            100                 105                 110

Thr Val Ser Ser Ala Ser Ala Ala Ala
        115                 120

<210> SEQ ID NO 191
<211> LENGTH: 113
<212> TYPE: PRT
<213> ORGANISM: Artificial Sequence
<220> FEATURE:
<223> OTHER INFORMATION: synthesized-31YCM_5_LC

<400> SEQUENCE: 191

Asp Ile Gln Met Thr Gln Ser Pro Ser Ser Leu Ser Ala Ser Val Gly
1               5                   10                  15

Asp Arg Val Thr Ile Thr Cys Lys Ser Asn Gln Asn Leu Leu Asp Ser
            20                  25                  30

His Gly Trp Thr Tyr Leu His Trp Tyr Gln Gln Lys Pro Gly Lys Ala
```

```
                35                  40                  45
Pro Lys Leu Leu Ile Tyr Asp Ala Ser Asn Leu Tyr Ser Gly Val Pro
 50                  55                  60

Ser Arg Phe Ser Gly Ser Gly Ser Gly Thr Asp Phe Thr Leu Thr Ile
 65                  70                  75                  80

Ser Ser Leu Gln Pro Glu Asp Phe Ala Thr Tyr Tyr Cys Ser Gln Ser
                 85                  90                  95

Tyr Arg Leu Pro Tyr Thr Phe Gly Gln Gly Thr Lys Val Glu Ile Lys
                100                 105                 110

Arg

<210> SEQ ID NO 192
<211> LENGTH: 121
<212> TYPE: PRT
<213> ORGANISM: Artificial Sequence
<220> FEATURE:
<223> OTHER INFORMATION: synthesized-31YCM_5_HC

<400> SEQUENCE: 192

Glu Val Gln Leu Val Glu Ser Gly Gly Gly Leu Val Gln Pro Gly Gly
 1               5                  10                  15

Ser Leu Arg Leu Ser Cys Lys Ala Ser Gly Tyr Thr Phe Gly Gly Ser
                20                  25                  30

Tyr Met His Trp Val Arg Gln Ala Pro Gly Lys Gly Leu Glu Trp Val
             35                  40                  45

Ala Arg Ile Tyr Pro His Tyr Gly Tyr Thr Tyr Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Gly Asp Asp His Phe Asp Tyr Trp Gly Gln Gly Thr Leu Val
                100                 105                 110

Thr Val Ser Ser Ala Ser Ala Ala Ala
            115                 120

<210> SEQ ID NO 193
<211> LENGTH: 113
<212> TYPE: PRT
<213> ORGANISM: Artificial Sequence
<220> FEATURE:
<223> OTHER INFORMATION: synthesized-2835-28_LC

<400> SEQUENCE: 193

Asp Ile Gln Met Thr Gln Ser Pro Ser Ser Leu Ser Ala Ser Val Gly
 1               5                  10                  15

Asp Arg Val Thr Ile Thr Cys Lys Ser Asn Gln Asn Leu Leu Leu Ser
                20                  25                  30

Asn Gly Arg Thr Phe Leu Tyr Trp Tyr Gln Gln Lys Pro Gly Lys Ala
             35                  40                  45

Pro Lys Leu Leu Ile Tyr Gly Thr Ser Tyr Leu Tyr Ser Gly Val Pro
 50                  55                  60

Ser Arg Phe Ser Gly Ser Gly Ser Gly Thr Asp Phe Thr Leu Thr Ile
 65                  70                  75                  80

Ser Ser Leu Gln Pro Glu Asp Phe Ala Thr Tyr Tyr Cys Phe Gln Ala
                 85                  90                  95

Asn His Leu Pro Trp Thr Phe Gly Gln Gly Thr Lys Val Glu Ile Lys
```

Arg

<210> SEQ ID NO 194
<211> LENGTH: 119
<212> TYPE: PRT
<213> ORGANISM: Artificial Sequence
<220> FEATURE:
<223> OTHER INFORMATION: synthesized-2835-28_HC

<400> SEQUENCE: 194

Glu Val Gln Leu Val Glu Ser Gly Gly Gly Leu Val Gln Pro Gly Gly
1               5                   10                  15

Ser Leu Arg Leu Ser Cys Lys Ala Ser Gly Tyr Thr Phe Thr Asp Gly
            20                  25                  30

Ser Met His Trp Val Arg Gln Ala Pro Gly Lys Gly Leu Glu Trp Val
        35                  40                  45

Ala Tyr Ile Asn Pro Tyr Phe Gly Asp Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Trp Ile Asp Tyr Trp Gly Gln Gly Thr Leu Val Thr Val
            100                 105                 110

Ser Ser Ala Ser Ala Ala Ala
        115

<210> SEQ ID NO 195
<211> LENGTH: 47
<212> TYPE: DNA
<213> ORGANISM: Artificial Sequence
<220> FEATURE:
<223> OTHER INFORMATION: synthesized-Third NC amplification-F

<400> SEQUENCE: 195
gggcccagcc ggccatggcc gatattcaaa tgacccagag cccgagc         47

<210> SEQ ID NO 196
<211> LENGTH: 51
<212> TYPE: DNA
<213> ORGANISM: Artificial Sequence
<220> FEATURE:
<223> OTHER INFORMATION: synthesized-Third NC amplification-R

<400> SEQUENCE: 196
ggaagatcta gaggaaccac cgcgtttgat ttccactttg gtgccttgac c     51

<210> SEQ ID NO 197
<211> LENGTH: 77
<212> TYPE: PRT
<213> ORGANISM: Artificial Sequence
<220> FEATURE:
<223> OTHER INFORMATION: synthesized-Fourth NC amplification-F

<400> SEQUENCE: 197

Gly Gly Thr Gly Gly Thr Thr Cys Cys Thr Cys Thr Ala Gly Ala Thr
1               5                   10                  15

Cys Thr Thr Cys Cys Thr Cys Cys Thr Cys Thr Gly Gly Thr Gly Gly
            20                  25                  30

Cys Gly Gly Thr Gly Gly Cys Thr Cys Gly Gly Gly Cys Gly Gly Thr

```
                 35                  40                  45
Gly Gly Thr Gly Gly Gly Ala Ala Gly Thr Gly Cys Ala Gly Cys
     50                  55                  60
Thr Gly Gly Thr Gly Gly Ala Ala Thr Cys Gly Gly Gly
 65                  70                  75
```

<210> SEQ ID NO 198
<211> LENGTH: 26
<212> TYPE: DNA
<213> ORGANISM: Artificial Sequence
<220> FEATURE:
<223> OTHER INFORMATION: synthesized-Fourth NC amplification-R

<400> SEQUENCE: 198
cctgcctgcg gccgctgacg ccgagc                                    26

<210> SEQ ID NO 199
<211> LENGTH: 48
<212> TYPE: DNA
<213> ORGANISM: Artificial Sequence
<220> FEATURE:
<223> OTHER INFORMATION: synthesized-Overlapping primer-F

<400> SEQUENCE: 199
gaggaggagg aggaggaggc ggggcccagc cggccatggc cgatattc             48

<210> SEQ ID NO 200
<211> LENGTH: 40
<212> TYPE: DNA
<213> ORGANISM: Artificial Sequence
<220> FEATURE:
<223> OTHER INFORMATION: synthesized-Overlapping primer-R

<400> SEQUENCE: 200
gaggaggagg aggaggagcc tgcctgcggc cgctgacgcc                      40

<210> SEQ ID NO 201
<211> LENGTH: 59
<212> TYPE: DNA
<213> ORGANISM: Artificial Sequence
<220> FEATURE:
<223> OTHER INFORMATION: synthesized-Recombinant Ab-VL primer-F

<400> SEQUENCE: 201
caggtgcacg atgtgatggt accgatattc aaatgaccca gagcccgagc agcctgagc    59

<210> SEQ ID NO 202
<211> LENGTH: 36
<212> TYPE: DNA
<213> ORGANISM: Artificial Sequence
<220> FEATURE:
<223> OTHER INFORMATION: synthesized-Recombinant Ab-VL primer-R

<400> SEQUENCE: 202
tgcagccacc gtacgtttga tttccacctt ggtgcc                         36

<210> SEQ ID NO 203
<211> LENGTH: 36
<212> TYPE: DNA
<213> ORGANISM: Artificial Sequence
<220> FEATURE:
<223> OTHER INFORMATION: synthesized-Recombinant Ab-VH primer-F

<400> SEQUENCE: 203
cgtgtcgcat ctgaagtgca gctggtggaa tcggga                         36

<210> SEQ ID NO 204
<211> LENGTH: 48
<212> TYPE: DNA
<213> ORGANISM: Artificial Sequence
<220> FEATURE:
<223> OTHER INFORMATION: synthesized-Recombinant Ab-VH primer-R

<400> SEQUENCE: 204
gaccgatggg cccttggtgc tagccgagct cacggtaaca agggtgcc         48

<210> SEQ ID NO 205
<211> LENGTH: 39
<212> TYPE: DNA
<213> ORGANISM: Artificial Sequence
<220> FEATURE:
<223> OTHER INFORMATION: synthesized-Recombinant Ab-linker-F

<400> SEQUENCE: 205
aaggtggaaa tcaaacgtac ggtggctgca ccatctgtc                    39

<210> SEQ ID NO 206
<211> LENGTH: 33
<212> TYPE: DNA
<213> ORGANISM: Artificial Sequence
<220> FEATURE:
<223> OTHER INFORMATION: synthesized-Recombinant Ab-linker-R

<400> SEQUENCE: 206
ctgcacttca gatgcgacac gcgtagcaac agc                          33

<210> SEQ ID NO 207
<211> LENGTH: 140
<212> TYPE: PRT
<213> ORGANISM: Artificial Sequence
<220> FEATURE:
<223> OTHER INFORMATION: synthesized-AL1

<400> SEQUENCE: 207

Gly Ser Tyr Asn Lys Asp Gln Gln Ser Ala Phe Tyr Glu Ile Leu Asn
1               5                   10                  15

Met Pro Asn Leu Asn Glu Glu Gln Arg Asn Gly Phe Ile Gln Ser Leu
            20                  25                  30

Lys Asp Asp Pro Ser Gln Ser Thr Asn Val Leu Gly Glu Ala Lys Lys
        35                  40                  45

Leu Asn Glu Ser Gln Ala Pro Lys Ala Asp Asn Gly Gly Gly Ser Gly
    50                  55                  60

Gly Gly Ser Gly Gly Gly Ser Gly Gly Ser Gly Gly Ser Glu Val
65                  70                  75                  80

Thr Ile Lys Val Asn Leu Ile Phe Ala Asp Gly Lys Ile Gln Thr Ala
                85                  90                  95

Glu Phe Lys Gly Thr Phe Glu Glu Ala Thr Ala Glu Ala Tyr Arg Tyr
            100                 105                 110

Ala Ala Leu Leu Ala Lys Val Asn Gly Glu Tyr Thr Ala Asp Leu Glu
        115                 120                 125

Asp Gly Gly Asn His Met Asn Ile Lys Phe Ala Gly
    130                 135                 140

<210> SEQ ID NO 208
<211> LENGTH: 283
<212> TYPE: PRT
<213> ORGANISM: Artificial Sequence

```
<220> FEATURE:
<223> OTHER INFORMATION: synthesized-AL2

<400> SEQUENCE: 208

Gly Ser Tyr Asn Lys Asp Gln Gln Ser Ala Phe Tyr Glu Ile Leu Asn
1               5                   10                  15

Met Pro Asn Leu Asn Glu Glu Gln Arg Asn Gly Phe Ile Gln Ser Leu
            20                  25                  30

Lys Asp Asp Pro Ser Gln Ser Thr Asn Val Leu Gly Glu Ala Lys Lys
        35                  40                  45

Leu Asn Glu Ser Gln Ala Pro Lys Ala Asp Asn Gly Gly Ser Gly
    50                  55                  60

Gly Gly Ser Gly Gly Ser Gly Gly Gly Ser Gly Gly Ser Glu Val
65                  70                  75                  80

Thr Ile Lys Val Asn Leu Ile Phe Ala Asp Gly Lys Ile Gln Thr Ala
                85                  90                  95

Glu Phe Lys Gly Thr Phe Glu Glu Ala Thr Ala Glu Ala Tyr Arg Tyr
            100                 105                 110

Ala Ala Leu Leu Ala Lys Val Asn Gly Glu Tyr Thr Ala Asp Leu Glu
        115                 120                 125

Asp Gly Gly Asn His Met Asn Ile Lys Phe Ala Gly Gly Ser Gly
    130                 135                 140

Gly Tyr Asn Lys Asp Gln Gln Ser Ala Phe Tyr Glu Ile Leu Asn Met
145                 150                 155                 160

Pro Asn Leu Asn Glu Glu Gln Arg Asn Gly Phe Ile Gln Ser Leu Lys
            165                 170                 175

Asp Asp Pro Ser Gln Ser Thr Asn Val Leu Gly Glu Ala Lys Lys Leu
        180                 185                 190

Asn Glu Ser Gln Ala Pro Lys Ala Asp Asn Gly Gly Ser Gly Gly
    195                 200                 205

Gly Ser Gly Gly Gly Ser Gly Gly Gly Ser Gly Gly Ser Glu Val Thr
210                 215                 220

Ile Lys Val Asn Leu Ile Phe Ala Asp Gly Lys Ile Gln Thr Ala Glu
225                 230                 235                 240

Phe Lys Gly Thr Phe Glu Glu Ala Thr Ala Glu Ala Tyr Arg Tyr Ala
            245                 250                 255

Ala Leu Leu Ala Lys Val Asn Gly Glu Tyr Thr Ala Asp Leu Glu Asp
        260                 265                 270

Gly Gly Asn His Met Asn Ile Lys Phe Ala Gly
    275                 280

<210> SEQ ID NO 209
<211> LENGTH: 344
<212> TYPE: PRT
<213> ORGANISM: Artificial Sequence
<220> FEATURE:
<223> OTHER INFORMATION: synthesized-PE38KDEL

<400> SEQUENCE: 209

Gly Gly Ser Leu Ala Ala Leu Thr Ala His Gln Ala Cys His Leu Pro
1               5                   10                  15

Leu Glu Thr Phe Thr Arg His Arg Gln Pro Arg Gly Trp Glu Gln Leu
            20                  25                  30

Glu Gln Cys Gly Tyr Pro Val Gln Arg Leu Val Ala Leu Tyr Leu Ala
        35                  40                  45

Ala Arg Leu Ser Trp Asn Gln Val Asp Gln Val Ile Arg Asn Ala Leu
```

```
            50                  55                  60
Ala Ser Pro Gly Ser Gly Gly Asp Leu Gly Glu Ala Ile Arg Glu Gln
 65                  70                  75                  80

Pro Glu Gln Ala Arg Leu Ala Leu Thr Leu Ala Ala Glu Ser Glu
                 85                  90                  95

Arg Phe Val Arg Gln Gly Thr Gly Asn Asp Glu Ala Gly Ala Ala Asn
                100                 105                 110

Gly Pro Ala Asp Ser Gly Asp Ala Leu Leu Glu Arg Asn Tyr Pro Thr
            115                 120                 125

Gly Ala Glu Phe Leu Gly Asp Gly Asp Val Ser Phe Ser Thr Arg
            130                 135                 140

Gly Thr Gln Asn Trp Thr Val Glu Arg Leu Leu Gln Ala His Arg Gln
145                 150                 155                 160

Leu Glu Glu Arg Gly Tyr Val Phe Val Gly Tyr His Gly Thr Phe Leu
                165                 170                 175

Glu Ala Ala Gln Ser Ile Val Phe Gly Gly Val Arg Ala Arg Ser Gln
                180                 185                 190

Asp Leu Asp Ala Ile Trp Arg Gly Phe Tyr Ile Ala Gly Asp Pro Ala
            195                 200                 205

Leu Ala Tyr Gly Tyr Ala Gln Asp Gln Glu Pro Asp Ala Arg Gly Arg
            210                 215                 220

Ile Arg Asn Gly Ala Leu Leu Arg Val Tyr Val Pro Arg Ser Ser Leu
225                 230                 235                 240

Pro Gly Phe Tyr Arg Thr Ser Leu Thr Leu Ala Ala Pro Glu Ala Ala
                245                 250                 255

Gly Glu Val Glu Arg Leu Ile Gly His Pro Leu Pro Leu Arg Leu Asp
                260                 265                 270

Ala Ile Thr Gly Pro Glu Glu Gly Gly Arg Leu Glu Thr Ile Leu
            275                 280                 285

Gly Trp Pro Leu Ala Glu Arg Thr Val Val Ile Pro Ser Ala Ile Pro
290                 295                 300

Thr Asp Pro Arg Asn Val Gly Gly Asp Leu Asp Pro Ser Ser Ile Pro
305                 310                 315                 320

Asp Lys Glu Gln Ala Ile Ser Ala Leu Pro Asp Tyr Ala Ser Gln Pro
                325                 330                 335

Gly Lys Pro Pro Lys Asp Glu Leu
            340

<210> SEQ ID NO 210
<211> LENGTH: 798
<212> TYPE: DNA
<213> ORGANISM: Artificial Sequence
<220> FEATURE:
<223> OTHER INFORMATION: human anti-VEGF antibody

<400> SEQUENCE: 210
atggccgata ttcaaatgac ccagagcccg agcagcctga gcgcgagcgt gggagatcgc      60
gtgaccatta cctgccgtgc gagccaggat gttagcacgg cggtcgcatg gtatcagcag     120
aaaccaggca aagcgccgaa acttctgata tactctgcgt ccttcctgta tagcggcgtg     180
ccgtcgcgtt tttcgggcag tggcagcggc acggacttta ccctgacgat atcttcctta     240
caaccggagg attttgcgac ctactactgt caacagcatt ataccacacc gccgaccttc     300
ggtcaaggca ccaaagtgga aatcaaacgc ggaggggggag tagcatcga gggccgtagc     360 ggaggtggcg ggagcgaagt gcagctggtg gaatcgggag gcggtctggt gcaacctggc     420
```

```
ggcagccttc gtctgagctg tgcggcgagc gggttcacca ttagcgatta ctggattcat    480
tgggtgcgtc aagctcccgg caaggggctg gagtgggtcg cgggcattac gcccgctggc    540
ggttacacat attatgccga cagcgtgaaa ggtcgcttta cgattagtgc ggacaccagc    600
aaaaataccg cgtacctgca gatgaatagc ctgcgtgcgg aagacacagc ggtgtattat    660
tgcgcgcgtt tcgtgttttt tctgccgtat gcgatggatt attgggggca gggcaccctt    720
gttaccgtga gctcggcgtc agcggccgca ggtgcgccgg tgccgtatcc ggatccgctg    780
gaaccgcgtg ccgcatag                                                  798
```

PHAGE-DISPLAYED SINGLE-CHAIN VARIABLE FRAGMENT LIBRARIES AND USES THEREOF

CROSS-REFERENCE TO RELATED APPLICATION

This application is a continuation-in-part of U.S. application Ser. No. 15/547,523, filed Jul. 31, 2017, which is a U.S. National Stage Filing under 35 U.S.C. 371 from International Patent Application Serial No. PCT/US2016/019128, filed Feb. 23, 2016, and published on Sep. 1, 2016, which claims the benefit of U.S. Provisional Application No. 62/120,352, filed Feb. 24, 2015, the contents of said application are incorporated herein by reference in its entirety.

BACKGROUND OF THE INVENTION

Field of the Invention

The present disclosure in general relates to the field of antibody fragment library. More particularly, the present disclosure relates to a phage-displayed single-chain variable fragment (scFv) library and the uses thereof.

Description of Related Art

An antibody, also known as an immunoglobulin, is a large Y-shape protein produced by plasma cells that is used by the immune system to identify and neutralize foreign objects, such as bacteria and viruses. The antibody recognizes a unique part of the foreign target, called an antigen. Each tip of the "Y" of an antibody contains a paratope that is specific for one particular epitope on an antigen, allowing these two structures to bind together with precision. Using this binding mechanism, an antibody can tag a microbe or an infected cell, and accordingly, facilitating the subsequent attack by other parts of the immune system, or can neutralize its target directly (for example, by blocking a part of a microbe that is essential for its invasion and survival). The production of antibodies is the main function of the humoral immune system.

Antibodies are typically made of basic structural units—each with two large heavy chains and two small light chains. There are five types of heavy chains denoted as alpha ($\alpha$), delta ($\delta$), epsilon ($\epsilon$), gamma ($\gamma$), and mu ($\mu$). The type of heavy chain present defines the isotypes of antibody; these chains are found in immunoglobulin A (IgA), immunoglobulin D (IgD), immunoglobulin E (IgE), immunoglobulin G (IgG), and immunoglobulin M (IgM) antibodies, respectively. Each heavy chain has two regions: the constant region (CH) and the variable region (VH). The constant region is identical in all antibodies of the same isotype, but differs in antibodies of different isotypes. The variable region of the heavy chain differs in antibodies produced by different B cells, but is the same for all antibodies produced by a single B cell or B cell clone that is stimulated and activated by a specific antigen. As to the light chain, it is known that there are two types of light chain, which are denoted as lambda ($\lambda$) and kappa ($\kappa$). With the similar structure of the heavy chain, each light chain has two regions: one constant region (CL) and one variable region (VL), in which the constant region is unchangeable in antibodies of the same isotype, while the variable region is different depending on the stimulated antigen.

Though the general structure of all antibodies is very similar, a small region at the tip of antibody is extremely variable, allowing millions of antibodies with slightly different tip structures (i.e., antigen-binding sites, or paratopes) to exist. This region is known as the hypervariable region or complementarity determining region (CDR). Each of these variants can bind to a different antigen, and thus, the enormous diversity of antibodies allows the immune system to recognize an equally wide variety of antigens. The large and diverse population of antibodies is generated by random combinations of a set of gene segments (i.e., variable segment, diversity segment, and joining segment) that encode different paratopes, followed by random mutations (also known as somatic hypermutations, SHMs) in this area of the antibody gene, which create further diversity.

For the preparation of antibodies, generally a native or recombinant protein or fragment thereof is used to immunize an animal, so that an antibody that can specifically recognize and bind the protein/fragment is produced in the animal. Then various technical means can be used based on corresponding requirements to obtain antibody from the animal, such as monoclonal antibody or polyclonal antibody. The production of monoclonal antibody typically relies on hybridoma techniques. In such techniques, after immunizing the animal, the cells of the animal would be taken and fused to generate an antibody-producing hybridoma, which is then cloned to construct a strain for producing antibody, and subsequently the antibody is purified and identified. Although these methods currently are widely used in the preparations of antibodies, they also have many disadvantages, such as long preparation periods that involve complicated techniques, incomplete recognition of epitopes, and high manufacturing cost etc. Further, such methods cannot be applied to all the proteins/fragments, particularly to antigens with low solubility, low immunogenicity, or antigens with toxicity, such methods would be inappropriate.

In view of the forging, there exists in the related art a need for a system and/or method for producing an antibody with binding affinity and/or specificity to a specific antigen in a more cost-efficient manner.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

As embodied and broadly described herein, one aspect of the present disclosure is directed to a phage-displayed single-chain variable fragment (scFv) library that comprises a plurality of phage-displayed scFvs. In the present library, each of the plurality of phage-displayed scFv comprises a first light chain complementarity determining region (CDR-L1), a second light chain CDR (CDR-L2), a third light chain CDR (CDR-L3), a first heavy chain CDR (CDR-H1), a second heavy chain CDR (CDR-H2), and a third heavy chain CDR (CDR-H3); in which the CDR-L1, CDR-L2, CDR-L3, CDR-H1, CDR-H2 and CDR-H3 are respectively encoded by a first to a sixth coding sequences.

According to embodiments of the present disclosure, the first coding sequence comprises the nucleic acid sequence of SEQ ID NO: 8 or 10; the second coding sequence comprises the nucleic acid sequence of SEQ ID NO: 12, 14, 16 or 18; the third coding sequence comprises the nucleic acid sequence of SEQ ID NO: 20 or 22; the fourth coding sequence comprises the nucleic acid sequence of SEQ ID NO: 24, 26, 28, 30, 32, 34, 36 or 38; the fifth coding sequence comprises the nucleic acid sequence of SEQ ID NO: 40 or 42; and the sixth coding sequence comprises the nucleic acid sequence of any of SEQ ID NOs: 45-46, 52-56, 60-62 67-70, 76-80, 91-100, 116-130 and 152-172.

In some working examples of the present disclosure, the first coding sequence has the nucleic acid sequence of SEQ ID NO: 7 or 9; the second coding sequence has the nucleic acid sequence of SEQ ID NO: 11, 13, 15 or 17; the third coding sequence has the nucleic acid sequence of SEQ ID NO: 19 or 21; the fourth coding sequence has the nucleic acid sequence of SEQ ID NO: 23, 25, 27, 29, 31, 33, 35 or 37; the fifth coding sequence has the nucleic acid sequence of SEQ ID NO: 39 or 41; and the sixth coding sequence has the nucleic acid sequence of any of SEQ ID NOs: 43-44, 47-51, 57-59, 63-66, 71-75, 81-90, 101-115 and 131-151.

In general, the phage for expressing the scFv may be an M13 phage or a T7 phage. According to one specific example, the phage is an M13 phage.

According to certain embodiments of the present disclosure, at least one of the plurality of phage-displayed scFvs is specific for an antigen selected from the group consisting of human epidermal growth factor receptor 2 (HER2), human epidermal growth factor receptor 3 (HER3), Programmed death-ligand 1 (PD-L1) and Mesothelin (MSLN).

The second aspect of the present disclosure pertains to a method for establishing the present phage-displayed scFv library. The method comprises the steps of, (1) obtaining a first nucleic acid sequence that comprises a first, a second, a third, a fourth, a fifth and a sixth gene fragments respectively encoding the CDR-L1, CDR-L2, CDR-L3, CDR-H1, CDR-H2, and CDR-H3 of an immunoglobulin gene;

(2) inserting the first nucleic acid sequence into a first phagemid vector;

(3) respectively modifying the first, second, and third gene fragments by site-directed mutagenesis to produce a variable light chain (VL) library that comprises a first group of phage-displayed scFvs with the modified CDR-L1, CDR-L2, and CDR-L3; and respectively modifying the fourth, fifth, and sixth gene fragments by site-directed mutagenesis to produce a variable heavy chain (VH) library that comprises a second group of phage-displayed scFvs with the modified CDR-H1, CDR-H2, and CDR-H3;

(4) screening the VL library with a protein L, and selecting a third group of phage-displayed scFvs therefrom; and screening the VH library with a protein A, and selecting a fourth group of phage-displayed scFvs therefrom;

(5) respectively amplifying a plurality of second nucleic acid sequences encoding the modified CDR-L1, CDR-L2, and CDR-L3 from the corresponding phages, and a plurality of third nucleic acid sequences encoding the modified CDR-H1, CDR-H2, and CDR-H3 from the corresponding phages; and (6) inserting the plurality of second and third nucleic acid sequences into a second phagemid vector so as to produce the present phage-displayed scFv library.

According to the embodiments of the present disclosure, in the step (3), the first gene fragment is modified by the nucleic acid sequence of SEQ ID NO: 7 or 9;

the second gene fragment is modified by the nucleic acid sequence of SEQ ID NO: 11, 13, 15 or 17;

the third gene fragment is modified by the nucleic acid sequence of SEQ ID NO: 19 or 21;

the fourth gene fragment is modified by the nucleic acid sequence of SEQ ID NO: 23, 25, 27, 29, 31, 33, 35 or 37;

the fifth gene fragment is modified by the nucleic acid sequence of SEQ ID NO: 39 or 41; and the sixth gene fragment is modified by the nucleic acid sequence of any of SEQ ID NOs: 43-44, 47-51, 57-59, 63-66, 71-75, 81-90, 101-115 and 131-151.

According to certain embodiments of the present disclosure, the immunoglobulin gene of the step (1) is derived from a mammalian, for example, a mouse, a rat, a hamster, a rabbit, a monkey, a goat, or a sheep. In one working example, the immunoglobulin gene is derived from the human. According to one preferred embodiment, the immunoglobulin gene encodes an antibody specific for VEGF.

Basically, the first and second phagemid vectors may be the same or different. Optionally, both the first and second phagemid vectors are derived from the M13 phage.

The third aspect of the present disclosure is directed to a method of producing a recombinant antibody from the present phage-displayed scFv library. The method comprises, (a) screening the present phage-displayed scFv library with an antigen;

(b) selecting the phages that display scFvs with binding affinity to the antigen;

(c) respectively enabling the selected phages of the step (b) to express the scFvs, which are in soluble forms;

(d) selecting one soluble scFv from the scFvs of the step (c) that exhibits high binding affinity to the antigen;

(e) extracting a phagemid DNA corresponding to the phage that expresses the selected soluble scFv of the step (d);

(f) respectively amplifying a first nucleic acid sequence that encodes the CDR-H1, CDR-H2, and CDR-H3, and a second nucleic acid sequence that encodes the CDR-L1, CDR-L2, and CDR-L3 by polymerase chain reaction (PCR) using the phagemid DNA of the step (e) as a template; and (g) inserting the first and second nucleic acid sequences into an expression vector that comprises a third and a fourth nucleic acid sequences, wherein the third nucleic acid sequence encodes the constant region of the heavy chain of an immunoglobulin, and the fourth nucleic acid sequence encodes the constant region of the light chain of the immunoglobulin; and (h) transfecting a host cell with the expression vector of the step (g) that comprises the first, second, third, and fourth nucleic acid sequences so as to produce the present recombinant antibody.

In the embodiment of the present disclosure, the first nucleic acid sequence is disposed at the upstream of the third nucleic acid sequence, and the second nucleic acid sequence is disposed at the upstream of the fourth nucleic acid sequence.

Depending on intended purposes, the immunoglobulin of the step (g) may be IgG, IgA, IgD, IgE, or IgM. According to certain embodiments of the present disclosure, the immunoglobulin is IgG.

In one embodiment of the present disclosure, the host cell of the step (h) is a mammalian cell.

The antigen for screening and selecting the scFvs in the steps (a) and (b) may be HER2, HER3, PD-L1 or MSLN.

The fourth aspect of the present disclosure pertains to a recombinant antibody prepared from the present phage-displayed scFv library. According to the embodiments of the present disclosure, the CDR-L1, CDR-L2, CDR-L3, CDR-H1, CDR-H2 and CDR-H3 of the recombinant antibody are respectively encoded by a first to a sixth coding sequences.

According to embodiments of the present disclosure, the first coding sequence comprises the nucleic acid sequence of SEQ ID NO: 8 or 10; the second coding sequence comprises the nucleic acid sequence of SEQ ID NO: 12, 14, 16 or 18; the third coding sequence comprises the nucleic acid sequence of SEQ ID NO: 20 or 22; the fourth coding sequence comprises the nucleic acid sequence of SEQ ID NO: 24, 26, 28, 30, 32, 34, 36 or 38; the fifth coding sequence comprises the nucleic acid sequence of SEQ ID NO: 40 or 42; and the sixth coding sequence comprises the nucleic acid sequence of any of SEQ ID NOs: 45-46, 52-56, 60-62 67-70, 76-80, 91-100, 116-130 and 152-172.

According to some working examples of the present disclosure, the first coding sequence has the nucleic acid sequence of SEQ ID NO: 7 or 9; the second coding sequence has the nucleic acid sequence of SEQ ID NO: 11, 13, 15 or 17; the third coding sequence has the nucleic acid sequence of SEQ ID NO: 19 or 21; the fourth coding sequence has the nucleic acid sequence of SEQ ID NO: 23, 25, 27, 29, 31, 33, 35 or 37; the fifth coding sequence has the nucleic acid sequence of SEQ ID NO: 39 or 41; and the sixth coding sequence has the nucleic acid sequence of any of SEQ ID NOs: 43-44, 47-51, 57-59, 63-66, 71-75, 81-90, 101-115 and 131-151.

According to one specific example of the present disclosure,
the variable region of light chain (VL region) and the variable region of heavy chain (VH region) of the recombinant antibody respectively comprise the amino acid sequences of SEQ ID NOs: 173 and 174;

the VL region and the VH region of the recombinant antibody respectively comprise the amino acid sequences of SEQ ID NOs: 175 and 176;

the VL region and the VH region of the recombinant antibody respectively comprise the amino acid sequences of SEQ ID NOs: 177 and 178;

the VL region and the VH region of the recombinant antibody respectively comprise the amino acid sequences of SEQ ID NOs: 179 and 180;

the VL region and the VH region of the recombinant antibody respectively comprise the amino acid sequences of SEQ ID NOs: 181 and 182;

the VL region and the VH region of the recombinant antibody respectively comprise the amino acid sequences of SEQ ID NOs: 183 and 184;

the VL region and the VH region of the recombinant antibody respectively comprise the amino acid sequences of SEQ ID NOs: 185 and 186;

the VL region and the VH region of the recombinant antibody respectively comprise the amino acid sequences of SEQ ID NOs: 187 and 188;

the VL region and the VH region of the recombinant antibody respectively comprise the amino acid sequences of SEQ ID NOs: 189 and 190;

the VL region and the VH region of the recombinant antibody respectively comprise the amino acid sequences of SEQ ID NOs: 191 and 192; or the VL region and the VH region of the recombinant antibody respectively comprise the amino acid sequences of SEQ ID NOs: 193 and 194.

Also disclosed herein is a method for treating a cancer (i.e., the cancer having HER2 expressed thereon/therein) in a subject; the method comprises administering to the subject an effective amount of the present recombinant antibody. According to one embodiment of the present disclosure, the treatment of the present recombinant antibody efficiently inhibits the tumor growth. Preferably, the subject is a human.

Many of the attendant features and advantages of the present disclosure will becomes better understood with reference to the following detailed description considered in connection with the accompanying drawings.

BRIEF DESCRIPTION OF THE DRAWINGS

The present description will be better understood from the following detailed description read in light of the accompanying drawings, where.

DETAILED DESCRIPTION OF THE INVENTION

Figure 1:
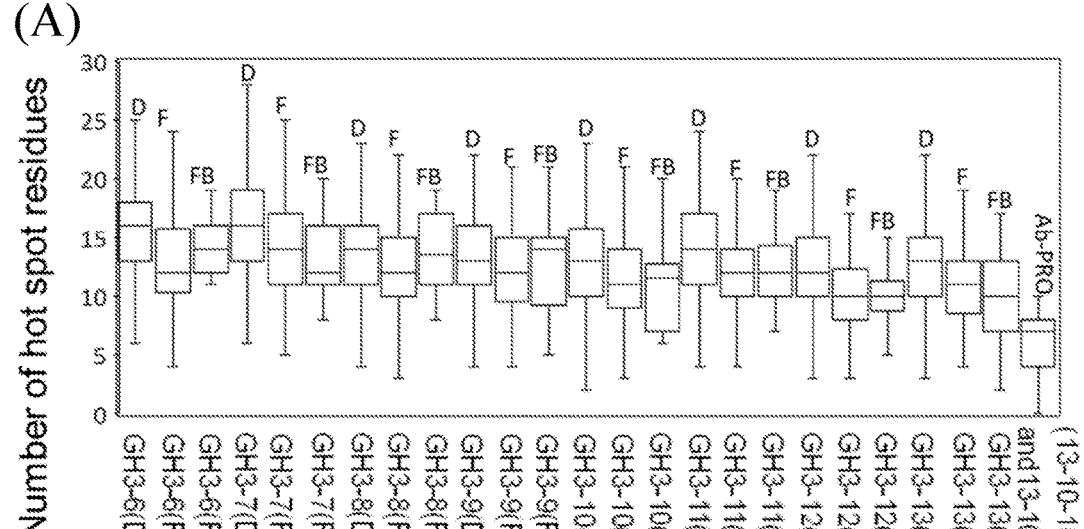
FIG. 1 is the data depicting the number of hot spot residues in CDRs of specified scFv sets according to one embodiment of the present disclosure. Panel A: The distributions of the numbers of the hot spot residues in CDR-L1, CDR-L2, CDR-L3, CDR-H1 and CDR-H2 of specified scFv sets. Panel B: The distributions of hot spot residues in CDR-H3 of specified scFv sets. scFv set (D): 200 randomly selected theoretical scFv sequences based on the CDR designs; scFv set (F): scFv exhibiting binding affinity to protein A and protein L; scFv set (FB): scFv exhibiting binding affinity to protein A, protein L and the specified antigen listed in Table 2.
Figure 1:
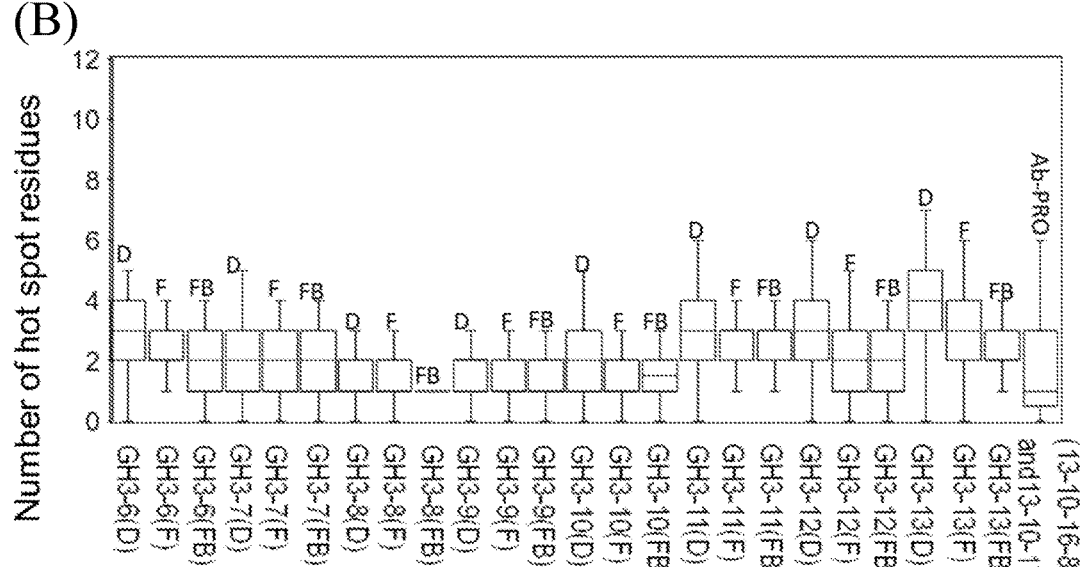

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

I. Definition

For convenience, certain terms employed in the specification, examples and appended claims are collected here. Unless otherwise defined herein, scientific and technical terminologies employed in the present disclosure shall have the meanings that are commonly understood and used by one of ordinary skill in the art. Also, unless otherwise required by context, it will be understood that singular terms shall include plural forms of the same and plural terms shall include the singular. Specifically, as used herein and in the claims, the singular forms "a" and "an" include the plural reference unless the context clearly indicates otherwise. Also, as used herein and in the claims, the terms "at least one" and "one or more" have the same meaning and include one, two, three, or more.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about". Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

The term "antigen" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleic acid sequence or a partial nucleic acid sequence encoding a protein that elicits an immune response, therefore encodes an "antigen" as that term is used herein. Furthermore, one skilled in the art will understand that an antigen needs not be encoded solely by a full length nucleic acid sequence of a gene; it can also be encoded by partial nucleic acid sequences of more than one gene and that these nucleic acid sequences are arranged in various combinations to elicit the desired immune response. Moreover, a skilled artisan will understand that an antigen needs not be encoded by a "gene" at all; it is readily apparent that an antigen can be synthesized or can be derived from a biological sample. Such a biological sample can include, but is not limited to, a tissue sample, a tumor sample, a cell or a biological fluid.

The term "antibody" is used in the broadest sense and specifically covers monoclonal antibodies (including full length monoclonal antibodies), polyclonal antibodies, multi-specific antibodies (e.g., bi-specific antibodies), and antibody fragments so long as they exhibit the desired biological activity. "Antibody fragments" comprise a portion of a full length antibody, generally the antigen binding or variable region thereof. Examples of antibody fragments include antigen-binding fragment (Fab), Fab', F(ab')2, and Fv fragments; diabodies; linear antibodies; single-chain antibody molecules; and multi-specific antibodies formed from antibody fragments.

The term "antibody library" or "scFv library" refers to a collection of antibodies and/or antibody fragments (e.g., scFvs) displayed for screening and/or combination into full antibodies. The antibodies and/or antibody fragments may be displayed on a ribosome; on a phage; or on a cell surface, in particular a yeast cell surface.

As used herein, the term "single-chain variable fragment" or "scFv" is a fusion protein comprising the VH region and VL region of an immunoglobulin, in which the VH and VL regions are covalently linked to form a VH::VL heterodimer. The VH and VL regions are either joined directly or joined by a peptide-encoding linker, which connects the N-terminus of the VH region with the C-terminus of the VL region, or the C-terminus of the VH region with the N-terminus of the VL region. The linker is usually rich in glycine for flexibility, as well as serine or threonine for solubility. Despite removal of the constant regions and the introduction of a linker, scFv proteins retain the specificity of the original immunoglobulin. Single chain Fv polypeptide antibodies can be expressed from a nucleic acid including VH- and VL-encoding sequences.

The term "complementarity determining region" (CDR) used herein refers to the hypervariable region of an antibody molecule that forms a surface complementary to the 3-dimensional surface of a bound antigen. Proceeding from N-terminus to C-terminus, each of the antibody heavy and light chains comprises three CDRs (CDR 1, CDR 2, and CDR3). A HLA-DR antigen-binding site, therefore, includes a total of six CDRs that comprise three CDRs from the variable region of a heavy chain and three CDRs from the variable region of a light chain.

The term "canonical structure" (CS) as understood by those of ordinary skill in the art, refers to the main chain conformation that is adopted by the antigen binding (i.e., CDR) loops. From comparative structural studies, it has been found that five of the six antigen binding loops have only a limited repertoire of available conformations. Each canonical structure can be characterized by the torsion angles of the polypeptide backbone.

The term "$EC_{50}$," as used herein, refers to the concentration of an antibody or an antigen-binding portion thereof, which induces a response, either in an in vitro or an in vivo assay, which is 50% of the maximal response, i.e., halfway between the maximal response and the baseline.

The term "phagemid" refers to a vector, which combines attributes of a bacteriophage and a plasmid. A bacteriophage is defined as any one of a number of viruses that infect bacteria.

The terms "nucleic acid sequence" or "nucleotide sequence" can be used interchangeably and are understood to mean, according to the present disclosure, either a double-stranded DNA, a single-stranded DNA or a product of transcription of said DNA (e.g., RNA molecule). It should also be understood that the present disclosure does not relate to genomic polynucleic acid sequences in their natural environment or natural state. The nucleic acid, polynucleotide, or nucleic acid sequences of the invention can be isolated, purified (or partially purified), by separation methods including, but not limited to, ion-exchange chromatography, molecular size exclusion chromatography, or by genetic engineering methods such as amplification, subtractive hybridization, cloning, sub-cloning or chemical synthesis, or combinations of these genetic engineering methods.

All degenerate nucleotide sequences are included within the scope of the invention as long as the peptide/polypeptide/protein (e.g., the present CDR, or the variable region of heavy chain or light chain) encoded by the nucleotide sequence maintains the desired activity or function. The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (i.e., GAU and GAC triplets each encode Asp).

The terms "coding sequence" refers to nucleotide sequences and nucleic acid sequences, including both RNA and DNA, that encode genetic information for the synthesis of an RNA, a protein, or any portion of an RNA or protein.

Nucleotide sequences that are not naturally part of a particular organism's genome are referred to as "foreign nucleotide sequences", "heterologous nucleotide sequences", or "exogenous nucleotide sequences". "Heterologous proteins" are proteins encoded by foreign, heterologous or exogenous nucleotide sequences and therefore are often not naturally expressed in the cell. A nucleotide sequence that has been isolated and then reintroduced into the same type (e.g., same species) of organism is not considered to be a naturally occurring part of a particular organism's genome and is therefore considered exogenous or heterologous.

The term "similar" or "similarity" as used herein describes the relationship between different nucleic acid or amino acid sequences in which the sequences are related by partial sequence identity or sequence similarity at one or more blocks or regions within the sequence. Such similar amino acid residues may be either identical between different amino acid sequences, or represent conservative amino acid substitutions between different sequences.

The term "subject" refers to a mammal including the human species that is treatable with methods of the present invention. The term "subject" is intended to refer to both the male and female gender unless one gender is specifically indicated.

II. Description of The Invention

The object of the present disclosure aims at providing a phage-displayed scFv library that is capable of recognizing and binding to various antigens, such as HER2, thereby preventing and/or treating the diseases (e.g., cancers) associated with/caused by the antigens. The scFv library comprises a plurality of phage-displayed scFvs, all of which are characterized in having a specific CS combination and a specific sequence in each CDR. Accordingly, an antibody exhibiting binding affinity and specificity to a desired antigen can be easily generated from the present library by antigen screening without the need of repeating the routine steps, such as immunizing a host animal and/or producing a hybridoma, thus may substantially shorten the time and efforts generally required for the production of an antibody via a conventional manner. Accordingly, the present method provides a means to generate various antigen-specific antibodies in accordance with the need of an experimental research and/or clinical applications.

(i) Method of Establishing the Present Phage-Displayed scFv Library

For the purpose of establishing the present phage-displayed scFv library, a human germline sequence is modified by specific primers so as to diversify the CDR sequences thereof. Specifically, the method for establishing the present phage-displayed scFv library comprises the steps of, (1) obtaining a first nucleic acid sequence that comprises a first, a second, a third, a fourth, a fifth and a sixth gene fragments respectively encoding the CDR-L1, CDR-L2, CDR-L3, CDR-H1, CDR-H2, and CDR-H3 of an immunoglobulin gene;

(2) inserting the first nucleic acid sequence into a first phagemid vector;

(3) respectively modifying the first, second, and third gene fragments by site-directed mutagenesis to produce a VL library that comprises a first group of phage-displayed scFvs with the modified CDR-L1, CDR-L2, and CDR-L3; and respectively modifying the fourth, fifth, and sixth gene fragments by site-directed mutagenesis to produce a VH library that comprises a second group of phage-displayed scFvs with the modified CDR-H1, CDR-H2, and CDR-H3;

(4) screening the VL library with a protein L, and selecting a third group of phage-displayed scFvs therefrom that exhibit binding affinity to the protein L; and screening the VH library with a protein A, and selecting a fourth group of phage-displayed scFvs therefrom that exhibit binding affinity to the protein A;

(5) respectively amplifying a plurality of second nucleic acid sequences encoding the modified CDR-L1, CDR-L2, and CDR-L3 from the corresponding phages, and a plurality of third nucleic acid sequences encoding the modified CDR-H1, CDR-H2, and CDR-H3 from the corresponding phages; and (6) inserting the plurality of second and third nucleic acid sequences into a second phagemid vector so as to produce the present phage-displayed scFv library.

In the step (1), a first nucleic acid sequence, which serves as the backbone of the scFv of the present scFv library, is first obtained. According to some embodiments of the present disclosure, the first nucleic acid sequence is amplified from human IGKV1-NL1*01/IGHV3-23*04 germline sequence via PCR. Alternatively, the first nucleic acid sequence may be synthesized by DNA synthesis technique; as known by the skilled artisan, the synthesis step is performed in vitro without the need for initial template DNA samples. According to the embodiments of the present disclosure, the first nucleic acid sequence is synthesized least 90% identical to SEQ ID NO: 210 that encodes CDR-L1, CDR-L2, CDR-L3, CDR-H1, CDR-H2, and CDR-H3 of human anti-VEGF antibody. According to the embodiments of the present disclosure, the first nucleic acid sequence comprises a first and a second restriction enzyme sites that facilitate the insertion of the synthetic first nucleic acid sequence into the first phagemid vector as described In the step (2). In one embodiment, the first restriction enzyme site is SfiI, and the second restriction enzyme site is NotI.

In the step (2), the synthetic first nucleic acid sequence is inserted into the first phagemid vector via the first and second restriction enzyme sites. The first phagemid vector may be derived from M13 phage or T7 phage. According to one working example, the first phagemid vector is derived from M13 phage.

To diversify the scFvs displayed by the phages, the first to sixth gene fragments respectively encoding the CDR-L1, CDR-L2, CDR-L3, CDR-H1, CDR-H2, and CDR-H3 of the immunoglobulin gene (e.g., SEQ ID NO: 210) are modified In the step (3), in which the modification is performed by site-directed mutagenesis, a molecular biology method widely used by one of ordinary skill in the art to make specific and intentional changes to the genetic (i.e., DNA and RNA) sequence. Generally, the site-directed mutagenesis is exerted by a primer, which contains a desired mutation and the sequences complementary to the template DNA around the mutation site so that the primer can hybridize with the gene of interest; the mutation can be a single base change (a point mutation), multiple base changes, deletion, or insertion.

According to certain embodiments of the present disclosure, the first gene fragment is modified by the DNA segment having the nucleic acid sequence of SEQ ID NO: 7 or 9; the second gene fragment is modified by the DNA segment having the nucleic acid sequence of 11, 13, 15 or 17; and the third gene fragment is modified by the DNA segment having the nucleic acid sequence of 19 or 21. The first to the third gene fragments may be modified sequentially or simultaneously. According to one working example of the present disclosure, the first to the third gene fragments are modified simultaneously. After the modification, the first gene fragment comprises the nucleic acid sequence of SEQ ID NO: 8 or 10; the second gene fragment comprises the nucleic acid sequence of SEQ ID NO: 12, 14, 16 or 18; and the third gene fragment comprises the nucleic acid sequence of SEQ ID NO: 20 or 22. In one working example, the first gene fragment comprises the nucleic acid sequence of SEQ ID NO: 7 or 9; the second gene fragment comprises the nucleic acid sequence of SEQ ID NO: 11, 13, 15 or 17; and the third gene fragment comprises the nucleic acid sequence of SEQ ID NO: 19 or 21. The phage-displayed scFvs with the modified CDR-L1, CDR-L2, and CDR-L3 constitute the VL library.

Regarding the fourth to the sixth gene fragments, they are modified by the similar method, in which the fourth gene fragment is modified by the DNA segment having the nucleic acid sequence of 23, 25, 27, 29, 31, 33, 35 or 37; the fifth gene fragment is modified by the DNA segment having the nucleic acid sequence of 39 or 41; and the sixth gene fragment is modified by the DNA segment having the nucleic acid sequence of any of SEQ ID NOs: 43-44, 47-51, 57-59, 63-66, 71-75, 81-90, 101-115 and 131-151 (i.e., the DNA segment having the nucleic acid sequence of SEQ ID NO: 43, 44, 47, 48, 49, 50, 51, 57, 58, 59, 63, 64, 65, 66, 71, 72, 73, 74, 75, 81, 82, 83, 84, 85, 86, 87, 88, 89, 90, 101, 102, 103, 104, 105, 106, 107, 108, 109, 110, 111, 112, 113, 114, 115, 131, 132, 133, 134, 135, 136, 137, 138, 139, 140, 141, 142, 143, 144, 145, 146, 147, 148, 149, 150 or 151). As mentioned above, the fourth to the sixth gene fragments may be modified sequentially or simultaneously. According to one working example of the present disclosure, the fourth to the sixth gene fragments are modified simultaneously. After the modification, the fourth gene fragment comprises the nucleic acid sequence of SEQ ID NO: 24, 26, 28, 30, 32, 34, 36 or 38; the fifth gene fragment comprises the nucleic acid sequence of SEQ ID NO: 40 or 42; and the sixth gene fragment comprises the nucleic acid sequence of any of SEQ ID NOs: 45-46, 52-56, 60-62 67-70, 76-80, 91-100, 116-130 and 152-172 (i.e., the nucleic acid sequence of SEQ ID NO: 45, 46, 52, 53, 54, 55, 56, 60, 61, 62, 67, 68, 69, 70, 76, 77, 78, 79, 80, 91, 92, 93, 94, 95, 96, 97, 98, 99, 100, 116, 117, 118, 119, 120, 121, 122, 123, 124, 125, 126, 127, 128, 129, 130, 152, 153, 154, 155, 156, 157, 158, 159, 160, 161, 162, 163, 164, 165, 166, 167, 168, 169, 170, 171 or 172). In one working example, the fourth gene fragment comprises the nucleic acid sequence of SEQ ID NO: 23, 25, 27, 29, 31, 33, 35 or 37; the fifth gene fragment comprises the nucleic acid sequence of SEQ ID NO: 39 or 41; and the sixth gene fragment comprises the nucleic acid sequence of any of SEQ ID NOs: 43-44, 47-51, 57-59, 63-66, 71-75, 81-90, 101-115 and 131-151. The phage-displayed scFvs with the modified CDR-H1, CDR-H2, and CDR-H3 constitute the VH library.

The nucleotide sequences of SEQ ID NOs: 1-172 are represented by TUB (international unit of biochemistry) code, widely used by one of ordinary skill in the art, in which A represents adenine; C represents cytosine; G represents guanine; T represents thymine; B represents any nucleotide of C, G or T; D represents any nucleotide of A, T, or G; H represents any nucleotide of A, C, or T; K represents nucleotide G or T; M represents A or C; N represents any nucleotide of A, T, C, or G; R represents nucleotide A or G; S represents nucleotide G or C; V represents any nucleotide of A, C, or G; W represents nucleotide A or T; and Y represents nucleotide C or T.

Since the sequence mutation might affect the folding of scFv, the VL and VH libraries are respectively screened with protein L and protein A as described In the step (4). As known by the skilled artisan, protein L is isolated from bacterial species *Peptostreptococcus magnus* and exhibits binding affinity to the light chain of an immunoglobulin; and protein A is isolated from the cell wall of bacterium *Staphylococcus aureus* and possesses binding affinity to the heavy chain of an immunoglobulin. In practice, the protein L and the protein A are respectively immobilized on a matrix (such as an agarose resin, and polyacrylamide) followed by respectively mixing with the phage-displayed scFvs of VL and VH libraries. The well-folded scFv would bind to the immobilized proteins, and can be collected by elution buffer, which generally is an acidic solution (such as glycine solution, pH 2.2) so as to disrupt the binding between immobilized protein and phage-display scFv. Accordingly, a third group of phage-displayed scFvs that possess well-folded light chains and binding affinity towards protein L can be selected from the VL library; and a fourth group of phage-displayed scFvs that possess well-folded heavy chains and binding affinity towards protein A can be selected from the VH library.

In the step (5), the nucleic acid sequences corresponding to the third and fourth groups of phages are extracted followed by the amplification and assembly by PCR as described in Materials and Methods of the present disclosure. The construction method is described in more detail in the co-pending U.S. application Ser. No. 15/547,523, the entire contents of which are incorporated by reference herein. Depending on intended purposes, the phagemid may be extracted by lysing the phage; alternatively, the phagemid may be obtained from a bacterial clone (i.e., the phagemid-containing bacterial clone). The extraction of phage DNA from the phage or bacterial clone could be achieved via any conventional DNA extraction technique; for example, the phenol/chloroform assay, and detergent (e.g., sodium dodecyl sulfate, Tween-20, NP-40, and Triton X-100)/acetic acid assay.

Then, in the step (6), the assembled product is inserted into a second phagemid vector so as to produce a recombinant phagemid. The second phagemid vector can be derived from M13 phage or T7 phage. According to one working example, it is derived from M13 phage. The recombinant phagemid is then introduced into a host cell. In general, the phagemid can be introduced into the host cell by transformation or electroporation. After the recombinant phagemid is introduced into the host cell, each transformed host cell comprising one recombinant phagemid would form one colony on the culture plate. According to the embodiments, the host cell is a bacterial; for example, an *E. coli* cell; and a total of about $10^9$ independent colonies are obtained from the step (6), all of which were scraped off the plates and storage in a storage buffer as a stock of the phage-displayed scFv library of the present disclosure.

It should be noted that the first and second phagemid vector are not necessary to be the same. According to one embodiment of the present disclosure, both the first and second phagemid vectors are derived from M13 phage.

(ii) Phage-Displayed scFv Library Established by the Method of Part (i)

The established phage-displayed scFv library comprises a plurality of phage-displayed scFvs, in which each of the plurality of phage-displayed scFvs comprises a CDR-H1, a CDR-H2, a CDR-H3, a CDR-L1, a CDR-L2, and a CDR-L3, wherein each of the CDR-H1, CDR-L2 and CDR-L3 has a type 1 CS, the CDR-H2 has a type 2 CS, and the CDR-L1 has a type 3 or type 4 CS.

According to the embodiments of the present disclosure, the CDR-L1 of each scFv is encoded by a first coding sequence, which comprises the nucleic acid sequence of SEQ ID NO: 8 or 10. In certain preferred examples, the first coding sequence has the nucleic acid sequence of SEQ ID NO: 7 or 9.

The CDR-L2 of each scFv is encoded by a second coding sequence, which comprises the nucleic acid sequence of SEQ ID NO: 12, 14, 16 or 18. According to some working examples, the second coding sequence has the nucleic acid sequence of SEQ ID NO: 11, 13, 15 or 17.

The CDR-L3 of each scFv is encoded by a third coding sequence, which comprises the nucleic acid sequence of SEQ ID NO: 20 or 22. In some examples, the third coding sequence has the nucleic acid sequence of SEQ ID NO: 19 or 21.

The CDR-H1 of each scFv is encoded by a fourth coding sequence, which comprises the nucleic acid sequence of SEQ ID NO: 24, 26, 28, 30, 32, 34, 36 or 38. According to some preferred examples, the fourth coding sequence has the nucleic acid sequence of SEQ ID NO: 23, 25, 27, 29, 31, 33, 35 or 37.

The CDR-H2 of each scFv is encoded by a fifth coding sequence, which comprises the nucleic acid sequence of SEQ ID NO: 40 or 42. Preferably, the fifth coding sequence has the nucleic acid sequence of SEQ ID NO: 39 or 41.

Regarding the CDR-H3 of each scFv, it is encoded by a sixth coding sequence comprising the nucleic acid sequence of any of SEQ ID NOs: 45-46, 52-56, 60-62 67-70, 76-80, 91-100, 116-130 and 152-172. Preferably, the sixth coding sequence has the nucleic acid sequence of any of SEQ ID NOs: 43-44, 47-51, 57-59, 63-66, 71-75, 81-90, 101-115 and 131-151.

According to some embodiments, each phage of the present phage-displayed scFv library harbors one single phagemid.

According to working examples of the present disclosure, at least one of the plurality of phage-displayed scFvs exhibits binding affinity and/or specificity to an antigen selected from the group consisting of HER2, HER3, PD-L1 and MSLN. According to one specific example, at least one of the plurality of the phage-displayed scFvs exhibits binding affinity and/or specificity to HER2.

The scFvs displayed by the present phage-displayed scFv library are well-folded; particularly, they can be expressed on phage surfaces, or secreted as soluble form.

(iii) Method of Producing Recombinant Antibodies by Use of the Present scFv Library The phage-displayed scFv library established in part (ii) of the present disclosure is useful in efficiently producing a recombinant antibody exhibiting binding affinity and/or specificity to an antigen. Specifically, the method of using the present phage-displayed scFv library to produce the recombinant antibody comprises, (a) screening the present phage-displayed scFv library with the antigen;

(b) selecting phages that display scFvs with binding affinity to the antigen;

(c) respectively enabling the selected phages of the step (b) to express the scFvs, which are in soluble forms;

(d) selecting one soluble scFv from the scFvs of the step (c) that exhibits high binding affinity to the antigen;

(e) extracting a phagemid DNA corresponding to the phage that expresses the selected soluble scFv of the step (d);

(f) respectively amplifying a first nucleic acid sequence that encodes the CDR-H1, CDR-H2, and CDR-H3, and a second nucleic acid sequence that encodes the CDR-L1, CDR-L2, and CDR-L3 by PCR using the phagemid DNA of the step (e) as a template (g) inserting the first and second nucleic acid sequences into an expression vector that comprises a third and a fourth nucleic acid sequences, wherein the third nucleic acid sequence encodes the constant region of the heavy chain of an immunoglobulin, and the fourth nucleic acid sequence encodes the constant region of the light chain of the immunoglobulin; and (h) transfecting a host cell with the expression vector of the step (g) that comprises the first, second, third, and fourth nucleic acid sequences so as to produce the present recombinant antibody.

In the step (a), the present phage-displayed scFv library is first screened with the antigen. With the similar screening method performed in afore-mentioned step (4) of part (i) of the present disclosure, the antigen may be immobilized on a matrix (such as an agarose resin, and polyacrylamide) and mixed with the present phage-displayed scFv library. According to the embodiments of the present disclosure, the antigen can be HER2, HER3, PD-L1 or MSLN. In one specific embodiment, the antigen is HER2.

In the step (b), the phage-displayed scFv that exhibit binding affinity to the antigen could be obtained by an elution buffer, which generally is an acidic solution (such as glycine solution, pH 2.2) so as to disrupt the binding between immobilized protein and phage-display antibody.

In the step (c), to exclude the possibility that the binding of antigen is mediated by the phage, rather than the antibody, the phage-displayed scFv selected from the step (b) are respectively expressed as their secreted soluble forms. According to the embodiment of the present disclosure, the second and third nucleic acids constructed in the second phagemid as described in the step (6) of part (i) of the present disclosure are driven by a lactose operon (lac operon); as known by one skilled artisan, the lac operon would be induced by an isopropyl-thio-β-D-galactoside (IPTG) that then drives the expression of the down-stream genes (i.e., the second and third nucleic acid sequences). The produced scFv are then secreted into the supernatant of culture medium and could be collected thereof.

Next, in the step (d), the scFvs produced in the step (c) are screened by the antigen. With the similar screening method performed in the step (a), the antigen is first immobilized on a matrix (such as an agarose resin, and polyacrylamide) and then mixed with the scFvs. The scFv exhibiting high binding affinity and/or specificity to the antigen is selected. In one specific example, the antigen is HER2.

The phagemid DNA corresponding to the phage that expresses the soluble scFv selected in the step (d) is then extracted as described in the step (e). As mentioned above, the phagemid DNA may be extracted by lysing the phage or the bacterial clone (i.e., the phagemid-containing bacterial clone), and the lysis and extraction could be performed via any conventional DNA extraction technique; for example, the phenol/chloroform assay, and detergent (e.g., sodium-dodecyl sulfate, Tween-20, NP-40, and Triton X-100)/acetic acid assay.

In the step (f), the phagemid DNA extracted in the step (e) serves as a template to respectively amplify the first nucleic acid sequence encoding the CDR-H1, CDR-H2 and CDR-H3 of the phagemid DNA, and the second nucleic acid sequence encoding the CDR-L1, CDR-L2, and CDR-L3 of the phagemid DNA by PCR using specific primers as described in Materials and Methods of the present disclosure. The construction method is described in more detail in the co-pending U.S. application Ser. No. 15/547,523.

In the step (g), the amplified first and second nucleic acid sequences are cloned into an expression vector, which comprises a third nucleic acid sequence encoding the constant regions of the heavy chain of an immunoglobulin, and a fourth nucleic acid sequence encoding the constant regions of the light chain of the immunoglobulin. As could be appreciated, the immunoglobulin may be IgG, IgA, IgD, IgE, or IgM. In one preferred embodiment of the present disclosure, the immunoglobulin is IgG. The primers and procedures for constructing the expression vector is described in Materials and Methods of the present disclosure and/or co-pending U.S. application Ser. No. 15/547,523 cited hereinabove. The entirety of the application is incorporated herein by reference. Structurally, the constructed expression vector comprises in sequence: a first human cytomegalovirus (CMV) promoter, a signal peptide of IgG light chain, the second nucleic acid sequence, CL, a first BGH-polyA signal, a second human CMV promoter, a signal peptide of IgG heavy chain, the first nucleic acid sequence, CH, and a second BGH-polyA signal, in which the second nucleic acid sequence and CL are driven by the first human CMV promoter so as to express the light chain of the recombinant antibody, and the first nucleic acid sequence and CH are driven by the second human CMV promoter to express the heavy chain of the recombinant antibody.

Finally, in the step (h), the expression vector constructed in the step (g) is transfected into a host cell so as to produce the present recombinant antibody. The commonly used host cell is a mammalian cell such as a HEK293 cell. The transfection can be performed by any method familiar by one skilled artisan, including chemical-based method (e.g., calcium phosphate, liposome, and cationic polymer), non-chemical method (e.g., electroporation, cell squeezing, sonoporation, optical transfection, protoplast fusion, and hydrodynamic delivery), particle-based method (e.g. gene gun, magnetofection, and impalefection), and viral method (e.g., adenoviral vector, sindbis viral vector, and lentiviral vector). The thus-produced recombinant antibody is secreted into the supernatant of the culture medium, and can be purified therefrom by any purification method familiar by any skilled person; for example, the purification can be achieved by affinity binding with protein A or protein G.

(iv) Antibodies Produced by the Present scFv Library and Uses Thereof

Based on the sequence diversity of the CDRs, both the scFv antibody selected from the present scFv library and the recombinant antibody produced by the present scFv library exhibit binding affinity and/or specificity to a variety of antigens, including protein antigens and peptide antigens. According to some embodiments of the present disclosure, the scFv/recombinant antibody exhibits binding affinity and/ or specificity to HER2, HER3, PD-L1 and/or MSLN.

According to the embodiments of the present disclosure, the present scFv/recombinant antibody comprises, (1) a CDR-L1 that has a type 3 or type 4 CS and is encoded by a first coding sequence comprising the nucleic acid sequence of SEQ ID NO: 8 or 10; (2) a CDR-L2 that has a type 1 CS and is encoded by a second coding sequence comprising the nucleic acid sequence of SEQ ID NO: 12, 14, 16 or 18; (3) a CDR-L3 that has a type 1 CS and is encoded by a third coding sequence comprising the nucleic acid sequence of SEQ ID NO: 20 or 22; (4) a CDR-H1 that has a type 1 CS and is encoded by a fourth coding sequence comprising the nucleic acid sequence of SEQ ID NO: 24, 26, 28, 30, 32, 34, 36 or 38; (5) a CDR-H2 that has a type 2 CS and is encoded by a fifth coding sequence comprising the nucleic acid sequence of SEQ ID NO: 40 or 42; and (6) a CDR-H3 that is encoded by a sixth coding sequence comprising the nucleic acid sequence of any of SEQ ID NOs: 45-46, 52-56, 60-62 67-70, 76-80, 91-100, 116-130 and 152-172.

Preferably, the first coding sequence for the expression of CDR-L1 has the nucleic acid sequence of SEQ ID NO: 7 or 9; the second coding sequence for the expression of CDR-L2 has the nucleic acid sequence of SEQ ID NO: 11, 13, 15 or 17; the third coding sequence for the expression of CDR-L3 has the nucleic acid sequence of SEQ ID NO: 19 or 21; the fourth coding sequence for the expression of CDR-H1 has the nucleic acid sequence of SEQ ID NO: 23, 25, 27, 29, 31, 33, 35 or 37; the fifth coding sequence for the expression of CDR-H2 has the nucleic acid sequence of SEQ ID NO: 39 or 41; and the sixth coding sequence for the expression of CDR-H3 has the nucleic acid sequence of any of SEQ ID NOs: 43-44, 47-51, 57-59, 63-66, 71-75, 81-90, 101-115 and 131-151.

According to certain embodiments of the present disclosure, the VL region of the present scFv/recombinant antibody comprises the amino acid sequence at least 90% (i.e., 90%, 91%, 92%, 93%, 94%, 95%, 96%, 97%, 98%, 99% or 100%) identical to SEQ ID NO: 173, 175, 177, 179, 181, 183, 185, 187, 189, 191 or 193; and the VH region of the present scFv/recombinant antibody comprises the amino acid sequence at least 90% (i.e., 90%, 91%, 92%, 93%, 94%, 95%, 96%, 97%, 98%, 99% or 100%) identical to SEQ ID NO: 174, 176, 178, 180, 182, 184, 186, 188, 190, 192 or 194. In one preferred example, the VL region of the present scFv/recombinant antibody comprises the amino acid sequence 100% identical to SEQ ID NO: 173, 175, 177, 179, 181, 183, 185, 187, 189, 191 or 193; and the VH region of the present scFv/recombinant antibody comprises the amino acid sequence 100% identical to SEQ ID NO: 174, 176, 178, 180, 182, 184, 186, 188, 190, 192 or 194.

According to some working examples of the present disclosure, 11 recombinant antibodies are produced by the present method, in which the VL and VH regions of antibody 30CHS-12 respectively comprise the amino acid sequences of SEQ ID NOs: 173 and 174; the VL and VH regions of antibody 30CHS-13 respectively comprise the amino acid sequences of SEQ ID NOs: 174 and 175; the VL and VH regions of antibody 30CHS-41 respectively comprise the amino acid sequences of SEQ ID NOs: 176 and 178; the VL and VH regions of antibody 35CPT-9 respectively comprise the amino acid sequences of SEQ ID NOs: 179 and 180; the VL and VH regions of antibody 35WYK-9 respectively comprise the amino acid sequences of SEQ ID NOs: 181 and 182; the VL and VH regions of antibody 35WYK-16 respectively comprise the amino acid sequences of SEQ ID NOs: 183 and 184; the VL and VH regions of antibody 29TYL #1 respectively comprise the amino acid sequences of SEQ ID NOs: 185 and 186; the VL and VH regions of antibody 29TYL #10 respectively comprise the amino acid sequences of SEQ ID NOs: 187 and 188; the VL and VH regions of antibody 31YCM #3 respectively comprise the amino acid sequences of SEQ ID NOs: 189 and 190; the VL and VH regions of antibody 3 YCM #5 respectively comprise the amino acid sequences of SEQ ID NOs: 191 and 192; and the VL and VH regions of antibody 2835-28 respectively comprise the amino acid sequences of SEQ ID NOs: 193 and 194.

The present scFv/recombinant antibody may serve as an agonist antibody or an antagonist antibody against the antigen. According to certain embodiments of the present disclosure, the present scFv/recombinant antibody is an antagonist antibody of HER2, and the treatment of the present scFv/recombinant antibody exhibiting an therapeutic effect on cancers, especially HER2-expressing cancers (e.g., breast cancer, ovarian cancer, bladder cancer, salivary gland cancer, endometrial cancer, pancreatic cancer, and non-small-cell lung cancer (NSCLC)).

Accordingly, another aspect of the present disclosure is directed to a method for treating a cancer (e.g., a HER2-expressing cancer) in a subject; the method comprises administering to the subject an effective amount of the present scFv/recombinant antibody.

(b) Primer design and heavy chain/light chain variable domain library construction—A phage displayed library for each of the GH libraries' light and heavy chain was constructed based on the oligonucleotide-directed mutagenesis procedure, in which the sequences of CDR-L1, L2, L3, H1, H2 and H3 were diversified by the primers listed in in Table 1.

TABLE 1

Primers for diversifying CDR sequences in GH3-6~13 antibody libraries

| Target CDR | Template (SEQ ID NO) | Primer | Primer sequence (SEQ ID NO) | Diversified CDR sequence (SEQ ID NO) | Number of amino acid residues comprised in CDR |
|---|---|---|---|---|---|
| CDR-L1 | 1 | 9AL101 | 7 | 8 | 17 |
| | | 9AL102 | 9 | 10 | 16 |
| CDR-L2 | 2 | 9AL201 | 11 | 12 | 8 |
| | | 9AL202 | 13 | 14 | 8 |
| | | 9AL203 | 15 | 16 | 8 |
| | | 9AL204 | 17 | 18 | 8 |
| CDR-L3 | 3 | 9AL301 | 19 | 20 | 9 |
| | | 9AL302 | 21 | 22 | 9 |
| CDR-H1 | 4 | 9AH101 | 23 | 24 | 13 |
| | | 9AH102 | 25 | 26 | 13 |
| | | 9AH103 | 27 | 28 | 13 |
| | | 9AH104 | 29 | 30 | 13 |
| | | 9AH105 | 31 | 32 | 13 |
| | | 9AH106 | 33 | 34 | 13 |
| | | 9AH107 | 35 | 36 | 13 |
| | | 9AH108 | 37 | 38 | 13 |
| CDR-H2 | 5 | 9AH201 | 39 | 40 | 10 |
| | | 9AH202 | 41 | 42 | 10 |
| CDR-H3-6 | 6 | 9AH3601-02 | 43-44 | 45-46 | 6 |
| CDR-H3-7 | | 9AH3701-05 | 47-51 | 52-56 | 7 |
| CDR-H3-8 | | 9AH3801-03 | 57-59 | 60-62 | 8 |
| CDR-H3-9 | | 9AH3901-04 | 63-66 | 67-70 | 9 |
| CDR-H3-10 | | 9AH31001-05 | 71-75 | 76-80 | 10 |
| CDR-H3-11 | | 9AH31101-10 | 81-90 | 91-100 | 11 |
| CDR-H3-12 | | 9AH31201-15 | 101-115 | 116-130 | 12 |
| CDR-H3-13 | | 9AH31301-21 | 131-151 | 152-172 | 13 |

The subject treatable with the present scFv, recombinant antibody and/or method is a mammal, for example, a human, a mouse, a rat, a rabbit, a goat, a sheep, a monkey and a horse. Preferably, the subject is a human.

The following Examples are provided to elucidate certain aspects of the present invention and to aid those of skilled in the art in practicing this invention. These Examples are in no way to be considered to limit the scope of the invention in any manner. Without further elaboration, it is believed that one skilled in the art can, based on the description herein, utilize the present invention to its fullest extent. All publications cited herein are hereby incorporated by reference in their entirety.

EXAMPLE

Materials and Methods

Generic Human (GH) Synthetic Antibody Library Construction

The phage-displayed synthetic scFv libraries were constructed and characterized by the following procedures:

(a) scFv template preparation—The framework sequence of GH scFv libraries was based on the human IGKV1-NL1*01/IGHV3-23*04 germline sequence and cloned into pCANTAB5E phagemid via SfiI and NotI restriction sites. TAA stop codons were introduced in CDRs to ensure that only the phagemids carrying the mutagenic oligonucleotides would produce pIII fusion scFv on phage surface.

In brief, mutagenic oligonucleotides for each CDR were mixed and phosphorylated by T4 polynucleotide kinase in 70 mM Tris-HCl (pH 7.6), 10 mM $MgCl_2$, 1 mM ATP and 5 mM dithiothreitol (DTT) at 37° C. for 1 hour. The phosphorylated oligonucleotides were then annealed to uracilated single-stranded DNA template, at a molar ratio of 3:1 (oligonucleotide: ssDNA), by heating the mixture at 90° C. for 2 minutes, followed by a temperature decrease of 1° C./min to 20° C. in a thermal cycler. Subsequently, the template-primer annealing mixture was incubated in 0.32 mM ATP, 0.8 mM dNTPs, 5 mM DTT, 600 units of T4 DNA ligase, and 75 units of T7 DNA polymerase to prime in vitro DNA synthesis. After overnight incubation at 20° C., the synthesized dsDNA was desalted and concentrated by a centrifugal filter, then electroporated into Escherichia coli (E. coli) strain ER2738 at 3000 V with an electroporator. Typically, 1 μg of dU-ssDNA produced about $10^7$-$10^8$ recombinant phage variants, and 75-90% of the phage variants carried mutagenic oligonucleotides at the three CDR regions simultaneously.

(c) Protein A/L selection of functional scFv variants—The rescued phage libraries of light- and heavy-chain were precipitated with 20% PEG/NaCl and resuspended in phosphate-buffered saline (PBS) for the following protein A/L, selection process. First, 96-well immunoplates were coated overnight at 4° C. with Protein A (for selection of heavy chain-diversified libraries) or Protein L (for selection of light chain-diversified libraries) (1 μg/100 μL PBS per well), followed by blocking with 5% skim milk in PBST (PBS containing 0.05% (v/v) Tween 20, pH 7.4) for 1 hour. Then, 100 µL of resuspended phage library ($10^{13}$ cfu/mL) was added to each well for 1 hour under gentle shaking. The plate was washed 12 times with 200 µL PBST, and 2 times with 200 µL PBS. The bound phages were eluted with 100 µL of 0.1 M HCl/glycine (pH 2.2) per well, followed by neutralization with 8 µL of 2 M Tris-base buffer (pH 9.1). The eluted phages were mixed with 1 mL of E. coli strand ER2738 ($A_{600\ nm}$=0.6) at 37° C. for 15 minutes. Infected E. coli was titered, and amplified with 50 mL of 2×YT containing 100 µg/mL ampicillin at 37° C. overnight. After centrifugation, the bacterial pellet was resuspended and its phagemid DNA was extracted.

(d) Combination of functional scFv variants into the GH antibody libraries—Each of the GH libraries was assembled in scFv format via PCR. In the first round of PCR, two variable domains VL and VH were respectively amplified from light- and heavy-chain library after selection for binding to Protein A/L, by using the primers $V_{Lfor}$ (5'-GGGC-CCAGCCGGCCATGGCCGATATTCAAATGACCCA-GAGCCCGAGC-3', SEQ ID NO: 195), $V_{Lrev}$ (5'-GGAAGATCTAGAGGAACCACCGCGTTTGATTTCCA CTTTGGTGCCTTGACC-3', SEQ ID NO: 196), $V_{Hfor}$ (5'-GGTGGTTCCTCTAGATCTTCCTCCTCTGGTGGCG-GTGGCTCGGGCGGTGGTGGGGAA GTGCAGCTG-GTGGAATCGGG-3', SEQ ID NO: 197), and $V_{Hrev}$ (5'-CCTGCCTGCGGCCGCTGACGCCGAGC-3', SEQ ID NO: 198). PCR reactions were performed in a volume of 50 µL by use of DNA polymerase, in which 100 ng DNA template was reacted with 0.3 µM of each primer for 25 cycles (95° C. for 30 seconds, 65° C. for 30 seconds, 72° C. for 1 minute) followed a 10-minute final synthesis step. The PCR products were digested with EcoRI and then purified by agarose gel electrophoresis.

In the second round of PCR, two variable domains were assembled using the overlapping primers: Overlapfor (5'-GAGGAGGAGGAGGAGGAGGCGGGGCCCAGCCG-GCCATGGCCGATATTC-3', SEQ ID NO: 199) and Overlaprev (5'-GAGGAGGAGGAGGAGGAGCCTGCCTGCGGCCGCT GACGCC-3', SEQ ID NO: 200). 100 ng of the purified VL and VH products of the first round of PCR were used in a a volume of 50 µL using DNA polymerase and 0.3 µM of each primer for 30 cycles (95° C. for 30 seconds, 65° C. for 30 seconds, 72° C. for 1 minute and 30 seconds) followed by a 10-minute final synthesis step. The assembled VL-VH fragments were doubly digested with SfiI and NotI and cloned into pCANTAB5E phagemid vector. The resulting ligation product was electroporated into E. coli strain ER2738 at 3000 V with an electroporator.

The thus-produced scFv library are respectively designated as GH3-6, GH3-7, GH3-8, GH3-9, GH3-10, GH3-11, GH3-12 and GH3-13 libraries.

Selection and Screening of Anti-Protein Monoclonal scFvs from Phage-Displayed scFv Libraries The monoclonal scFv was selected from the present phage-displayed synthetic scFv libraries by the following procedures:

(a) Phage display selection-amplification cycles—The recombinant protein antigen (10 µg per well) was coated on 96-well immunoplates. The plate was blocked with 5% skim milk in PBST for 1 hour. Next, 100 µL of resuspended polyethylene glycol/NaCl-precipitated phage library ($10^{13}$ cfu/mL in blocking buffer) was added to each well for 1 hour under gently shaking. The plate was washed 12 times with 200 µL PBST, and 2 times with 200 µL PBS. The bound phages were eluted with 100 µL of 0.1 M HCl/glycine (pH 2.2) per well, immediately neutralized with 8 µL of 2 M Tris-base buffer (pH 9.1). The eluted phages were mixed with 1 mL of E. coli strand ER2738 ($A_{600\ nm}$=0.6) at 37° C. for 30 minutes; uninfected bacteria were eliminated by adding ampicillin. After ampicillin treatment for 30 minutes, the bacterial culture was infected with 100 µL M13KO7 helper phage (~$10^{11}$ CFU total) at 37° C. for 1 hour, and then added to 50 mL of 2×YT medium containing kanamycin 50 µg/mL and ampicillin 100 µg/mL overnight at 37° C. with vigorously shaking. The rescued phage library was precipitated with 20% polyethylene glycol/NaCl, and resuspended in PBS. The concentrated phage solution was used for the next round of panning.

(b) Ratio of output/input phage library titer—In each biopanning procedure as described above, the output (eluted) and input phage were tittered with fresh-prepared E. coli strand ER2738, and the ratio of output/input titer was calculated.

(c) Polyclonal soluble scFvs in E. coli culture media evaluated for antigen binding with ELISA—50 µL rescued phage from each cycle of biopanning above was mixed with 750 µL of E. coli strand ER2738 ($A_{600\ nm}$=0.6) in 96-well deep well culture plate, and incubated at 37° C. with vigorously shaking. One hour later, 100 µL ampicillin was added to final concentration 100 µg/mL ampicillin. 100 µL of 10 mM IPTG was added to each well (final concentration 1 mM) after $A_{600\ nm}$>1.0, and the plate was incubated at 37° C. with vigorously shaking overnight. The plate was centrifuged at 3000×g for 10 minutes and the supernatants were used for ELISA binding assay below.

(d) ELISA assay for soluble scFv-antigen binding—After 2-3 rounds of selection-amplification cycle, single colonies were picked and soluble monoclonal scFvs secreted in the E. coli cultures were prepared. 96-well immunoplate coated with the protein antigen 0.5 µg per well was blocked with 5% skim milk in PBST for 1 hour. 100 µL cultured medium with secreted scFv was added to the plate for binding. After 1 hour of binding and washing six times with PBST, 100 µL anti E-tag-HRP (1:4000 dilution) was added to each well. After 1 hour incubation, the plate was washed six times with PBST buffer and twice with PBS, developed for 3 min with 3,3',5,5'-tetramethyl-benzidine peroxidase substrate (TMB substrate), quenched with 1.0 M HCl and read spectrophotometrically at 450 nm.

(e) ELISA assay for soluble scFv folding with Protein L/Protein A—In addition to test the antigen binding of secreted scFv, well-folded scFvs were identified with Protein L and Protein A binding. 96-well immunoplate coated with Protein L (0.1 µg per well) was blocked followed by adding scFv cultured medium as described above. The signals were developed with Protein A conjugated with horseradish peroxidase (1:5000 dilution).

IgG Expression and Purification

The IgG antibody was produced by the scFv selected from the present phage-displayed scFv libraries in accordance with the followed procedures:

(a) Convert scFv to IgG format—The VL and VH cDNAs were amplified from the scFv plasmids of binder phages by PCR and then cloned into mammalian expression vector pIgG. The VL domain cDNA was amplified by PCR with proof-reading DNA polymerase using primer set GH2-VL-F-KpnI (5'-CAGGTGCACGATGTGATGGTACCGATAT-TCAAATGACCCAGAGCCCGAGCAGCCT GAGC-3', SEQ ID NO: 201) and GH2-VL-R (5'-TGCAGCCACCG-TACGTTTGATTTCCACCTTGGTGCC-3', SEQ ID NO: 202); and the VH domain cDNA was amplified by primers GH2-VH-F (5'-CGTGTCGCATCTGAAGTGCAGCTG-GTGGAATCGGGA-3', SEQ ID NO: 203) and GH2-VH-R-NheI (5'-GACCGATGGGCCCTTGGTGCTAGC-CGAGCTCACGGTAACAAGGGTGCC-3', SEQ ID NO: 204). PCR reactions were performed in a volume of 50 μL with 100 ng DNA template and 1 μL of 10 μM of each primer for 30 cycles (95° C. for 30 seconds, 56° C. for 30 seconds, 72° C. for 30 seconds) followed a 10-minute final synthesis step at 72° C. The PCR products were extracted from 1.0% agarose electrophoresis gel. The linker DNA fragment between VL and VH domains was obtained from pIgG vector by PCR amplification as above, using primer set GH2-IgG-linker-F (5'-AAGGTGGAAATCAAACGTACG-GTGGCTGCACCATCTGTC-3', SEQ ID NO: 205) and GH2-IgG-linker-R (5'-CTGCACTTCAGATGCGA-CACGCGTAGCAACAGC-3', SEQ ID NO: 206). The linker fragment includes the constant domain of light chain, bovine growth hormone (BGH) polyA signal, and human cytomegalovirus (CMV) promoter followed by the signal peptide of IgG heavy chain. The above three DNA fragments (VL domain, linker, and VH domain) were assembled by PCR amplification using primer set GH2-VL-F-KpnI and GH2-VH-R-NheI for 30 cycles (95° C. for 30 seconds, 58° C. for 30 seconds, 72° C. for 90 seconds). The PCR products were extracted from 1% agarose electrophoresis gel and cloned into pIgG vector. The constructed vector contains both light chain and heavy chain of IgG, controlled by human cytomegalovirus (CMV) promoter separately.

(b) Transfection of HEK293 F cells and IgG expression—For 500 mL culture transfection, suspension 293-F cells were adjusted to the density of $1.0 \times 10^6$ cells/mL. The plasmid DNA (500 μg), diluted in 25 mL serum free medium and sterile with 0.2 μm syringe filter, was mixed vigorously with 25 mL medium containing 1 mg of cationic polymer polyethylenimine (PEI). After incubating at room temperature for 20 minutes, the mixture was added dropwise to the cells with slight shaking, and then the cells were grown in reach-in incubator at 37° C. Tryptone N1 was added to a final concentration of 0.5% at 24-hour post-transfection. After 5 days' culture, the supernatant was collected by centrifugation at 8000×g for 30 minutes, and filtered with 0.8 μm membrane filter. The supernatant was loaded on Protein A affinity column, and eluted with 0.2 N glycine-HCl at pH 2.5 into 1/10 volume of 1 M Tris-HCl buffer at pH 9.1. The IgG proteins were further purified by gel filtration column to remove high molecular weight aggregates.

Antibody-Antigen Complex Structure Dataset

Ab-PRO—To maximize the diversity of antibody-protein complex, 744 antibody-protein (with antigen amino acid length >35) complexes were retrieved from SAbDab (Dunbar J, et. al., SAbDab: the structural antibody database. *Nucleic Acids* Res (2014), 42 (Database issue): D1140-1146). 403 complexes remained after removing redundant antibodies with the 95% threshold of VH sequence identity. To ensure epitope diversity, the protein antigens were clustered by the sequence identity threshold of 70% to generate 74 protein antigen clusters. Clusters with single complex structure were selected as representatives in the Ab-PRO dataset. For each cluster with complex size >1, pairwise comparison of overlapping epitope atoms in each pair of protein antigens allowed to eliminate redundant complexes with epitope overlap of more than 50% by removing the complex with smaller epitope in the comparing pair. Total 281 antibody-protein complexes were finally selected as representative antibody-protein complexes in Ab-PRO.

$EC_{50}$ for Antibody-Antigen Interaction

The $EC_{50}$ of IgGs was determined by the titrations of IgG antibodies on immobilized HER2-ECD with ELISA. In brief, the HER2-ECD antigen (0.2 μg per well) were coated in PBS buffer (pH 7.4) on 96-well immunoplates overnight at 4° C., and blocked with 5% skim milk in PBST for 1 hour. In the meantime, IgGs in PBST with 5% milk were prepared at 11 concentration by twofold serial dilutions. After blocking, 100 μL diluted IgG samples were added to each well, and incubated for 1 hour under gentle shaking. The plate was washed 6 times with 300 μL PBST and then added with 100 μL horse-radish peroxidase/anti-human IgG antibody conjugate (1:2000 dilution) in PBST with 5% milk for 1 hour incubation. The plates were washed six times with PBST buffer and twice with PBS, developed with TMB substrate for 3 minutes, quenched with 1.0 M HCl and read spectrophotometrically at 450 nm. The $EC_{50}$ (ng/mL) was calculated according to Stewart and Watson method.

Analyses of Linear/Conformational Epitopes Recognized by IgGs

To investigate the linear/conformational epitopes of selected anti-HER2 IgGs, 10% SDS-PAGE under denaturing or non-denaturing condition was used to characterize the purified HER2-ECD (0.5 ug/well). For denaturing condition, antigen was mixed with reducing sample buffer containing 20 mM dithiothreitol (DTT), boiled at 95° C. for 5 minutes. For non-denaturing condition, antigen was mixed with only sample buffer without reducing reagent and boiling treatment. After the HER2-ECD antigen bands were blotted onto a PVDF membrane, they were probed with 1.5 μg/mL purified IgGs, and horseradish peroxidase-conjugated anti-Human IgG (1:3000 dilution). Images of bands were detected using western blotting substrate.

HER2-ECD Binding of scFv with AL1-RFP on Cell Surface by Flow Cytometry

HER2-expressing gastric cancer N87 cells were used for scFv-HER2-ECD binding by flow cytometry analysis. First, Cells were scraped and went through strainer with 40-micron pore. About $2 \times 10^5$ cells were incubated with 100 μL of 0.5 nM scFv at 4° C. for 30 minutes, washed once with 0.5% FBS 1× PBS (wash buffer), mixed with 1 μg AL1-RFP in 50 μL wash buffer at 4° C. for 20 minutes, and then washed twice with washer buffer. After centrifugation and resuspension, cells were analyzed for RFP signal by flow cytometry. Mean fluorescence intensity (MFI) was used to indicate affinity of scFvs in binding HER2-ECD.

Cytotoxicity Assay

For the purpose of evaluating the cytotoxic effect of the present scFvs, adaptor-toxin fusion proteins AL1-PE38KDEL and AL2-PE38KDEL was first produced by linking the adaptor sequences, AL1 (SEQ ID NO: 207) or AL2 (SEQ ID NO: 208), with cytotoxic drug PE38KDEL (a truncated form of Pseudomonas Exotoxin (PE) A subunit toxin, SEQ ID NO: 209). Then, $10^4$ gastric cancer N87 cells/well were seeded in 96-well plates. 0.5 nM scFvs were pre-incubated with AL1-PE38KDEL or AL2-PE38KDEL at a molar ratio of 1:1 (AL1-PE38KDEL) or 2:1 (AL2-PE38KDEL) for 1 hour at room temperature so as to form non-covalently linked immunotoxins. scFv-AL1-PE38KDEL/AL2-PE38KDEL mixtures were added to cell culture without serum. After 4 hours of incubation at 37° C., the antibody toxin mixture was replaced by fresh normal medium with serum. After 4 days of culture at 37° C., the number of viable cells was quantified. Percentage of cell viability was calculated by the following equation:

% of cell viability=OD450 nm (antibody treated cells)/OD450 nm (negative control cells)×100%.

Example 1 Characterization of the Present Synthetic scFv Library

The sequences and structures of the six synthetic scFv libraries (including GH3-6, GH3-7, GH3-8, GH3-9, GH3-10, GH3-11, GH3-12 and GH3-13) established in accordance with the procedures of Materials and Methods were characterized in this example.

According to the analytic results, the main canonical structure configuration of CDR H1-H2-L1-L2-L3 of the present scFv libraries is 1-2-3-1-1 or 1-2-4-1-1. The binding affinity of the scFv scFvs of the present scFv libraries was validated with 4 randomly selected protein antigens. As summarized in Table 2, scFvs selected from each of the synthetic antibody libraries via the biopanning procedure illustrated in Materials and Methods exhibited binding affinity to at least three randomly selected protein antigens. The data suggested that each of the GH synthetic antibody libraries contains well-folded scFv variants binding to randomly selected protein antigens.

TABLE 2

Number of scFvs selected from the present scFv libraries

| Library name | CDR-H3 length | Pro A/L | HER2 | HER3 | PDL1 | MSLN |
|---|---|---|---|---|---|---|
| GH3-6~13 | 6 | 80/80 | 2/7 | 1/14 | 2/8 | 6/11 |
| | 7 | 94/94 | 10/65 | 3/7 | 3/8 | 5/8 |
| | 8 | 107/107 | 19/53 | 15/42 | 6/12 | 15/17 |
| | 9 | 57/57 | 8/29 | 9/24 | 2/4 | 2/4 |
| | 10 | 92/92 | | 3/24 | 5/15 | 4/8 |
| | 11 | 99/99 | | 25/83 | 6/9 | 2/3 |
| | 12 | 102/102 | 2/2 | 15/33 | 1/1 | 4/9 |
| | 13 | 129/129 | 1/6 | 24/69 | 10/20 | 13/17 |

Single clonal isolated soluble scFvs binding to Protein A and Protein L and to the corresponding antigen with ELISA above $OD_{450}$ threshold of 0.5 after 2~3 rounds of biopanning were randomly selected for sequencing. In each of the cells with numbers in the Table, the first number indicates non-redundant scFv sequences discovered and the second number after '/' indicates the total sequenced positive clones. The detailed experimental procedures are described in Materials and Methods. The full name of all protein antigens is the following:
Pro A/L: Protein A and Protein L;
HER2: human epidermal growth factor receptor 2;
HER3: human epidermal growth factor receptor 3;
PDL1: Programmed death-ligand 1;
MSLN: Mesothelin.

Example 2 Distribution of Hot Spot Residues in the CDRs of the Synthetic Antibody Libraries In order to compare the hot spot residue distributions on antibodies in nature versus those on the antibodies from the synthetic antibody libraries, hot spot residues on the scFv structures were predicted by ISMBLab-PPI method as described by Peng HP et. al. (Origins of specificity and affinity in antibody-protein interactions, *Proc Natl Acad Sci USA* (2014), 111(26):E2656-2665). A query scFv structure derived experimentally or computationally was the only required input for the prediction of the atomistic interaction propensities of the query antibody surface atoms to be involved in a combination site for a protein antigen. The output of the predictors for each of the query antibody surface atoms was normalized into PCL (prediction confidence level) ranging from 0 to 1, which represented the atomistic propensity for the query antibody surface atom to interact with a protein antigen. A residue on the query antibody structure with maximal atomistic propensity $\geq 0.45$ was predicted as a hot spot residue. The predictions were correlated with experimentally determined hot spot residues defined by the threshold of $\Delta\Delta G \geq 1$ kcal/mol in alanine-scanning experiments with Matthews correlation coefficient of 0.43 and F1 score of 0.51. While the alanine-scanning of hot spot residues was experimentally intractable for the large number of scFv variants from the synthetic antibody libraries and from antibodies in nature, the computational hot spot predictions provided an alternative for evaluating the hot spot residue distributions in the CDRs of the scFvs.

Although the CDR sequence length configurations of the synthetic antibody libraries resembled those of the prominent antibody structures in nature, the CDRs of the synthetic antibody libraries are much more densely enriched with hot spot residues than those of the antibodies in nature (FIG. 1). As summarized in Table 2, each scFv library had two sets of scFv sequences collected from the validation experiments, including: set (F)—scFv sequences known to fold properly (Protein A/L binding; numbers of non-redundant sequences as shown in the column labelled ProA/L in Table 2); and set (FB)—scFv sequences known to fold and to bind to the corresponding protein antigen (binding to Protein A/L, and the corresponding antigens; numbers of non-redundant sequences as shown in the columns labelled by the corresponding antigen names in Table 2). In addition, for each of the scFv libraries, the scFv sequence set (D) contained 200 randomly selected theoretical scFv sequences based on the CDR designs (Table 1). The 3D structures of these sets of scFvs were modeled, and the distribution of hot spot residues in CDR regions thereof were predicted with ISMBLab-PPI and compared with that of the nature antibodies (i.e., Ab-PRO 13-10-16/17-8-9 dataset). The CDR-L1~H2 in the scFvs of the set (D)s (box plots with D symbol in FIG. 1, Panel A) were designed with enhanced hot spot residues by several folds as compared with those in the corresponding antibody structures in the Ab-PRO dataset (box plots with Ab-PRO symbol in FIG. 1, Panel A). The CDR-H3 hot spot residues increased with the CDR-H3 sequence length to average maximal 2 folds (box plots with D symbol in FIG. 1, Panel B) to those of the Ab-PRO antibodies (box plots with Ab-PRO symbol in FIG. 1, Panel B). These results indicated that the scFv variants in the synthetic antibody libraries were substantially enriched with CDR hot spot residues in comparison with those of the antibodies in nature.

Further, the data of FIG. 1 also indicated that the functional synthetic scFvs that were folded and bound to protein antigens were encoded with much more CDR hot spot residues (box plots with F and FB symbols in FIG. 1) in comparison with those of the corresponding functional antibody structures in the Ab-PRO dataset (box plots with Ab-PRO symbol in FIG. 1), suggesting that the antibody variable domain CDRs had substantial structural tolerance for enhanced distributions of hot spot residues.

Figure 2A:
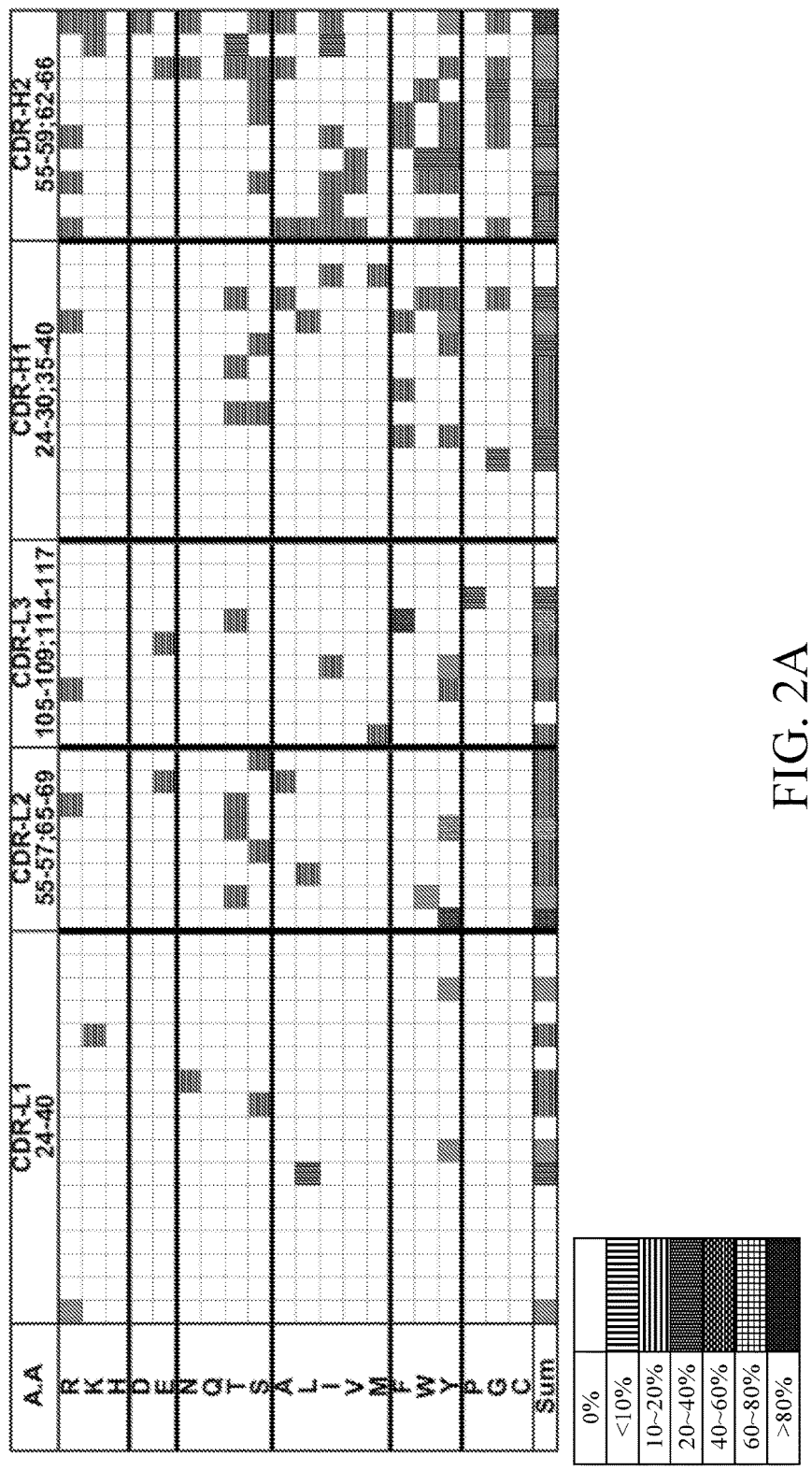
FIGS. 2A-2D are the results respectively depicting the frequencies and amino acid types of hot spot residues in CDR-L1, CDR-L2, CDR-L3, CDR-H1 and CDR-H2 of scFvs having 13-10-17-8-9 length configuration, including human germline antibody (FIG. 2A), scFv set (D) (FIG. 2B), scFv set (F) (FIG. 2C) and scFv set (FB) (FIG. 2D), according to another embodiment of the present disclosure.
Figure 2B:
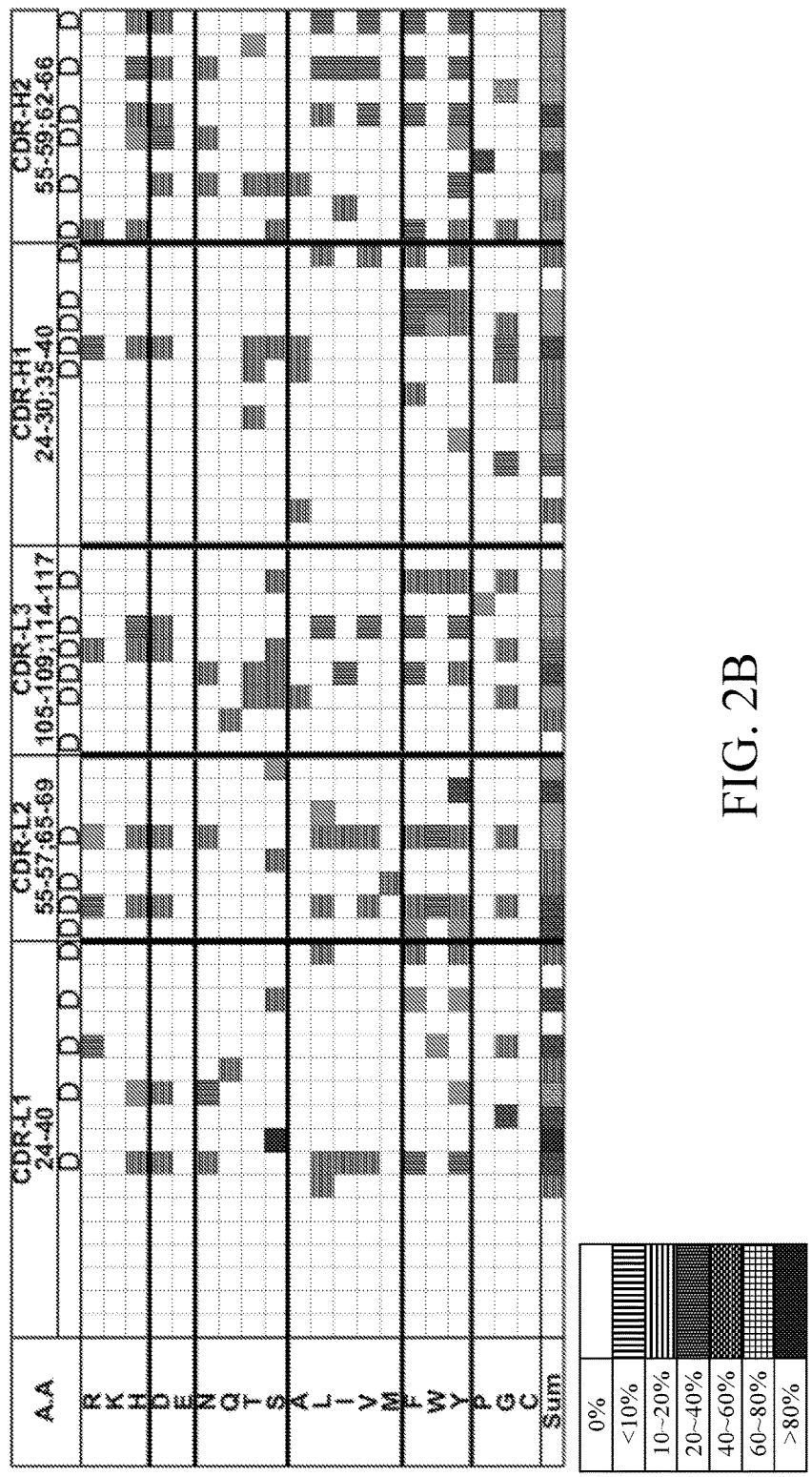
Figure 2C:
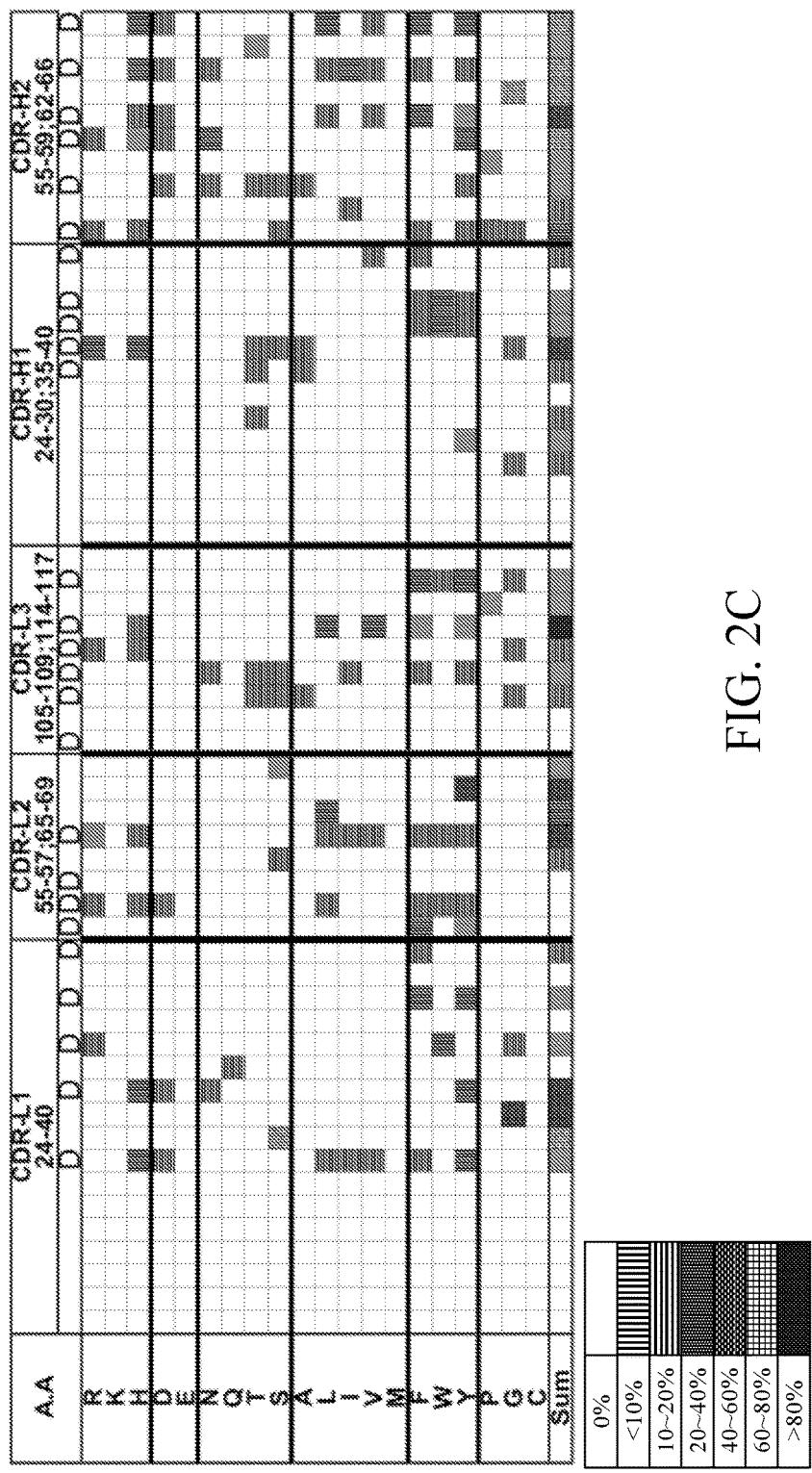
Figure 2D:
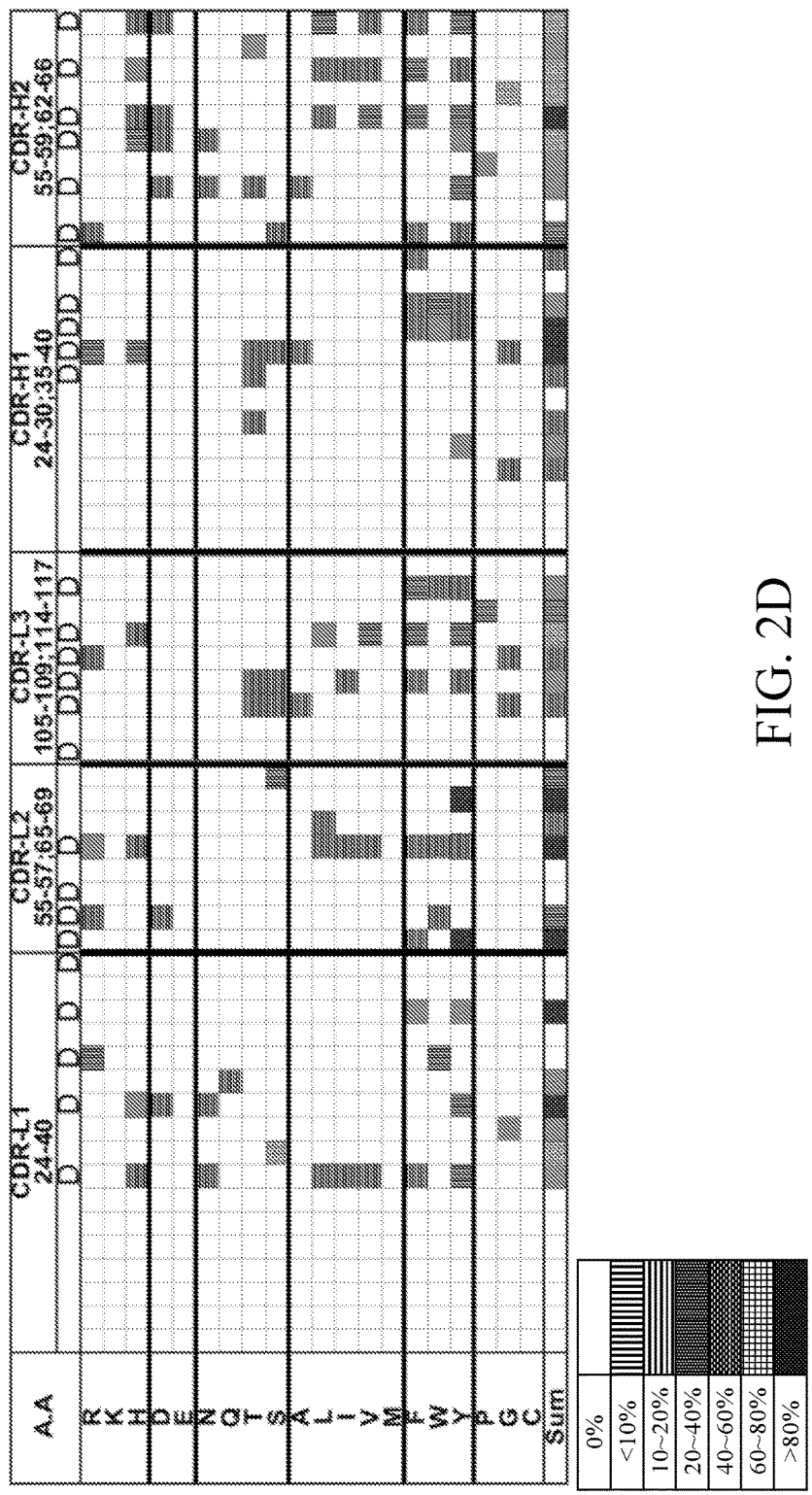
Figure 3A:
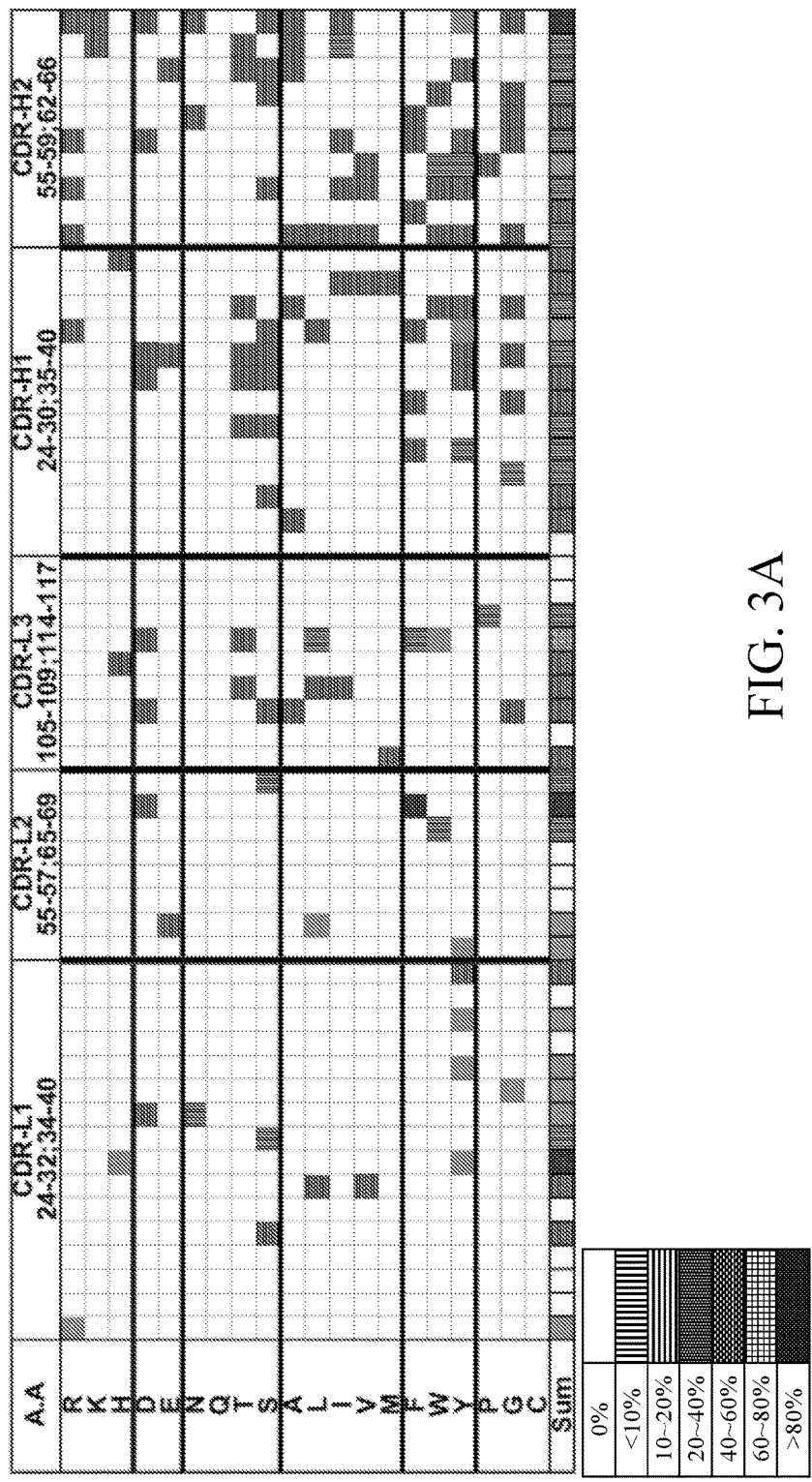
FIGS. 3A-3D are the results respectively depicting the frequencies and amino acid types of hot spot residues in CDR-L1, CDR-L2, CDR-L3, CDR-H1 and CDR-H2 of scFvs having 13-10-16-8-9 length configuration, including human germline antibody (FIG. 3A), scFv set (D) (FIG. 3B), scFv set (F) (FIG. 3C) and scFv set (FB) (FIG. 3D), according to another embodiment of the present disclosure.
Figure 3B:
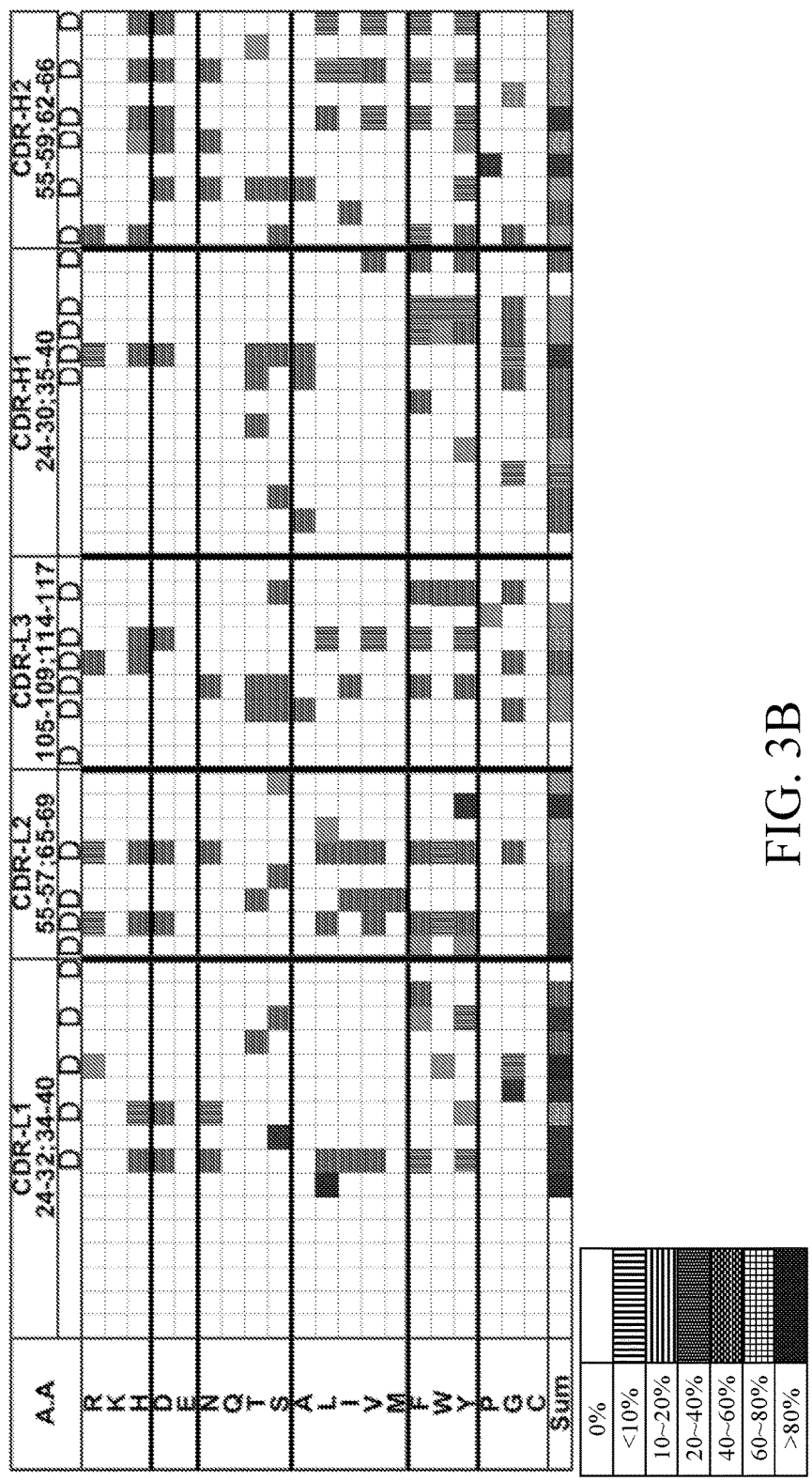
Figure 3C:
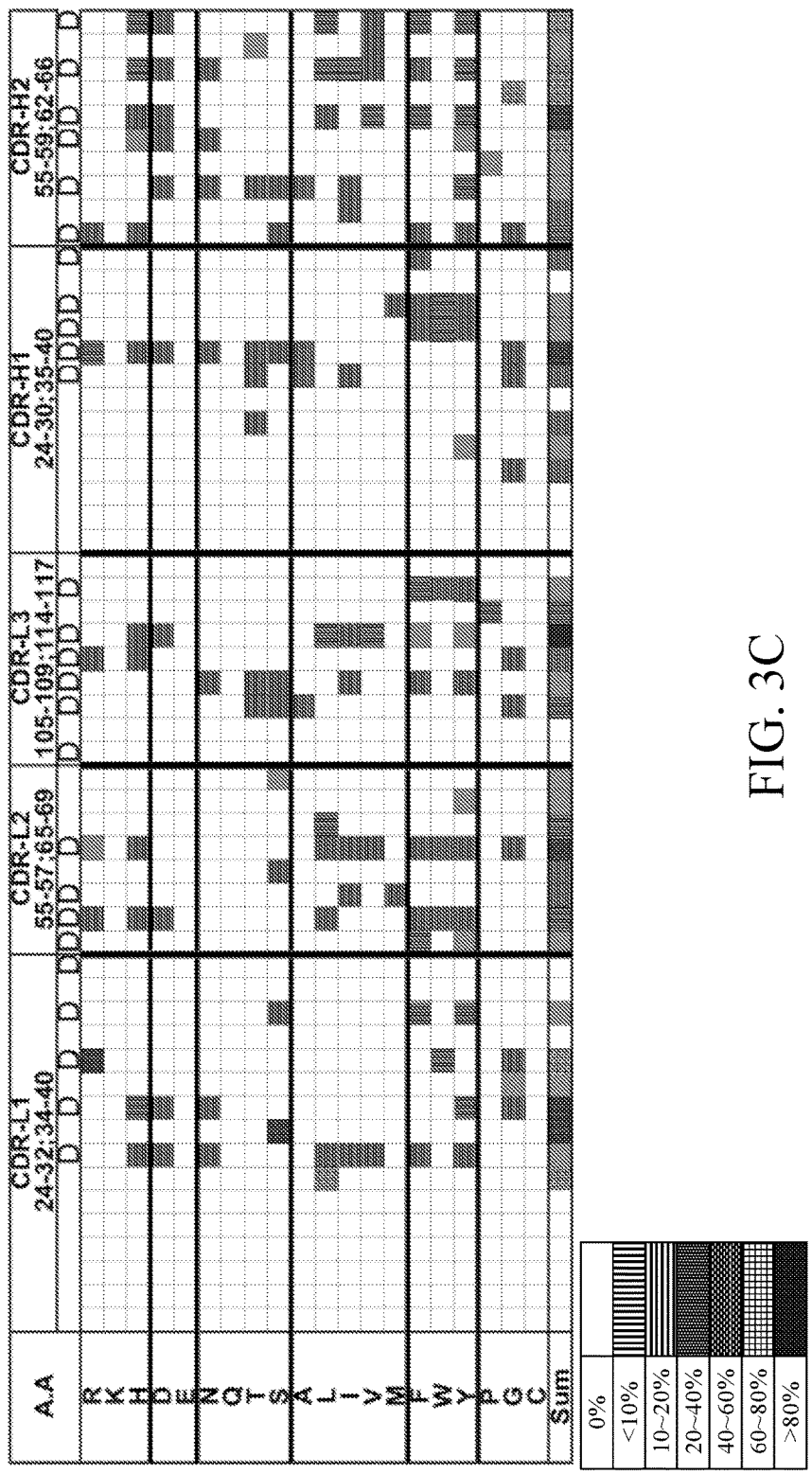
Figure 3D:
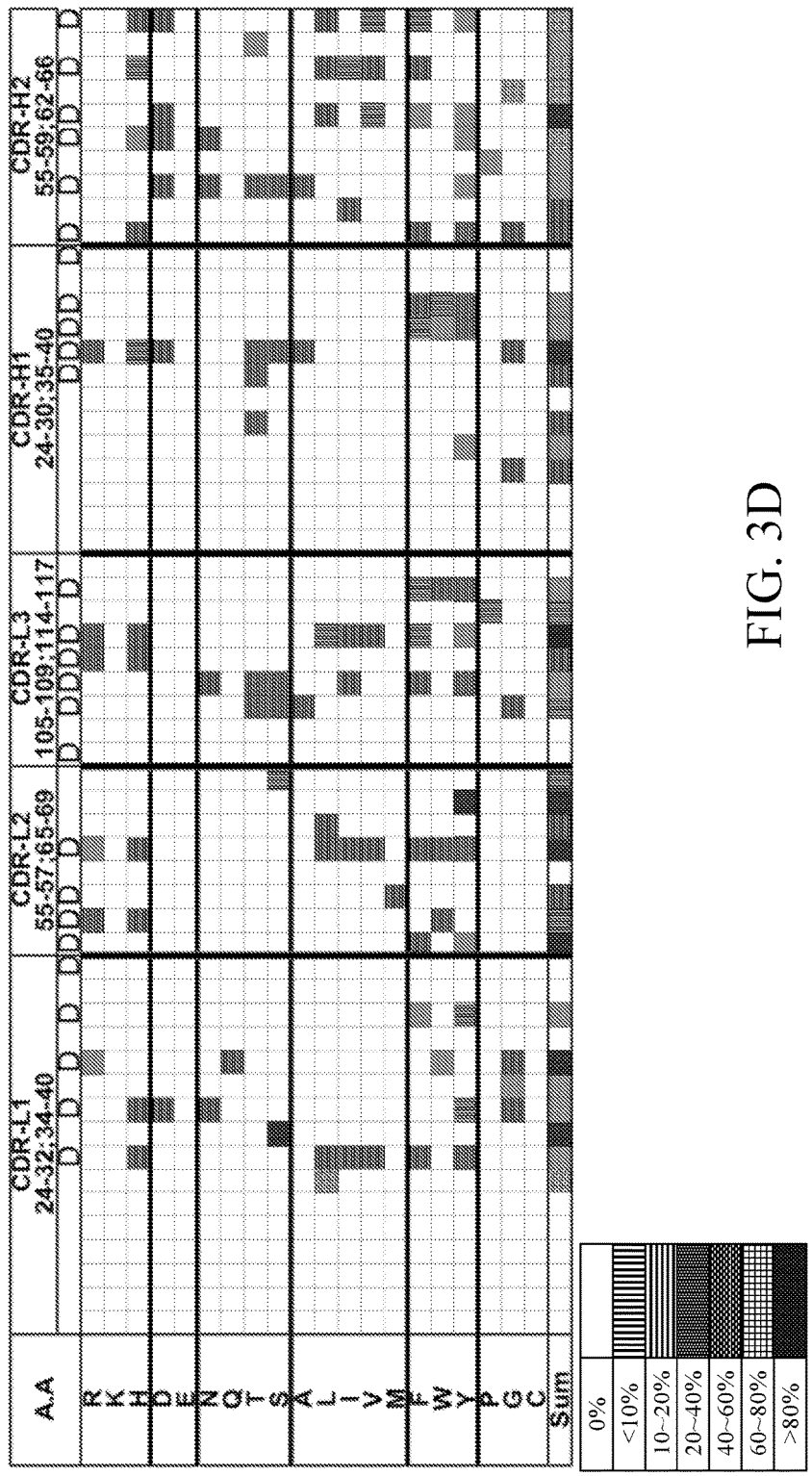

The CDR hot spot residue distributions on the scFv variants in the synthetic antibody libraries were different from those on human germline antibody variable domain sequences. The hot spot occurrence probabilities for each amino acid type at 13-10-17-8-9 (FIGS. 2A-2D) or 13-10-16-8-9 (FIGS. 3A-3D) CDR positions in the scFvs of set (D) (FIGS. 2B and 3B), set (F) (FIGS. 2C and 3C) and set (FB) (FIGS. 2D and 3D) were compared with the human germline antibody sequences of the same CDR length configuration (FIGS. 2A and 3A). The scFvs from set (D), set (F) and set (FB) had highly similar distribution patterns (Pearson correlation coefficient >0.9) for the hot spot residue positions and amino acid types (FIGS. 2A-2D and 3A-3D), indicating that the folding and binding requirements of the functional scFvs did not severely restrict the general distributions of the designed hot spot residue positions and amino acid types;

the synthetic scFvs had enhanced hot spot occurrence probabilities in the CDR with comparable position distributions as in human germline antibody variable domains of the same CDR length configuration (FIGS. 2A-2D and 3A-3D). The spatial distributions of the hot spot occurrence probabilities on antibody 3D structures confirmed that the designed scFvs had extensive paratopes for protein binding, comparable to those on the human germline antibody variable domains (data not shown). The scFv variants of the synthetic antibody libraries were distinguishable from the human germline antibody variable domain sequences by the enhanced distributions of CDR hot spot residues for protein-protein interactions.

In addition to antibody-protein interactions, the hot spot resides in CDR for antibody-peptide interactions were also predicted based on the same algorithm and parameterization as in the ISMBLab-PPI method. The general conclusions for antibody-protein interactions applied to antibody-peptide interactions as well, suggesting that the scFv variants of the synthetic antibody libraries are anticipated to be applicable to recognize both conformational (antibody-protein interactions) and linear (antibody-peptide interactions) epitopes on protein antigens. The distributions of the hot spot residues for both antibody-protein and antibody-peptide interactions were CDR position-dependent, mostly due to the dependence of the amino acid type distribution and the exposure level of the amino acid sidechain on its CDR position. The antibody-protein interaction hot spot residues were more abundant and were distributed in a more extensive surface area than the antibody-peptide interaction hot spot residues, in agreement with the general experimental observation that the peptide binding sites are smaller than the protein binding sites on antibodies. Overall, the amino acid type distributions of the predicted hot spot residues for both antibody-protein and antibody-peptide interactions were more prominent for the residues with aromatic sidechains, in agreement with the hot spot residues in protein-protein interactions.

Example 3 Antibodies from the Synthetic Antibody Libraries Bound to HER2-ECD with High Affinity and Specificity To test if the scFvs binding to recombinant HER2-ECD (Table 2) also recognized the HER2 receptor expressed on cell surfaces, the binding of the scFv randomly selected from the synthetic antibody libraries to cell surface HER2 was evaluated by cell-based assays. MFI (mean fluorescence intensity) measurements of the RFP (red fluorescence protein)-labeled HER2-ECD-binding scFvs from the synthetic antibody libraries indicated specific binding of the scFvs to the cell surface HER2 (Table 3). These scFv variants were cytotoxic to varying extent when non-covalently conjugated with pseudomonas exotoxin AL1-PE38KDEL or AL2-PE38KDEL (Table 3), due to cell surface receptor-mediated endocytosis of the PE38-conjugated scFvs binding to cell surface HER2. These results indicated that the scFvs selected and screened from the synthetic antibody libraries binding to recombinant HER2-ECD immobilized in ELISA wells also bound to HER2 on cell surface.

Finally, human IgG1s reformatted from the HER2-ECD-binding scFvs were characterized. The VL sequence, VH sequence, production yield and affinity to HER2-ECD ($EC_{50}$) for each of these IgG1s were summarized in Table 3.

TABLE 3

Characterization for specified IgG1s

| Name | VL sequence (SEQ ID NO) | VH sequence (SEQ ID NO) | Yield (mg/L) | $EC_{50}$ (ng/mL) | MFI* | % cell viability (AL1)** | % cell viability (AL2)*** |
|---|---|---|---|---|---|---|---|
| 30CHS-12 | 173 | 174 | 71.3 | 41 | 198 | 64.86 | 61.71 |
| 30CHS-13 | 175 | 176 | 76.1 | 41 | 93 | 75.83 | 77.72 |
| 30CHS-41 | 177 | 178 | 39.7 | 5 | 153 | 77.59 | 71.58 |
| 35CPT-9 | 179 | 180 | 58 | 31.7 | 287 | 69.85 | 17.85 |
| 35WYK-9 | 181 | 182 | 119 | 5.7 | 265 | 84.69 | 80.94 |
| 35WYK-16 | 183 | 184 | 69.5 | 6.2 | 299 | 72.18 | 41.38 |
| 29TYL#1 | 185 | 186 | 52.7 | 4.1 | 491 | 67.52 | 32.68 |
| 29TYL#10 | 187 | 188 | 89.6 | 3.8 | 444 | 79.93 | 64.77 |
| 31YCM#3 | 189 | 190 | 16.2 | 7.3 | 177 | 96.42 | 91.48 |
| 31YCM#5 | 191 | 192 | 30.3 | 6.3 | 165 | 89.47 | 71.81 |
| 2835-28 | 193 | 194 | 11.1 | 3.9 | 495 | 52.82 | 29.91 |
| Trastuzumab | | | | 4.5 | | | |

*The mean fluorescence intensities from the corresponding source scFvs complexed with AL1-RFP binding to cell surface HER2 on N87 cells.
**Cell viabilities (percentage of survival cells) for N87 cells treated with 0.5 nM scFvs complexed with AL1-PE38KDEL at the 1:1 molar ratio.
***Cell viabilities (percentage of survival cells) for N87 cells treated with 0.5 nM scFvs complexed with AL2-PE38KDEL at the 2:1 molar ratio.

The expression and purification of these IgG1s were characterized with SDS-PAGE gel. The data of Table 3 indicated that the antibodies from the synthetic antibody library set GH3-6-13 bound to the protein antigen HER2-ECD with high affinity, in which the affinities of the IgG1s were comparable to that of trastuzumab (an affinity-matured antibody) in terms $EC_{50}$ measurement. These results indicated that selected scFvs from the synthetic antibody libraries herein can be reformatted and expressed as IgG1 form with affinity frequently superior to that of the affinity-matured antibodies without explicit affinity maturation processes.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A phage-displayed single-chain variable fragment (scFv) library comprising a plurality of phage-displayed scFvs, wherein each of the plurality of phage-displayed scFvs comprises a first light chain complementarity determining region (CDR-L1), a second light chain CDR (CDR-L2), a third light chain CDR (CDR-L3), a first heavy chain CDR (CDR-H1), a second heavy chain CDR (CDR-H2), and a third heavy chain CDR (CDR-H3), wherein the CDR-L1 is encoded by a first coding sequence comprising the nucleic acid sequence of SEQ ID NO: 8 or 10;
the CDR-L2 is encoded by a second coding sequence comprising the nucleic acid sequence of SEQ ID NO: 12, 14, 16 or 18;
the CDR-L3 is encoded by a third coding sequence comprising the nucleic acid sequence of SEQ ID NO: 20 or 22;
the CDR-H1 is encoded by a fourth coding sequence comprising the nucleic acid sequence of SEQ ID NO: 24, 26, 28, 30, 32, 34, 36 or 38;
the CDR-H2 is encoded by a fifth coding sequence comprising the nucleic acid sequence of SEQ ID NO: 40 or 42; and
the CDR-H3 is encoded by a sixth coding sequence comprising the nucleic acid sequence of any of SEQ ID NOs: 45-46, 52-56, 60-62 67-70, 76-80, 91-100, 116-130 and 152-172.

2. The phage-displayed scFv library of claim 1, wherein
the first coding sequence has the nucleic acid sequence of SEQ ID NO: 7 or 9;
the second coding sequence has the nucleic acid sequence of SEQ ID NO: 11, 13, 15 or 17;
the third coding sequence has the nucleic acid sequence of SEQ ID NO: 19 or 21;
the fourth coding sequence has the nucleic acid sequence of SEQ ID NO: 23, 25, 27, 29, 31, 33, 35 or 37;
the fifth coding sequence has the nucleic acid sequence of SEQ ID NO: 39 or 41; and
the sixth coding sequence has the nucleic acid sequence of any of SEQ ID NOs: 43-44, 47-51, 57-59, 63-66, 71-75, 81-90, 101-115 and 131-151.

3. The phage-displayed scFv library of claim 1, wherein the phage is an M13 phage or a T7 phage.

4. The phage-displayed scFv library of claim 1, wherein at least one of the plurality of phage-displayed scFvs is specific for an antigen selected from the group consisting of human epidermal growth factor receptor 2 (HER2), human epidermal growth factor receptor 3 (HER3), Programmed death-ligand 1 (PD-L1) and Mesothelin (MSLN).

5. A method for preparing the phage-displayed scFv library of claim 1, comprising, (1) obtaining a first nucleic acid sequence that comprises a first, a second, a third, a fourth, a fifth and a sixth gene fragments respectively encoding the CDR-L1, CDR-L2, CDR-L3, CDR-H1, CDR-H2, and CDR-H3 of an immunoglobulin gene;
(2) inserting the first nucleic acid sequence into a first phagemid vector;
(3) respectively modifying the first, second, and third gene fragments by site-directed mutagenesis to produce a variable light chain (VL) library that comprises a first group of phage-displayed scFvs with the modified CDR-L1, CDR-L2, and CDR-L3; and respectively modifying the fourth, fifth, and sixth gene fragments by site-directed mutagenesis to produce a variable heavy chain (VH) library that comprises a second group of phage-displayed scFvs with the modified CDR-H1, CDR-H2, and CDR-H3;
(4) screening the VL library with a protein L, and selecting a third group of phage-displayed scFvs therefrom; and screening the VH library with a protein A, and selecting a fourth group of phage-displayed scFvs therefrom;
(5) respectively amplifying a plurality of second nucleic acid sequences encoding the modified CDR-L1, CDR-L2, and CDR-L3 from the corresponding phages, and a plurality of third nucleic acid sequences encoding the modified CDR-H1, CDR-H2, and CDR-H3 from the corresponding phages; and
(6) inserting the plurality of second and third nucleic acid sequences into a second phagemid vector so as to produce the phage-displayed scFv library of claim 1.

6. The method of claim 5, wherein in the step (3),
the first gene fragment is modified by the nucleic acid sequence of SEQ ID NO: 7 or 9;
the second gene fragment is modified by the nucleic acid sequence of SEQ ID NO: 11, 13, 15 or 17;
the third gene fragment is modified by the nucleic acid sequence of SEQ ID NO: 19 or 21;
the fourth gene fragment is modified by the nucleic acid sequence of SEQ ID NO: 23, 25, 27, 29, 31, 33, 35 or 37;
the fifth gene fragment is modified by the nucleic acid sequence of SEQ ID NO: 39 or 41; and
the sixth gene fragment is modified by the nucleic acid sequence of any of SEQ ID NOs: 43-44, 47-51, 57-59, 63-66, 71-75, 81-90, 101-115 and 131-151.

7. The method of claim 5, wherein the immunoglobulin gene of the step (1) encodes an antibody specific for VEGF.

8. The method of claim 5, wherein both the first and second phagemid vectors are derived from the M13 phage.

9. A method of producing a recombinant antibody from the phage-displayed scFv library of claim 1, comprising,
  (1) screening the phage-displayed scFv library of claim 1 with an antigen;
  (2) selecting the phages that display scFvs with binding affinity to the antigen;
  (3) respectively enabling the selected phages of the step (2) to express the scFvs, which are in soluble forms;
  (4) selecting one soluble scFv from the scFvs of the step (3) that exhibits high binding affinity to the antigen;
  (5) extracting a phagemid DNA corresponding to the phage that expresses the selected soluble scFv of the step (4);
  (6) respectively amplifying a first nucleic acid sequence that encodes the CDR-H1, CDR-H2, and CDR-H3, and a second nucleic acid sequence that encodes the CDR-L1, CDR-L2, and CDR-L3 by PCR using the phagemid DNA of the step (5) as a template;
  (7) inserting the first and second nucleic acid sequences into an expression vector that comprises a third and a fourth nucleic acid sequences, wherein the third nucleic acid sequence encodes the constant region of the heavy chain of an immunoglobulin, and the fourth nucleic acid sequence encodes the constant region of the light chain of the immunoglobulin; and
  (8) transfecting a host cell with the expression vector of the step (7) that comprises the first, second, third, and fourth nucleic acid sequences so as to produce the recombinant antibody.

10. The method of claim 9, wherein the first nucleic acid sequence is disposed at the upstream of the third nucleic acid sequence, and the second nucleic acid sequence is disposed at the upstream of the fourth nucleic acid sequence.

11. The method of claim 9, wherein the immunoglobulin is selected from the group consisting of immunoglobulin G (IgG), immunoglobulin A (IgA), immunoglobulin D (IgD), immunoglobulin E (IgE), and immunoglobulin M (IgM).

12. The method of claim 9, wherein the host cell is a mammalian cell.

13. The method of claim 9, wherein the antigen is HER2, HER3, PD-L1 or MSLN.

14. A recombinant antibody prepared from the phage-displayed scFv library of claim 1, comprising,
  a CDR-L1 that is encoded by the first coding sequence;
  a CDR-L2 that is encoded by the second coding sequence;
  a CDR-L3 that is encoded by the third coding sequence;
  a CDR-H1 that is encoded by the fourth coding sequence;
  a CDR-H2 that is encoded by the fifth coding sequence; and
  a CDR-H3 that is encoded by the sixth coding sequence.

15. The recombinant antibody of claim 14, wherein
  the first coding sequence has the nucleic acid sequence of SEQ ID NO: 7 or 9;
  the second coding sequence has the nucleic acid sequence of SEQ ID NO: 11, 13, 15 or 17;
  the third coding sequence has the nucleic acid sequence of SEQ ID NO: 19 or 21;
  the fourth coding sequence has the nucleic acid sequence of SEQ ID NO: 23, 25, 27, 29, 31, 33, 35 or 37;
  the fifth coding sequence has the nucleic acid sequence of SEQ ID NO: 39 or 41; and
  the sixth coding sequence has the nucleic acid sequence of any of SEQ ID NOs: 43-44, 47-51, 57-59, 63-66, 71-75, 81-90, 101-115 and 131-151.

16. The recombinant antibody of claim 15, wherein
  the variable regions of the light chain and the heavy chain of the recombinant antibody respectively comprise the amino acid sequences of SEQ ID NOs: 173 and 174;
  the variable regions of the light chain and the heavy chain of the recombinant antibody respectively comprise the amino acid sequences of SEQ ID NOs: 175 and 176;
  the variable regions of the light chain and the heavy chain of the recombinant antibody respectively comprise the amino acid sequences of SEQ ID NOs: 177 and 178;
  the variable regions of the light chain and the heavy chain of the recombinant antibody respectively comprise the amino acid sequences of SEQ ID NOs: 179 and 180;
  the variable regions of the light chain and the heavy chain of the recombinant antibody respectively comprise the amino acid sequences of SEQ ID NOs: 181 and 182;
  the variable regions of the light chain and the heavy chain of the recombinant antibody respectively comprise the amino acid sequences of SEQ ID NOs: 183 and 184;
  the variable regions of the light chain and the heavy chain of the recombinant antibody respectively comprise the amino acid sequences of SEQ ID NOs: 185 and 186;
  the variable regions of the light chain and the heavy chain of the recombinant antibody respectively comprise the amino acid sequences of SEQ ID NOs: 187 and 188;
  the variable regions of the light chain and the heavy chain of the recombinant antibody respectively comprise the amino acid sequences of SEQ ID NOs: 189 and 190;
  the variable regions of the light chain and the heavy chain of the recombinant antibody respectively comprise the amino acid sequences of SEQ ID NOs: 191 and 192; or
  the variable regions of the light chain and the heavy chain of the recombinant antibody respectively comprise the amino acid sequences of SEQ ID NOs: 193 and 194.

17. A method of treating a cancer in a subject, comprising administering to the subject an effective amount of the recombinant antibody of claim 14.

18. The method of claim 17, wherein
  the variable regions of the light chain and the heavy chain of the recombinant antibody respectively comprise the amino acid sequences of SEQ ID NOs: 173 and 174;
  the variable regions of the light chain and the heavy chain of the recombinant antibody respectively comprise the amino acid sequences of SEQ ID NOs: 175 and 176;
  the variable regions of the light chain and the heavy chain of the recombinant antibody respectively comprise the amino acid sequences of SEQ ID NOs: 177 and 178;
  the variable regions of the light chain and the heavy chain of the recombinant antibody respectively comprise the amino acid sequences of SEQ ID NOs: 179 and 180;
  the variable regions of the light chain and the heavy chain of the recombinant antibody respectively comprise the amino acid sequences of SEQ ID NOs: 181 and 182;
  the variable regions of the light chain and the heavy chain of the recombinant antibody respectively comprise the amino acid sequences of SEQ ID NOs: 183 and 184;
  the variable regions of the light chain and the heavy chain of the recombinant antibody respectively comprise the amino acid sequences of SEQ ID NOs: 185 and 186;
  the variable regions of the light chain and the heavy chain of the recombinant antibody respectively comprise the amino acid sequences of SEQ ID NOs: 187 and 188;
  the variable regions of the light chain and the heavy chain of the recombinant antibody respectively comprise the amino acid sequences of SEQ ID NOs: 189 and 190;

the variable regions of the light chain and the heavy chain of the recombinant antibody respectively comprise the amino acid sequences of SEQ ID NOs: 191 and 192; or the variable regions of the light chain and the heavy chain of the recombinant antibody respectively comprise the amino acid sequences of SEQ ID NOs: 193 and 194.

19. The method of claim 17, wherein the cancer having HER2 expressed thereon.

20. The method of claim 17, wherein the subject is a human.

* * * * *